US012635892B2

(12) United States Patent
Peters

(10) Patent No.: US 12,635,892 B2
(45) Date of Patent: *May 26, 2026

(54) NON-INVASIVE CARDIAC HEALTH ASSESSMENT SYSTEM AND METHOD FOR TRAINING A MODEL TO ESTIMATE INTRACARDIAC PRESSURE DATA

(71) Applicant: ACORAI AB, Domsten (SE)

(72) Inventor: Filip Ludwig Peters, Domsten (SE)

(73) Assignee: ACORAI AB, Domsten (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/000,317

(22) PCT Filed: Jun. 3, 2021

(86) PCT No.: PCT/EP2021/064940
§ 371 (c)(1),
(2) Date: Nov. 30, 2022

(87) PCT Pub. No.: WO2021/245203
PCT Pub. Date: Dec. 9, 2021

(65) Prior Publication Data
US 2023/0200664 A1     Jun. 29, 2023

Related U.S. Application Data

(63) Continuation-in-part of application No. 17/315,261, filed on May 7, 2021, now abandoned, which is a
(Continued)

(51) Int. Cl.
*A61B 5/00*      (2006.01)
*A61B 5/02*      (2006.01)
(Continued)

(52) U.S. Cl.
CPC ........ *A61B 5/02055* (2013.01); *A61B 5/0006* (2013.01); *A61B 5/002* (2013.01);
(Continued)

(58) Field of Classification Search
CPC .............. A61B 5/6898; A61B 5/02028; A61B 5/02055; A61B 5/02416; A61B 5/0261;
(Continued)

(56) References Cited

U.S. PATENT DOCUMENTS 7,096,060 B2     8/2006  Arand et al.
7,174,203 B2     2/2007  Arand et al.
(Continued)

FOREIGN PATENT DOCUMENTS

JP        3652791        5/2005
WO      2009111789      9/2009
(Continued)

OTHER PUBLICATIONS

Machine English translation of WO-2017103134-A1, Brettschneider T, 2017, pp. 1-13 (Year: 2017), (Posted on Feb. 10, 2023 in conjunction with USPTO Office Action of U.S. Appl. No. 17/315,261).
(Continued)

*Primary Examiner* — Sana Sahand
(74) *Attorney, Agent, or Firm* — Greenberg Traurig, LLP

(57)     ABSTRACT
The present disclosure relates to cardiac health assessment system for use with a handheld electronic device for assessing cardiac health of a user and a method for assessing cardiac health of a user. The disclosure further relates to systems and methods for training a machine learning model to estimate intracardiac pressure data.

16 Claims, 25 Drawing Sheets

Related U.S. Application Data continuation-in-part of application No. 16/946,025, filed on Jun. 3, 2020, now Pat. No. 11,234,630.

(51) Int. Cl.

| | |
|---|---|
| *A61B 5/0205* | (2006.01) |
| *A61B 5/026* | (2006.01) |
| *A61B 5/11* | (2006.01) |
| *A61B 5/26* | (2021.01) |
| *A61B 5/282* | (2021.01) |
| *A61B 5/332* | (2021.01) |
| *A61B 7/04* | (2006.01) |
| *A61B 8/04* | (2006.01) |
| *A61B 8/06* | (2006.01) |
| *A61B 5/021* | (2006.01) |
| *A61B 5/0215* | (2006.01) |
| *A61B 5/024* | (2006.01) |
| *G16H 10/20* | (2018.01) |

(52) U.S. Cl.
CPC ........ *A61B 5/02028* (2013.01); *A61B 5/0261* (2013.01); *A61B 5/1102* (2013.01); *A61B 5/26* (2021.01); *A61B 5/282* (2021.01); *A61B 5/332* (2021.01); *A61B 5/4875* (2013.01); *A61B 5/6898* (2013.01); *A61B 5/7264* (2013.01); *A61B 5/7275* (2013.01); *A61B 5/741* (2013.01); *A61B 5/742* (2013.01); *A61B 7/04* (2013.01); *A61B 8/04* (2013.01); *A61B 8/065* (2013.01); *A61B 5/02108* (2013.01); *A61B 5/0215* (2013.01); *A61B 5/02416* (2013.01); *A61B 2560/0214* (2013.01); *A61B 2560/0468* (2013.01); *A61B 2562/0219* (2013.01); *A61B 2562/0271* (2013.01); *A61B 2562/166* (2013.01); *A61B 2576/00* (2013.01); *G16H 10/20* (2018.01)

(58) Field of Classification Search
CPC ..... A61B 5/332; A61B 5/4875; A61B 5/7264; A61B 5/0006; A61B 5/002; A61B 5/0218; A61B 5/0215; A61B 7/04; A61B 2562/0219
See application file for complete search history.

(56) References Cited

U.S. PATENT DOCUMENTS

| | | | |
|---|---|---|---|
| 7,302,290 B2 | 11/2007 | Bauer | |
| 8,348,852 B2 | 1/2013 | Bauer et al. | |
| 8,668,649 B2 | 3/2014 | Zhang et al. | |
| 8,858,443 B2 | 10/2014 | Zhang | |
| 8,979,759 B2 | 3/2015 | Tanaka et al. | |
| 10,362,467 B2 | 7/2019 | Landgraf et al. | |
| 10,806,374 B2 | 10/2020 | Inan et al. | |
| 11,083,403 B1 * | 8/2021 | Peters ................. | A61B 5/0261 |
| 2010/0042008 A1 | 2/2010 | Amitai et al. | |
| 2011/0208540 A1 | 8/2011 | Lord et al. | |
| 2014/0378849 A1 | 12/2014 | Krimsky et al. | |
| 2015/0018660 A1 * | 1/2015 | Thomson ............... | A61B 5/332 |
| | | | 600/393 |
| 2015/0065814 A1 | 3/2015 | Kapoor | |
| 2015/0106020 A1 | 4/2015 | Chung et al. | |
| 2015/0216448 A1 | 8/2015 | Lotan et al. | |
| 2015/0263777 A1 * | 9/2015 | Fraden ................. | H04B 1/3888 |
| | | | 455/575.8 |
| 2017/0119255 A1 | 5/2017 | Mahajan et al. | |
| 2017/0340209 A1 | 11/2017 | Klaassen et al. | |
| 2018/0146911 A1 | 5/2018 | Teicher et al. | |
| 2018/0153476 A1 | 6/2018 | Annoni et al. | |
| 2018/0184915 A1 | 7/2018 | Darbari et al. | |
| 2019/0104238 A1 | 4/2019 | Barros et al. | |
| 2019/0117068 A1 | 4/2019 | Thomson et al. | |
| 2019/0298224 A1 | 10/2019 | Rahman et al. | |
| 2020/0002983 A1 | 1/2020 | Breland | |
| 2020/0008685 A1 | 1/2020 | Stahmann et al. | |
| 2020/0013163 A1 | 1/2020 | Choi | |
| 2020/0029834 A1 | 1/2020 | Tang et al. | |
| 2020/0029837 A1 | 1/2020 | Joudi | |
| 2020/0077917 A1 * | 3/2020 | Sayani ................. | A61B 5/6898 |
| 2020/0288985 A1 * | 9/2020 | Robinson ........... | A61B 5/02125 |
| 2020/0352510 A1 * | 11/2020 | Dhillon ............... | A61B 5/1491 |
| 2021/0161423 A1 * | 6/2021 | Olbrich ............... | A61B 5/0536 |
| 2021/0259560 A1 | 8/2021 | Venkatraman et al. | |
| 2021/0275058 A1 | 9/2021 | Zia et al. | |
| 2021/0345934 A1 * | 11/2021 | Landgraf ............. | A61B 5/6898 |
| 2022/0218256 A1 | 7/2022 | Thiagarajan | |

FOREIGN PATENT DOCUMENTS

| | | |
|---|---|---|
| WO | 2017100188 | 6/2017 |
| WO | 2017103134 | 6/2017 |
| WO | 2018024868 | 2/2018 |
| WO | 2018119316 | 6/2018 |
| WO | 2019199762 | 10/2019 |
| WO | 2020041363 | 2/2020 |
| WO | 2020206075 | 10/2020 |
| WO | 2021188878 | 9/2021 |
| WO | 2022/115228 | 6/2022 |

OTHER PUBLICATIONS

Machine English translation of JP-3652791-B2, Chubachi N, 2005, pp. 1-15 (Year: 2005), (Posted on Feb. 10, 2023 in conjunction with USPTO Office Action of U.S. Appl. No. 17/315,261).

Hou Ka et al: "The Current State of Mobile Phone Apps for Monitoring Heart Rate, Heart Rate Variability, and Atrial Fibrillation: Narrative Review", JMIR Mhealth Uhealth, Feb. 15, 2019 (Feb. 15, 2019), pp. 1-16.

Yang Chenxi et al: "A feasibility study on a low-cost, smartphone-based solution of pulse transit time measurement using cardio-mechanical signals", 2017 IEEE Healthcare Innovations and Point of Care Technologies (HI-POCT), IEEE, Nov. 6, 2017 (Nov. 6, 2017), pp. 93-96.

Yang Chenxi et al: "Pulse Transit Time Measurement Using Seismocardiogram, Photoplethysmogram, and Acoustic Recordings: Evaluation and Comparison", IEEE Journal of Biomedical and Health Informatics, vol. 22, No. 3, May 1, 2018 (May 1, 2018), pp. 733-740.

* cited by examiner

100

185

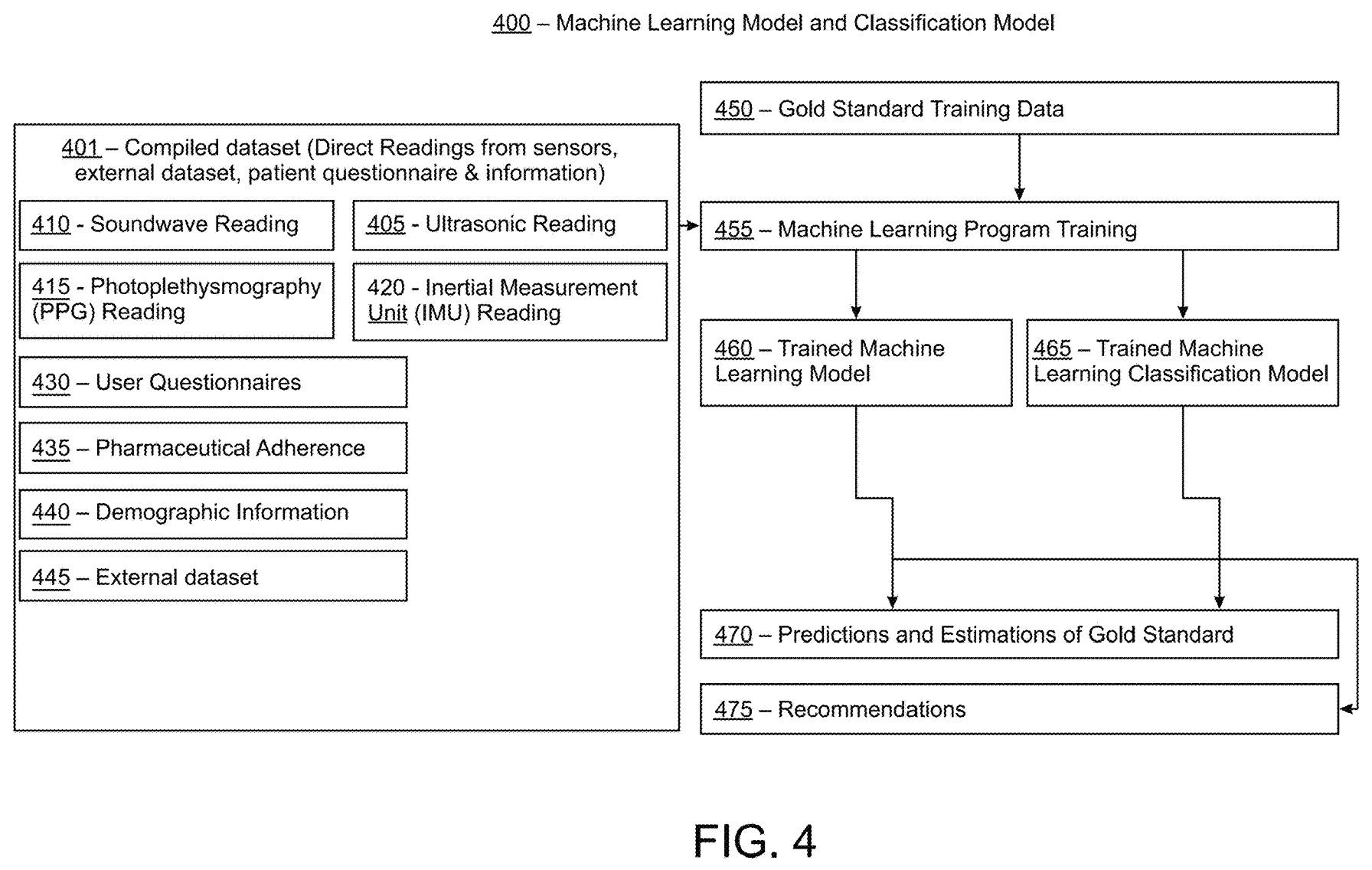

400 – Machine Learning Model and Classification Model

401 – Compiled dataset (Direct Readings from sensors, external dataset, patient questionnaire & information)

410 - Soundwave Reading

405 - Ultrasonic Reading

415 - Photoplethysmography (PPG) Reading

420 - Inertial Measurement Unit (IMU) Reading

430 – User Questionnaires

435 – Pharmaceutical Adherence

440 – Demographic Information

445 – External dataset

450 – Gold Standard Training Data

455 – Machine Learning Program Training

465 – Trained Machine Learning Classification Model

460 – Trained Machine Learning Model

470 – Predictions and Estimations of Gold Standard

475 – Recommendations

FIG. 4

| Recording time (min) | PATIENT 1 | |
| --- | --- | --- |
| | Non-invaise cardiac health data from PPG sensor | Non-invaise cardiac health data from IMU sensor |
| 01:00 | 11 | 25 |
| 01:30 | 33 | 25 |
| 02:00 | 18 | 13 |
| 02:30 | 20 | 26 |
| 03:00 | 14 | 11 |
| 03:30 | 8 | 14 |
| 04:00 | 28 | 23 |
| | PATIENT 2 | |
| 01:00 | 11 | 17 |
| 01:30 | 16 | 20 |
| 02:00 | 18 | 23 |
| 02:30 | 20 | 26 |
| 03:00 | 22 | 29 |
| 03:30 | 24 | 17 |
| 04:00 | 34 | 20 |

| Patient | Gold standard intracardiac pressure (mmHg) |
| --- | --- |
| 1 | 14 |
| 2 | 16 |
| 3 | 22 |
| 4 | 13 |
| 5 | 26 |
| 6 | 37 |
| 7 | 25 |
| 8 | 34 |
| 9 | 22 |
| 10 | 31 |
| 11 | 21 |
| 12 | 11 |
| 13 | 14 |
| 14 | 17 |

560

| Patient | PRESSURE over 25 (mmHg) |
|---|---|
| 1 | 1 |
| 2 | 0 |
| 3 | 0 |
| 4 | 0 |
| 5 | 1 |
| 6 | 1 |
| 7 | 1 |
| 8 | 1 |
| 9 | 0 |
| 10 | 1 |
| 11 | 0 |
| 12 | 0 |
| 13 | 0 |
| 14 | 0 |

Y-variable

FIG. 5C

| Patient | Average of PPG sensor data | Median of PPG sensor data | Generated feature x |
|---|---|---|---|
| 1 | 14 | 25 | y |
| 2 | 16 | 25 | y |
| 3 | 22 | 13 | y |
| 4 | 13 | 26 | y |
| 5 | 26 | 37 | y |
| 6 | 37 | 25 | y |
| 7 | 25 | 34 | y |
| 8 | 34 | 22 | y |
| 9 | 22 | 21 | y |
| 10 | 31 | 11 | y |
| 11 | 21 | 14 | y |
| 12 | 11 | 31 | y |
| 13 | 14 | 31 | y |
| 14 | 14 | 31 | y |

X-variables

| Patient | Gold standard intracardiac pressure (mmHg) |
|---|---|
| 1 | 14 |
| 2 | 16 |
| 3 | 22 |
| 4 | 13 |
| 5 | 26 |
| 6 | 37 |
| 7 | 25 |
| 8 | 34 |
| 9 | 22 |
| 10 | 31 |
| 11 | 21 |
| 12 | 11 |
| 13 | 14 |
| 14 | 17 |

Y-variable

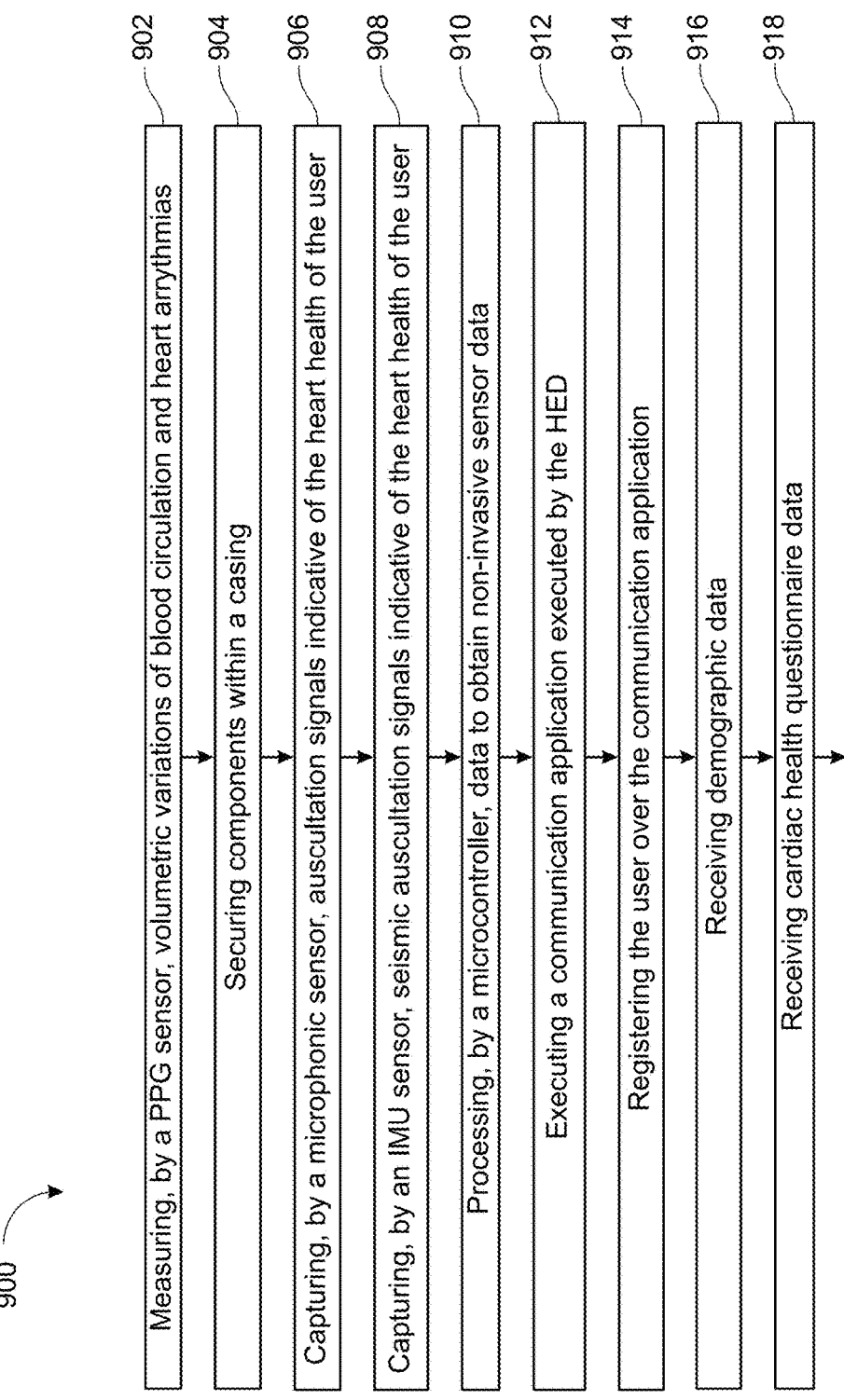

900

902 Measuring, by a PPG sensor, volumetric variations of blood circulation and heart arrythmias 904 Securing components within a casing 906 Capturing, by a microphonic sensor, auscultation signals indicative of the heart health of the user 908 Capturing, by an IMU sensor, seismic auscultation signals indicative of the heart health of the user 910 Processing, by a microcontroller, data to obtain non-invasive sensor data 912 Executing a communication application executed by the HED 914 Registering the user over the communication application 916 Receiving demographic data 918 Receiving cardiac health questionnaire data

FIG. 9 Continued

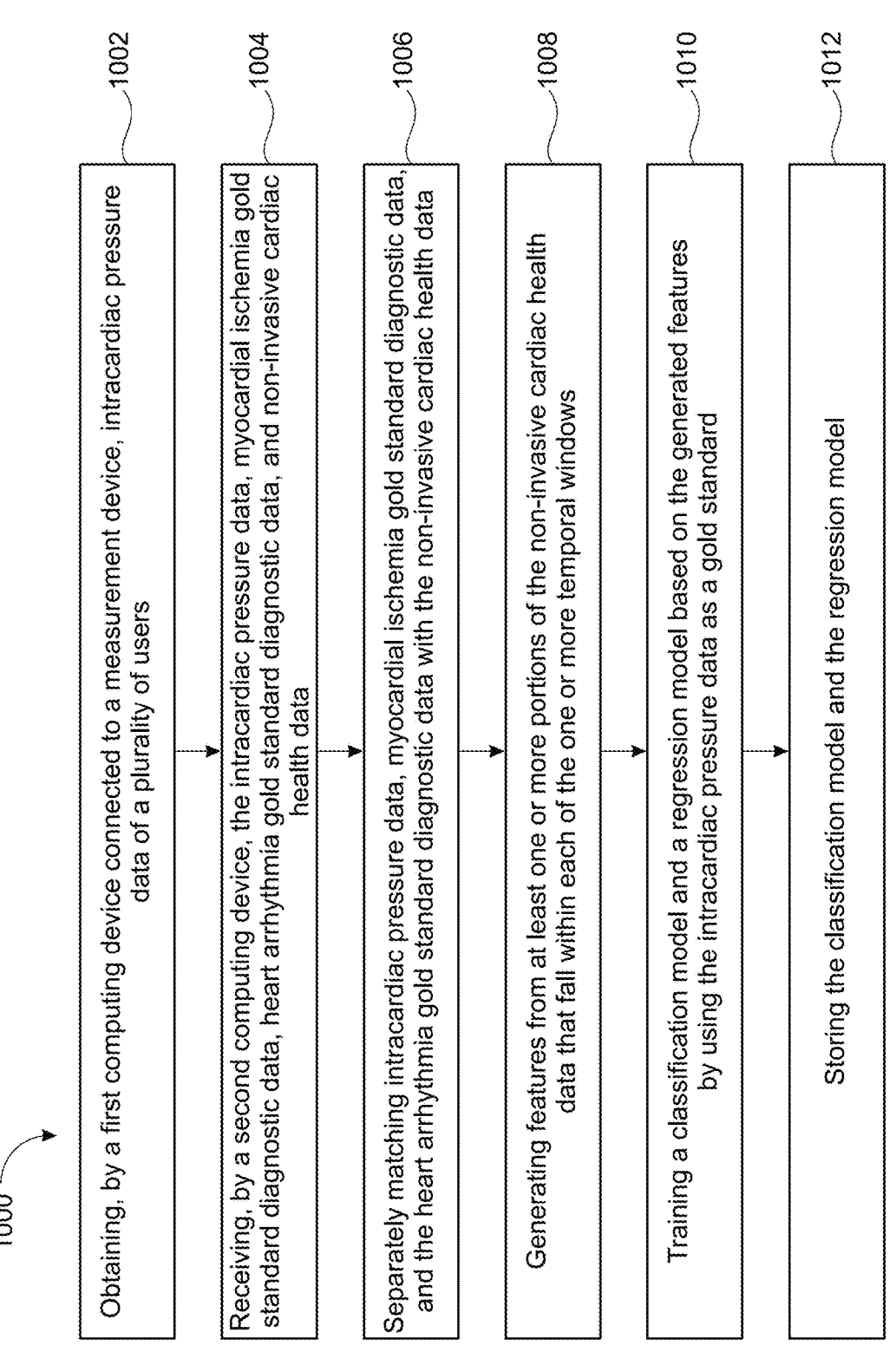

1000

Obtaining, by a first computing device connected to a measurement device, intracardiac pressure data of a plurality of users — 1002

Receiving, by a second computing device, the intracardiac pressure data, myocardial ischemia gold standard diagnostic data, heart arrhythmia gold standard diagnostic data, and non-invasive cardiac health data — 1004

Separately matching intracardiac pressure data, myocardial ischemia gold standard diagnostic data, and the heart arrhythmia gold standard diagnostic data with the non-invasive cardiac health data — 1006

Generating features from at least one or more portions of the non-invasive cardiac health data that fall within each of the one or more temporal windows — 1008

Training a classification model and a regression model based on the generated features by using the intracardiac pressure data as a gold standard — 1010

Storing the classification model and the regression model — 1012

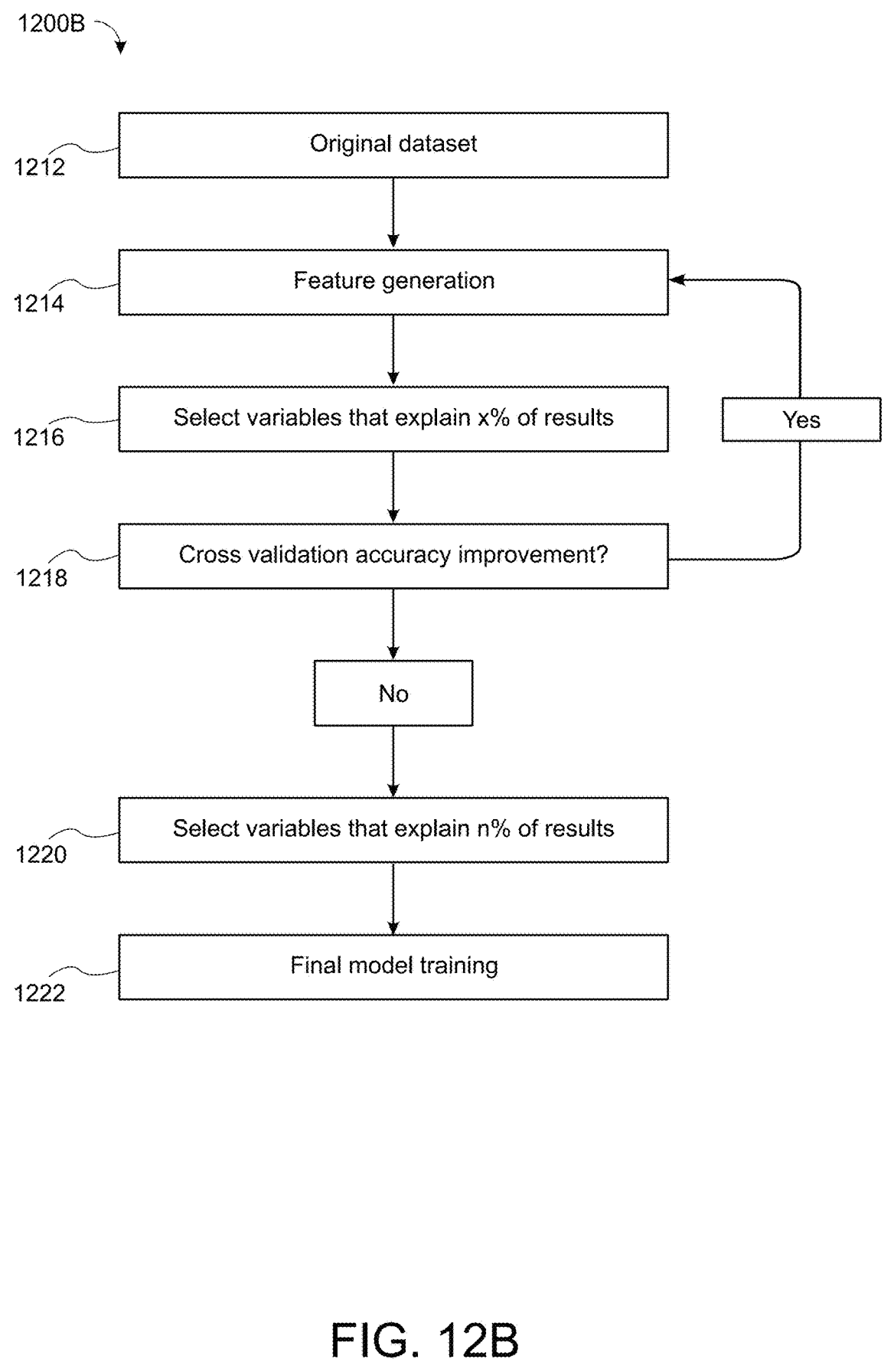

1212 — Original dataset

1214 — Feature generation

1216 — Select variables that explain x% of results

Yes

1218 — Cross validation accuracy improvement?

No

1220 — Select variables that explain n% of results

1222 — Final model training

FIG. 12B

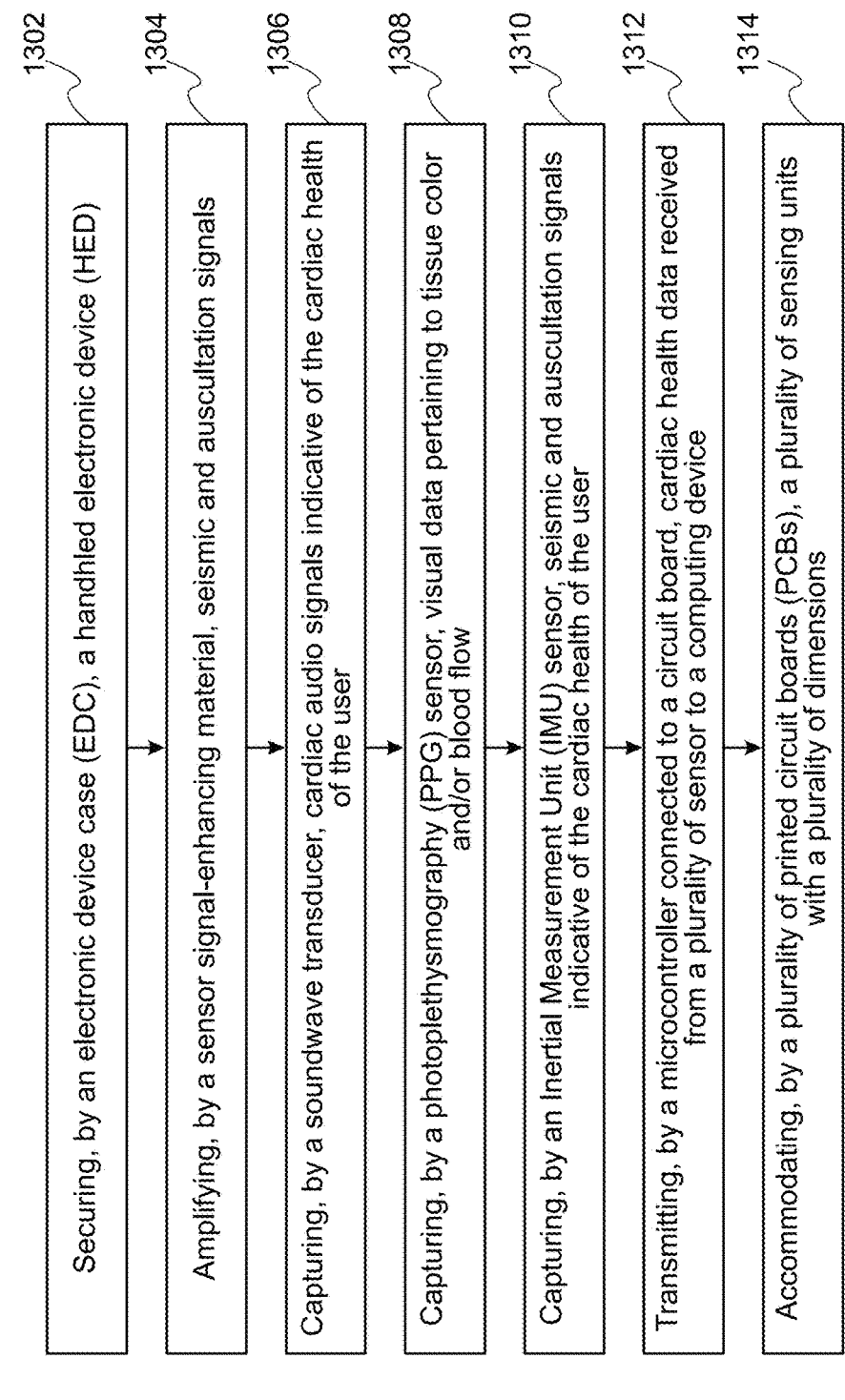

1302

Securing, by an electronic device case (EDC), a handhled electronic device (HED)

1304

Amplifying, by a sensor signal-enhancing material, seismic and auscultation signals

1306

Capturing, by a soundwave transducer, cardiac audio signals indicative of the cardiac health of the user

1308

Capturing, by a photoplethysmography (PPG) sensor, visual data pertaining to tissue color and/or blood flow

1310

Capturing, by an Inertial Measurement Unit (IMU) sensor, seismic and auscultation signals indicative of the cardiac health of the user

1312

Transmitting, by a microcontroller connected to a circuit board, cardiac health data received from a plurality of sensor to a computing device

1314

Accommodating, by a plurality of printed circuit boards (PCBs), a plurality of sensing units with a plurality of dimensions

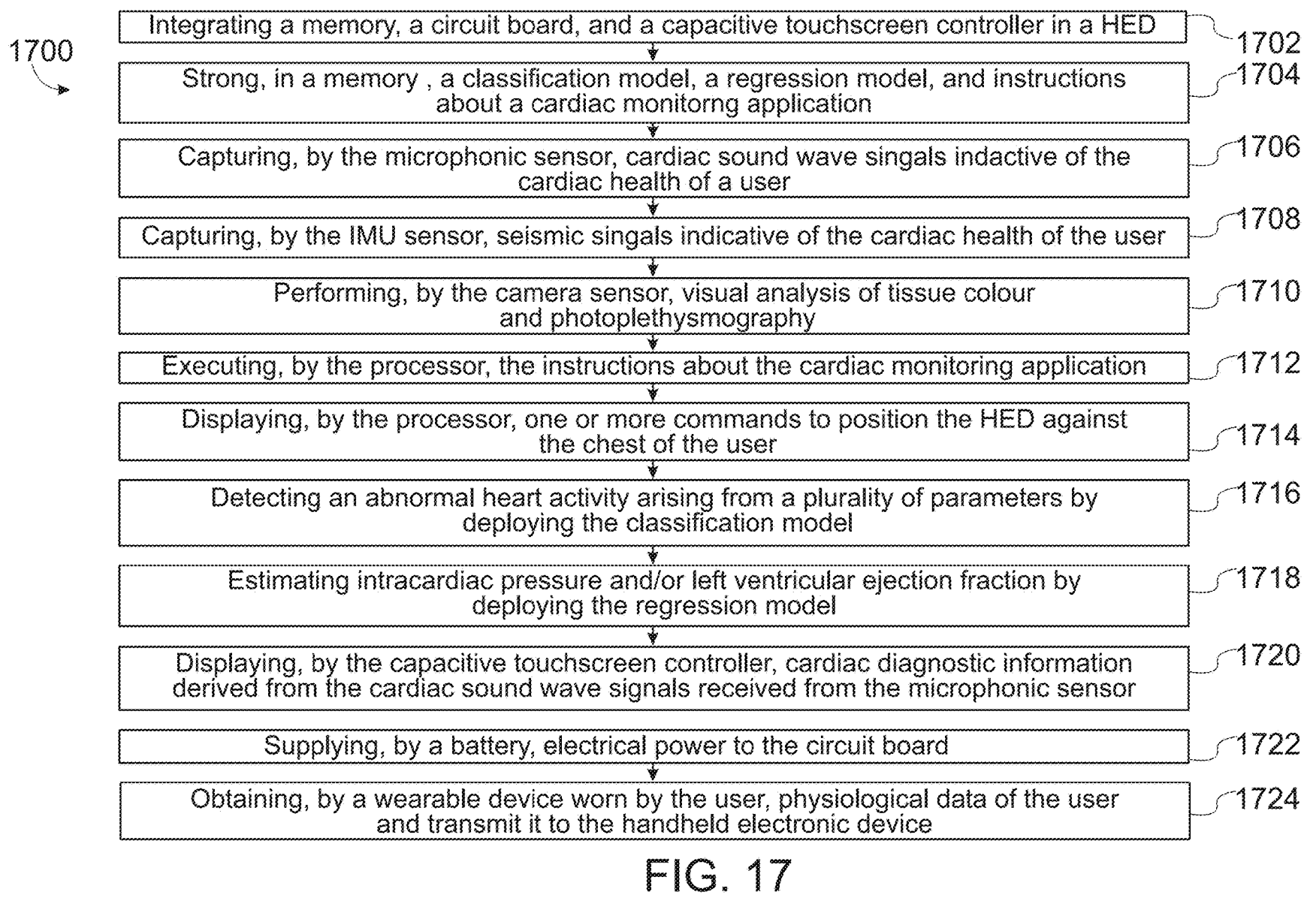

1702 — Integrating a memory, a circuit board, and a capacitive touchscreen controller in a HED 1704 — Strong, in a memory , a classification model, a regression model, and instructions about a cardiac monitoring application 1706 — Capturing, by the microphonic sensor, cardiac sound wave singals inadctive of the cardiac health of a user 1708 — Capturing, by the IMU sensor, seismic singals indicative of the cardiac health of the user 1710 — Performing, by the camera sensor, visual analysis of tissue colour and photoplethysmography 1712 — Executing, by the processor, the instructions about the cardiac monitoring application 1714 — Displaying, by the processor, one or more commands to position the HED against the chest of the user 1716 — Detecting an abnormal heart activity arising from a plurality of parameters by deploying the classification model 1718 — Estimating intracardiac pressure and/or left ventricular ejection fraction by deploying the regression model 1720 — Displaying, by the capacitive touchscreen controller, cardiac diagnostic information derived from the cardiac sound wave signals received from the microphonic sensor 1722 — Supplying, by a battery, electrical power to the circuit board 1724 — Obtaining, by a wearable device worn by the user, physiological data of the user and transmit it to the handheld electronic device

FIG. 17

NON-INVASIVE CARDIAC HEALTH ASSESSMENT SYSTEM AND METHOD FOR TRAINING A MODEL TO ESTIMATE INTRACARDIAC PRESSURE DATA

CROSS-REFERENCE TO RELATED APPLICATIONS

This application is a 371 national stage application of Patent Cooperation Treaty App. No. PCT/EP2021/064940 filed on Jun. 3, 2021, which claims the priority to and benefit of U.S. patent application Ser. No. 16/946,025 filed on Jun. 3, 2020 and U.S. patent application Ser. No. 17/315,261 filed on May 7, 2021. These applications are incorporated by reference in their entireties.

TECHNICAL FIELD

This application is generally directed towards a non-invasive assessment of cardiac health and other conditions. More particularly, but not limited to, machine learning-based systems and methods for training a non-invasive sensor device based on intracardiac pressure data.

BACKGROUND

Heart disease is one of the main causes of death in the world accounting for nearly 25 percent of total deaths annually and is increasing in prevalence, placing a heavy burden on health budgets, and diminishing considerably the quality of life.

Among the challenges facing clinicians is how best to manage heart failure. Appropriate assessment and continuous monitoring of heart diseases are essential for ensuring high-quality patient care. Typically, imaging modalities and electrocardiography (ECG) are used to assess certain aspects of cardiac function, such as atrial fibrillation.

Optimizing medical surveillance and therapy for patients with symptomatic heart failure (HF) and heart disease is important in helping avoid acute decompensations and complications. For many HF patients, worsening cardiac health is assessed by clinical evaluation of body weight or jugular venous pressure. Changes in these parameters however appear late in the process of HF decompensation and are relatively unreliable indicators. Daily measurement of body weight, for example, has low sensitivity for exacerbating HF. Remote monitoring techniques, on the other hand, have shown efficacy in reducing HF re-hospitalizations and mortality rates, particularly when invasive hemodynamic data are acquired.

The release of CardioMEMS, a Food and Drug Administration-approved remote wireless pulmonary artery pressure (PAP) monitoring system, has demonstrated major progress in acute decompensated HF event prevention, showing for the first time, efficacy in reducing heart failure patient hospitalizations by remote monitoring of pressures in the cardiovascular system. Several challenges exist however with these invasive intracardiac pressure monitoring technologies that need to be addressed.

These tools are currently limited to measurement of pulmonary arterial pressure (PAP) and monitoring of the left chambers has not been available for HF patients. Approximately 90% of patients admitted to the hospital for HF have pulmonary congestion related to elevated left atrial pressure (LAP), significantly impacting the efficacy of these tools. In cases where post-capillary pulmonary hypertension is present, PAP sensors are also less indicative of congestion, a common feature of HF with preserved ejection fraction (HFpEF). Left-sided filling pressures may therefore not be accurately estimated in cases of increased pulmonary resistance, which occurs in more than 50% of patients with advanced HF.

Existing solutions can be invasive and there is concern about their cost efficiency. They can also fail to identify precipitating factors of heart failure hospitalizations, for example, mitral regurgitation, myocardial ischemia, heart arrhythmias, uncontrolled hypertension, and the like.

There is thus a long-felt need in the healthcare industry to address these deficiencies and inadequacies. The approaches described in this section are approaches that could be pursued, but these are not necessarily approaches that have been previously conceived or pursued. Therefore, unless otherwise indicated, it should not be assumed that any of the approaches described in this section qualify as prior art merely by virtue of their inclusion in this section.

SUMMARY

Prior art approaches for assessing the cardiac health of patients in real-time can have problems such as portability, effectiveness, accuracy, and cost among other items. Machine learning (ML) in combination with portable devices incorporating non-invasive sensor technologies has the potential to save the lives of current and future heart patients.

Therefore, there is a need for a cardiac health assessment system that leverages a unique combination of sensor technologies and machine learning algorithms to provide an affordable and portable device to assess cardiac health. Additionally, there is a need for a product that can accurately identify several cardiac conditions to facilitate preventive healthcare for heart failure patients. There is therefore a need for a cardiac health assessment system that is non-invasive and can allow for both affordable and effective remote heart failure monitoring.

A need exists for capturing cardiovascular health data for managing heart failure and detecting heart failure at a very early stage in real-time without the need for invasive monitoring. With accurate data, the medical community can prevent repeat hospitalizations and heart attacks. To improve diagnostic, monitoring and treatment capabilities of heart failure patients and address a long-felt need in the healthcare industry, it is desirable to have a system that can quickly and accurately train a non-invasive sensor device based on intracardiac pressure data. The training uses both invasive and non-invasive measurements to learn how the non-invasive readings provide insight into the patient's health condition in the same way of the invasive readings, some of which may reflect the current clinical standard of care. In this way, a patient or a medical professional can obtain clinically relevant diagnostic information using a trained model and non-invasive readings without requiring invasive intervention or measurement devices inserted or implanted in the patient or exposing the patient to additional harmful radiation for imaging. The non-invasive sensor device has a variety of sensors, the output of which can be used for the training, diagnosing, treating, adjusting and recommending.

Described herein are example systems and methods for training a non-invasive sensor device based on intracardiac pressure data.

Some embodiments include an example non-invasive cardiac health assessment system for training a model used with non-invasive sensor device to estimate a patient's heart condition more accurately without invasive measurements of the patient's heart condition. The system has at least one invasive measurement device configured to measure intracardiac pressure data from a plurality of patients, at least one non-invasive sensor device including a plurality of sensors configured to capture non-invasive cardiac health data from the plurality of patients; a computing device comprising a memory storing a plurality of instructions and a processor to execute the plurality of instructions. The processor is configured to match the intracardiac pressure data with the non-invasive cardiac health data from each of the plurality of patients over at least one temporal window corresponding to a specific measurement time period when both the intracardiac pressure data and the non-invasive cardiac health data were measured simultaneously. The processor also generates features from at least one portion of the non-invasive cardiac health data that fall within each of the at least one temporal window, the features being processor-generated manipulations of raw data of the non-invasive cardiac health data. The processor trains a machine learning model to estimate intracardiac pressure data based on the generated features as independent variables and the intracardiac pressure data as a first of at least one dependent variable; and then stores the machine learning model.

Another embodiment is directed to a non-invasive cardiac health assessment system for training a machine learning model to estimate intracardiac pressure data based on a non-invasive sensor device. The system includes a first computing device connected to at least one invasive measurement device to obtain intracardiac pressure data of a plurality of users. It also includes a second computing device to receive the intracardiac pressure data, myocardial ischemia gold standard diagnostic data, heart arrhythmia gold standard diagnostic data, and non-invasive cardiac health data, wherein the second computing device comprises a memory to store a plurality of instructions and a processor to execute the plurality of instructions. The processor is configured to: separately match intracardiac pressure data, myocardial ischemia gold standard diagnostic data, and the heart arrhythmia gold standard diagnostic data with the non-invasive cardiac health data. For each gold standard data, the processor generates features from at least one portion of the non-invasive cardiac health data that fall within each of at least one temporal window; train a classification model and/or a regression machine learning model based on the generated features; and store the machine learning model.

A different embodiment is directed to an example system for training a non-invasive sensor device based on intracardiac pressure data. The system includes a first computing device connected to a measurement device to obtain intracardiac pressure data of a plurality of users; and a second computing device to receive the intracardiac pressure data and non-invasive cardiac health data, wherein the second computing device comprises a memory to store a plurality of instructions and a processor to execute the plurality of instructions. The processor is configured to match intracardiac pressure data with non-invasive cardiac health data, train a neural network model by using the intracardiac pressure data as a gold standard, and store the neural network model.

Another system is described for capturing cardiovascular health data for managing heart failure. This includes handheld electronic device (HED) including an HED processor configured to execute communication application including instructions to register a user over the communication application by receiving at least one credential from the user for providing access to the communication application; receive demographic data pertaining to the user; receive cardiac health questionnaire data from the user; and transmit a final dataset by compiling the demographic data and the cardiac health questionnaire data of the user. The system also includes a computing device including memory and a processor coupled with the memory to execute a plurality of instructions pertaining to the management of heart failure, classification models, and machine learning models to estimate cardiac health; a wearable device communicatively coupled with the handheld electronic device (HED) over a network, the wearable device including a Photoplethysmography (PPG) sensor to measure volumetric variations of blood circulation and heart arrhythmias; and a non-invasive sensor device having a shape adapted to secure a plurality of components within the non-invasive sensor device. The plurality of components include a soundwave transducer configured to capture auscultation signals indicative of cardiac health of a user; an Inertial Measurement Unit (IMU) sensor configured to capture seismic auscultation signals indicative of the cardiac health of the user; and a microcontroller configured to process data received from the PPG sensor, the soundwave transducer, and the IMU sensor to obtain non-invasive sensor data. The computing device receives the non-invasive sensor data and the final dataset from the communication application, stores in the memory the plurality of instructions; and executes the plurality of instructions including receiving, in at least one temporal window, a representation of data from at least one of the following: the PPG sensor, the soundwave transducer, and the IMU sensor; detecting features from at least one portion of the received representations of data that fall within each of the at least one temporal window; and applying a trained machine learning model to the detected features. The trained classification model and the machine learning model are configured to estimate intracardiac pressure of the user, estimate coronary artery disease risk of the user, estimate arrhythmia risk of the user, and adjust at least one medication of the patient based on the estimations of the intracardiac pressure, coronary artery disease risk, and heart arrhythmia risk of the user.

Described herein for the above example systems are several variations including those listed below. Additionally or alternatively, the processor is configured to train a classification machine learning model to estimate myocardial ischemia risk using at least one of a CT-scan recorded by a first of the at least one invasive measurement device or a coronary angiography recorded by a second of the at least one dependent variable configured to estimate myocardial ischemia risk; to estimate blood pressure using an arterial catheterization measurement recorded by a third of the at least one invasive measurement device as a third of the at least one dependent variable; or to estimate a heart arrhythmia risk using electrocardiography as a fourth of the at least one dependent variable; or to estimate a likelihood of pulmonary hypertension using the intracardiac pressure data in a binarized form as a fifth of the at least one dependent variable.

Additionally or alternatively, the processor is configured to train a classification machine learning model and the machine learning model to estimate patient medicine and diet adherence using generated features based on at least one of health questionnaires, demographic data or historical treatment data of the patients.

Additionally or alternatively, the machine learning model is trained to estimate stroke volume measurements obtained from an echocardiogram as a dependent variable.

Additionally or alternatively, the machine learning model is trained to estimate a calcium index obtained from a CT-scan as a dependent variable. A calcium score reflects the total area of calcium deposits and the density of the calcium with a score of zero indicating that no calcium is seen in the heart. It may suggest a low chance of developing a heart attack and the higher the score, the higher a risk of heart disease.

Additionally or alternatively, the computing device records or instructs the plurality of patients, their health care providers, or their agents to input demographic data and health questionnaire data of the plurality of patients.

Additionally or alternatively, the plurality of sensors of the at least one non-invasive sensor device comprises a soundwave transducer, a Photoplethysmography sensor, and an Inertial Measurement Unit sensor.

Additionally or alternatively, the processor generates features based on at least one of sound data by the soundwave transducer and movement data by the inertial measurement sensor of the environment while the non-invasive cardiac health data is being collected from the at least one non-invasive sensor device.

Additionally or alternatively, the at least one invasive measurement device can be a catheter, implanted pressure sensor, and/or an implanted micro-computer. Additionally or alternatively, a second computing device is connected to the at least one invasive measurement device.

Additionally or alternatively, a wearable device worn by the user can be used to obtain physiological data of the user and transmit to a handheld electronic device over a network.

Additionally or alternatively, the physiological data obtained by the wearable device during the collection of intracardiac pressure measurement data is included in the external data.

Additionally or alternatively, a second computing device can be connected to the at least one invasive measurement device.

Additionally or alternatively, the stored classification model and the machine learning model are transferred to the non-invasive sensor device.

Additionally or alternatively, the machine learning model and classification model estimate intracardiac pressure data of a new patient using the at least one non-invasive sensor device.

Additionally or alternatively, the predicted intracardiac pressure data of the new patient is utilized to adjust medical treatment or provide a medical treatment recommendation for the new patient.

Additionally or alternatively, the machine learning model is stored in a second computing device, and the at least one non-invasive sensor device physically connected to or integral with the second computing device.

Additionally or alternatively, the plurality of sensors of the least one non-invasive sensor device include a soundwave transducer, a Photoplethysmography sensor, and an Inertial Measurement Unit sensor, and the non-invasive sensor device is connected to or integral with a handheld electronic device.

Also described herein is an example method for training a non-invasive sensor device based on intracardiac pressure data. The method includes a step of obtaining, by a first computing device connected to a measurement device, intracardiac pressure data of a plurality of users; and a step of receiving, by a second computing device, the intracardiac pressure data, and non-invasive cardiac health data, wherein the second computing device comprises a memory to store a plurality of instructions and a processor to execute the plurality of instructions. The processor is configured to match intracardiac pressure data with non-invasive cardiac health data, generate features from at least one portion of the non-invasive cardiac health data that fall within each of at least one temporal windows, train a machine learning model based on the generated features by using the intracardiac pressure data as a gold standard and store the machine learning model.

Described herein is another example method for training a non-invasive sensor device based on intracardiac pressure data. It includes a first step of obtaining, by a first computing device connected to a measurement device, intracardiac pressure data of a plurality of users. It includes a second step of receiving, by a second computing device, the intracardiac pressure data, myocardial ischemia gold standard diagnostic data, heart arrhythmia gold standard diagnostic data, and non-invasive cardiac health data. The second computing device comprises a memory to store a plurality of instructions and a processor to execute the plurality of instructions. The processor carries out the step of separately matching intracardiac pressure data, myocardial ischemia gold standard diagnostic data, and the heart arrhythmia gold standard diagnostic data with the non-invasive cardiac health data. For each gold standard data, the processor generates features from at least one portion of the non-invasive cardiac health data that fall within each of the at least one temporal window; trains a classification and/or regression machine learning model based on the generated features by using the intracardiac pressure data as a gold standard; and stores the machine learning model.

Described herein is a different example method for training a non-invasive sensor device based on intracardiac pressure data. The method includes obtaining, by a first computing device connected to a measurement device, intracardiac pressure data of a plurality of users; and receiving, by a second computing device, the intracardiac pressure data, and non-invasive cardiac health data. The second computing device comprises a memory to store a plurality of instructions and a processor to execute the plurality of instructions. The processor matches intracardiac pressure data with non-invasive cardiac health data; trains a neural network model by using the intracardiac pressure data as a gold standard; and stores the neural network model.

Described herein is another example method of detecting heart failure using a patient's non-invasive data. The method includes the steps of: providing to a user a non-invasive sensor device including a Photoplethysmography (PPG) sensor, a soundwave transducer, an Inertial Measurement Unit (IMU) sensor, and a microcontroller, and a handheld electronic device (HED); receiving, in at least one temporal window, a representation of data from at least one of the following: the PPG sensor, the soundwave transducer, and the IMU sensor; detecting features from at least one portion of the received representations of data that fall within each of the at least one temporal window; and applying a trained machine learning model to the detected features, wherein the trained classification model and the machine learning model are trained on a data set of a plurality of heart failure patients to estimate intracardiac pressure data using data from the non-invasive sensor device.

Also described herein is an example method for capturing cardiovascular health data for managing heart failure. The method includes providing to a user a non-invasive sensor device including a Photoplethysmography (PPG) sensor, a soundwave transducer, an Inertial Measurement Unit (IMU) sensor, and a microcontroller, and a handheld electronic device (HED) including a communication application; measuring, by the Photoplethysmography (PPG) sensor, volumetric variations of blood circulation and heart arrhythmias; capturing, by the soundwave transducer, auscultation signals indicative of the cardiac health of the user; capturing, by the Inertial Measurement Unit (IMU) sensor, seismic auscultation signals indicative of the cardiac health of the user; processing, by the microcontroller, data received from the PPG sensor, the soundwave transducer, and the IMU sensor to obtain non-invasive sensor data; executing the communication application; registering the user over the communication application by receiving at least one credential from the user for providing access to the communication application; receiving demographic data pertaining to the user; receiving cardiac health questionnaire data from the user; transmitting a final dataset by compiling the demographic data, and the cardiac health questionnaire data of the user; receiving the non-invasive sensor data and the final dataset from the communication application; storing a plurality of instructions pertaining to the management of heart failure, classification models, and machine learning models to estimate cardiac health in a memory; executing the instructions by a processor coupled with the memory; receiving, in at least one temporal window, a representation of data from at least one of the following: the PPG sensor, the soundwave transducer, and the IMU sensor; detecting features from at least one portion of the received representations of data that fall within each of the at least one temporal window; and applying a machine learning model to the detected features. The trained classification model and the machine learning model are configured for: estimating intracardiac pressure of the user; estimating coronary artery disease risk of the user; estimating arrhythmia risk of the user; and adjusting at least one medication of the patient based on the estimations of at least one of intracardiac pressure, coronary artery disease risk, and heart arrhythmia risk of the user.

Described herein for the above example methods are several variations including those listed below. Additionally or alternatively, the methods can include a step of broadcasting by a soundwave transmitter on the HED a plurality of audio instructions for the user to place the handheld electronic device (HED) on the user's body to capture intracardiac pressure data. Additionally or alternatively, the methods can include a step of assisting the user by the handheld electronic device (HED) to respond to a questionnaire about the user's cardiac health. Additionally or alternatively, the methods can include a step of alerting by the communication application the user to perform an exercise and to reduce at least one heart failure risk factor. Additionally or alternatively, the methods can include a step of facilitating by the communication application the user to initiate a telehealth session with a heart failure management professional. Additionally or alternatively, the methods can include a step of training the classification model and the machine learning model to recommend the medications for the patient by using a generative adversarial network. Additionally or alternatively, the methods can include a step of producing an electrocardiogram using electrodes on the wearable device. Additionally or alternatively, the methods can include a step of training a classification model to detect hypertension. Additionally or alternatively, the methods can include a step of training the machine learning model to estimate blood pressure. Additionally or alternatively, the methods can include a step of training the machine learning model to detect non-adherence to medication.

An aspect of the present disclosure relates to another example cardiac health assessment system for use with a handheld electronic device (HED) for assessing the cardiac health of a user. The cardiac health assessment system includes an electronic device case (EDC), and a circuit board. The EDC has a shape adapted to secure the HED with the EDC. The EDC includes a sensor signal-enhancing material to amplify seismic and auscultation signals. The circuit board is configured within the EDC and electrically connected with various sensors. The sensors include a soundwave transducer, a photoplethysmography (PPG) sensor, and an Inertial Measurement Unit (IMU) sensor, and a microcontroller. The soundwave transducer captures cardiac audio signals indicative of the cardiac health of the user. The PPG sensor captures visual data pertaining to tissue colour and/or blood flow. The IMU sensor captures seismic and auscultation signals indicative of the cardiac health of the user. The microcontroller is connected to the circuit board to transmit cardiac health data received from the plurality of sensors to a computing device over a network. The computing device includes a processor to: receive, in one or more temporal windows, a representation of one or more of the IMU sensor, the PPG sensor, and soundwave transducer signal recorded by the EDC; detect features of the IMU sensor, the PPG sensor, and the soundwave transducer from at least one or more portions of the received representations falling within each of the one or more temporal windows; identify patterns of the features of respective sensors from within the one or more portions based on at least a classification model or a regression model; and estimate, based on the regression model, intracardiac pressure and/or left ventricular ejection fraction.

In some embodiments, the soundwave transducer may comprise a plurality of microphonic sensors, ultrasonic transducers and/or infrasonic transducers.

In some embodiments, the EDC is configured to capture cardiac health data of the user when positioned against the chest of the user.

In some embodiments, the circuit board includes a processing unit to execute the instructions pertaining to a cardiac monitoring application. The processing unit is configured to display one or more commands to position the EDC against the chest of the user.

In some embodiments, the classification model is trained to detect abnormal cardiac activity arising from cardiac health conditions comprising coronary artery disease and heart arrhythmias.

In some embodiments, a classification model is trained to detect irregularities in one or more of the following health conditions: hypertension, ischemic cardiomyopathy, aortic stenosis, aortic regurgitation, mitral stenosis, and mitral regurgitation. It is well known that stenosis and regurgitation in a heart may be identified through an echocardiogram, including but not limited to a transoesophageal echocardiogram, to determine irregularities in blood flows through the heart and heart valves resulting from said diseases. Said data may be used as gold standard when training machine learning models.

In some embodiments, the circuit board includes a soundwave transducer to detect abnormal seismic signals and acoustic signals.

In some embodiments, the soundwave transducer transmits soundwaves into the user's body to deflect soundwaves arising from a plurality of physiological processes comprising intracardiac blood pressure and heart movements and return soundwave data to be analysed with the classification model and the regression model.

In some embodiments, the circuit board includes an infrasound transducer for transmitting low-frequency waves into the body of the user to deflect the physiological processes and return wave data to be analysed with the classi-fication model and the regression model.

In some embodiments, the EDC further includes one or more temperature sensors to detect variations in chest skin surface temperature resulting from variations in cardiac volume and/or variations in body fluid levels. Changes in tissue from reduced oxygen levels which often result from heart failure may furthermore cause changes in tissue tem-perature. Reduced blood flow to organs may furthermore cause abnormal changes in temperature, observable on a surface level of a user.

In some embodiments, the cardiac health assessment system further includes a separate handheld electronic device (HED), wirelessly connected with the handheld elec-tronic device and comprising a HED wireless transceiver configured to establish a communication with the computing device to transmit cardiac health data there-between. The processor of the computing device is configured to: detect, based on the classification model, an abnormal cardiac activity arising from a plurality of parameters that includes one or more of hypertension, atrial fibrillation, myocardial ischemia, aortic stenosis, aortic regurgitation, mitral steno-sis, and/or mitral regurgitation; and estimate, based on the regression model, intracardiac pressure and/or left ventricu-lar ejection fraction.

In some embodiments, the cardiac health assessment system further includes a plurality of electrodes. The plu-rality of electrodes includes a first ECG electrode, a second ECG electrode, and a third electrode. The first ECG elec-trode is placed on the outer surface of the EDC. The second ECG electrode and the third electrode are placed on each side of the EDC to facilitate a thumb and fingers of a user to be placed on the EDC having the shape that is adapted to secure the handheld electronic device, wherein the plurality of electrodes are configured to capture data indicative of the cardiac health of the user. The processing unit is configured to transmit data indicative of cardiac function from the handheld electronic device to a clinician computing device over the network for remote diagnostic analysis using machine learning.

In some embodiments, the processor is further configured to detect abnormal pulmonary health activity arising from the plurality of parameters by deploying a pulmonary dis-ease classification model. Abnormal pulmonary health may include but is not limited to chronic obstructive pulmonary disease (COPD) or any type of obstructive lung disease characterized by long-term breathing problems and poor airflow, pulmonary fibrosis, respiratory syndromes, increases in lung fluid levels and/or pulmonary embolism). Lung fluid levels often correlate with intracardiac pressures through the pulmonary arteries. Increased lung fluid levels may be detectable through an increase in density in the thoracic region which may cause noticeable differences in acoustic and/or seismic waveforms. Deteriorations in pul-monary health often correlate with deteriorations in cardiac health including but not limited to acute decompensation.

In some embodiments, the computing device transmits the data processed by the processor to the HED over a network.

In some embodiments, the EDC includes a connector for transmitting data and power between the circuit board and a computing device.

An aspect of the present disclosure relates to an example method for assessing the cardiac health of a user. The method includes a step of securing, by an electronic device case (EDC), a handheld electronic device (HED). The EDC having a shape adapted to secure the HED. The method includes a step of amplifying, by a sensor signal-enhancing material, seismic and auscultation signals. The method includes a step of capturing, by a soundwave transducer, cardiac audio signals indicative of the cardiac health of the user. The method includes a step of capturing, by a photop-lethysmography (PPG) sensor, visual data pertaining to tissue colour and/or blood flow. The method includes a step of capturing, by an Inertial Measurement Unit (IMU) sensor, seismic and auscultation signals indicative of the cardiac health of the user. The method includes a step of transmit-ting, by a microcontroller connected to a circuit board, cardiac health data received from a plurality of sensors to a computing device over a network. The computing device includes a processor configured to receive, in one or more temporal windows, a representation of one or more of the IMU sensor, the PPG sensor, and the soundwave transducer signal recorded by the EDC. The processor is configured to detect features of the IMU sensor, the PPG sensor, and the soundwave transducer from at least one or more portions of the received representations falling within each of the one or more temporal windows. The processor is configured to identify patterns of the features of respective sensors from within the one or more portions based on at least a classi-fication model or a regression model. The processor is configured to estimate, based on the regression model, intracardiac pressure and/or left ventricular ejection fraction.

In some embodiments, the EDC is configured to capture cardiac health data of the user when positioned against the chest of the user. In order to optimise quality of data capture the EDC may be adapted to be positioned along the sternum, with the top of the EDC placed below the collarbone of the user. The EDC may be placed for a duration of 5 seconds or longer to optimise data capture quality. Cardiac health data quality may be optimised when the EDC is placed in accordance with the way that the EDC was positioned during the machine learning model training.

In some embodiments, the EDC is configured to capture cardiac health data of the user when positioned against the back of the user.

In some embodiments, the EDC is configured to capture cardiac health data of the user when positioned against the thoracic cage of the user.

In some embodiments, the EDC is configured to capture cardiac health data of the user when positioned against the leg of the user.

In some embodiments, the EDC is configured to capture cardiac health data of the user when positioned against the arm of the user.

In some embodiments, the circuit board includes a pro-cessing unit to execute the instructions pertaining to a cardiac monitoring application. The processing unit is con-figured to transmit one or more commands to position the EDC against the chest of the user.

In some embodiments, the soundwave transducer trans-mits soundwaves into the user's body to deflect soundwaves arising from a plurality of physiological processes compris-ing intracardiac blood pressure and heart movements and return soundwave data to be analysed with the classification model and the regression model.

In some embodiments, the circuit board includes an infrasound transducer for transmitting low-frequency waves into the body of the user to deflect the physiological pro-cesses and return wave data to be analysed with the classi-fication model and the regression model.

In some embodiments, the processor is further configured to detect abnormal pulmonary health activity arising from the plurality of parameters by deploying a pulmonary dis-ease classification model.

In some embodiments, the computing device transmits the data processed by the processor to the HED over a network. In some embodiments, the EDC includes a connector for transmitting data and power between the circuit board and a computing device.

In some embodiments, the IMU sensor has a full-scale acceleration range of ±2/±4/±8/±16 g and an angular rate range of ±125/±250/±500/±1000/±2000 degrees per second (dps).

In some embodiments, the IMU sensor has a full scale (FS) linear acceleration at ±2 of less than or equal to 0.09 mg/Least Significant bit (LSB). A higher sensitivity IMU sensor may enable a higher likelihood of detecting low frequency seismic energy coming from the heart muscle and/or intracardiac pressure.

In some embodiments, the sound wave transducer has a signal-to-noise ratio of higher than or equal to 64 dB. A higher-signal-to noise ratio may enable the detection of several cardiac artefacts that are less pronounced and may be associated with intracardiac pressure, blood flow in the heart and/or the movement of the heart muscle. A high signal-to-noise ratio may be achieved through a reduction in noise generation. Reducing noise generation may include incorporating high quality sensors and electronic devices, using an electronic architecture with reduced external interference, lowering the temperature of the sensors and taking precautions to prevent noisy environmental conditions from influencing the signal, such as using shielded cable and/or spreading out components on a circuit board.

In some embodiments, the sound wave transducer has a frequency range of 10 Hz 10 kHz. Cardiac soundwave properties often occur at lower frequencies, it is therefore useful to analyse lower frequency soundwave data, particularly in the sub-1000 Hz space. An advantage of the present inventive subject matter is that it provides a cardiac monitoring application that can incorporate reminders, nudges, and notifications to help a heart patient track the risk of heart diseases and worsening heart failure. For example, upon detecting a heightened risk, the user may be prompted to self-evaluate a plurality of lifestyle risk factors, such as stress, lack of exercise, and/or diet and medication adherence. The user may be prompted to adjust the plurality of lifestyle risk factors. For example, to reduce stress the user may engage in mindfulness activities such as meditation and/or massage, to improve exercise the user may be prompted to walk a certain number of steps and/or engage in physical activity such as yoga, to improve diet the user may be prompted to change their diet and/or adhere to their prescribed medicine.

In some embodiments, the user may receive targeted marketing aimed at facilitating the user to acquire certain products and/or services that can help the user resolve a plurality of lifestyle risk factors. For example, the user may be prompted to buy a subscription to a meditation and/or exercise application to help reduce stress and or exercise related risk factors. Another advantage of the present inventive subject matter is that it provides a telehealth mechanism to facilitate the user to interact with a clinician and/or get on a video call with the clinician.

Another advantage of the present inventive subject matter is that the telehealth mechanism allows the user to interact with a medical chatbot to get information and provide feedback. The chatbot may offer personalised recommendations on how to reduce heart failure symptoms based on unique user information, such as the user's intracardiac pressure. The chatbot and/or a healthcare professional that the user is connected to may be specialised in a certain cardiac health area that corresponds to the user's symptoms. For example, if the user is suffering from Heart Failure with Preserved Ejection Fraction (HFpEF), the user may be connected with a healthcare professional via telehealth who is an expert within HFpEF. If the deteriorations in cardiac health of a user is due to a particular cardiac disease, e.g. heart arrhythmia, the user may be connected with a healthcare professional via telehealth who is an expert within heart arrhythmia. An aspect of the present disclosure relates to an example system for training a non-invasive sensor device based on intracardiac pressure data. The system includes a first computing device, a measurement device, and a second computing device. The first computing device is connected to the measurement device to obtain intracardiac pressure data of the users. The second computing device receives the intracardiac pressure data and non-invasive cardiac health data. The second computing device includes a memory to store a plurality of instructions and a processor to execute the plurality of instructions. The processor is configured to match intracardiac pressure data with non-invasive cardiac health data; generate features from at least one or more portions of the non-invasive cardiac health data that fall within each of the one or more temporal windows; train a classification model and a regression model based on the generated features by using the intracardiac pressure data as a gold standard; and store the classification model and the regression model.

In some embodiments, the processor is further configured to train a patient medicine and diet adherence model.

In some embodiments, the classification model and the regression model are trained to estimate stroke volume measurements obtained from an echocardiogram gold standard.

In some embodiments, the measurement device includes a catheter.

In some embodiments, the measurement device includes an implanted pressure sensor.

An aspect of the present disclosure relates to a system for training a non-invasive sensor device based on intracardiac pressure data. The system includes a first computing device, a measurement device, and a second computing device. The first computing device is connected to the measurement device to obtain intracardiac pressure data of a plurality of users. The second computing device receives the intracardiac pressure data, myocardial ischemia gold standard diagnostic data, heart arrhythmia gold standard diagnostic data, and non-invasive cardiac health data. The second computing device includes a memory to store a plurality of instructions and a processor to execute the plurality of instructions. The processor is configured to separately match intracardiac pressure data, myocardial ischemia gold standard diagnostic data, and the heart arrhythmia gold standard diagnostic data with the non-invasive cardiac health data. The processor generates features from at least one or more portions of the non-invasive cardiac health data that fall within each of the one or more temporal windows for each gold standard data. The processor trains a classification model and a regression model based on the generated features by using the intracardiac pressure data as a gold standard for each gold standard data. The processor stores the classification model and the regression model for each gold standard data.

In some embodiments, the non-invasive cardiac health data comes from an environment that corresponds to the intended use environment to ensure robustness when employed across different environments.

In some embodiments, the non-invasive cardiac health data comes from a patient population that corresponds to the intended user patient population to ensure robustness when employed across different patient populations.

In some embodiments, the myocardial ischemia gold standard diagnostic data includes tomography data and/or coronary angiography data.

In some embodiments, the heart arrhythmia gold standard diagnostic data includes ECG data.

In some embodiments, the non-invasive sensor device is configured to be used as a Holter monitor by analysing the presence of heart arrhythmias over an extended period. It is well-known that a plurality of heart diseases, including but not limited to heart arrhythmias, may be silent for long periods of times and may therefore be difficult to detect during short episodes of data collection. It may therefore be desirable to collect cardiac information over longer periods of time.

In some embodiments, the non-invasive sensor device is configured to facilitate long-term wear by connecting to a wearable structure. Said wearable structures may include but is not limited to a vest, a garment, a strap and/or a necklace. Said wearable structures may be adjustable in size to fit any size of electronic devices. The non-invasive sensor device may be configured to facilitate the connection of said wearable structures through a handle and/or connector.

In some embodiments, the wearable structures may comprise a battery to enable long-term monitoring.

In some embodiments, the processor is further configured to train a myocardial ischemia predictive model; a blood pressure estimation model; and a heart arrhythmia predictive model.

In some embodiments, the second computing device facilitates the users to feed demographic data and health questionnaire data of the users.

In some embodiments, the classification model and the regression model receive sound and/or movement data of the environment while the non-invasive cardiac health data is being collected from the non-invasive sensor device.

In some embodiments, the non-invasive sensor device includes but is not limited to a soundwave transducer, a Photoplethysmography (PPG) sensor and an Inertial Measurement Unit (IMU) sensor.

In some embodiments, the measurement device includes a catheter and an implanted sensor.

In some embodiments, the physiological data obtained by the wearable device is transmitted to the second computing device for training the classification model and the regression model.

In some embodiments, the stored classification model and the regression model are transferred to the non-invasive sensor device.

An aspect of the present disclosure relates to a system for training a non-invasive sensor device based on intracardiac pressure data. The system includes a first computing device, a measurement device, and a second computing device. The first computing device is connected to the measurement device to obtain intracardiac pressure data of a plurality of users. The second computing device receives the intracardiac pressure data and non-invasive cardiac health data. The second computing device includes a memory to store a plurality of instructions and a processor to execute the plurality of instructions. The processor is configured to match intracardiac pressure data with non-invasive cardiac health data; train a neural network model by using the intracardiac pressure data as a gold standard; and store the neural network model.

In some embodiments, the processor is further configured to train: a patient medicine and diet adherence model.

In some embodiments, the neural network model is trained to estimate stroke volume measurements obtained from an echocardiogram gold standard.

In some embodiments, the users are segmented based on historical treatment data, wherein the users are a plurality of heart failure patients.

In some embodiments, the users are segmented based on historical treatment data, wherein the users are a plurality of heart disease patients.

In some embodiments, the system includes a computing device to receive sound and/or movement data of the environment while the non-invasive cardiac health data is being collected from the non-invasive sensor device.

In some embodiments, the non-invasive sensor device includes but is not limited to a soundwave transducer, a Photoplethysmography (PPG) sensor, and an Inertial Measurement Unit (IMU) sensor.

In some embodiments, the non-invasive sensor device takes the form of an electronic device case (EDC).

In some embodiments, the electronic device case (EDC) is adaptable to receive a handheld electronic device, wherein the HED includes a display screen to display non-invasive cardiac health data derived from the data processed by the microcontroller.

In some embodiments, the non-invasive sensor device includes a disposable portion that is disposed after use.

In some embodiments, the system includes a separate handheld electronic device (HED), wirelessly connected with the handheld electronic device and comprising a HED wireless transceiver configured to establish a communication with the computing device to transmit cardiac health data there-between. The computing device includes a processor configured to: detect, based on the classification model, an abnormal cardiac activity arising from a plurality of parameters that includes one or more of hypertension, myocardial ischemia, atrial fibrillation, aortic stenosis, aortic regurgitation, mitral stenosis, and/or mitral regurgitation; and estimate, based on the regression model, intracardiac pressure and/or left ventricular ejection fraction and/or blood pressure.

In some embodiments, the system includes a plurality of printed circuit boards (PCBs) to accommodate a plurality of sensors with a plurality of dimensions.

In some embodiments, the non-invasive sensor device includes a connector for transmitting data and power between the circuit board and a computing device.

In some embodiments, the plurality of sensors includes a hydration monitoring sensor configured to compute a hydration metric of a body tissue of the user. A hydration metric of a body tissue can be positively correlated to congestion and/or intracardiac pressures and can be used to estimate heart failure and/or general cardiac health conditions. It is well-known that there exists a basic correlation between an electric resistance of a body and the water content in it. Human body resistance can vary between a few ohms and thousands of ohms depending on the water contents in the body. It is further known that ultrasound velocity in muscle is a linear function of water content and can infer the hydration status of the body. A hydration metric of a body tissue of the user may be computed based on the determined changes in tissue volume and changes in vascular volume within the body tissue of a user.

In some embodiments, the hydration monitoring sensor may comprise a bio-impedance measurement sensor, a sensor configured to gather galvanic skin response data through electrodermal activity (EDA), microfluidic sweat sampling sensor configured to identify sweat electrolyte ion concentrations, electrodes made of an elastic polymer composite that includes conductive silver nanowires, one or more soundwave transducers configured to determine an ultrasound velocity in a muscle and/or other sensors able to collect skin conductance data.

In some embodiments, the measurement device includes an implanted micro-computer.

In some embodiments, the second computing device warns the user of incorrect placement of the device.

In some embodiments, the data obtained by the wearable device during the collection of intracardiac pressure measurement data is included in the external data.

In some embodiments, the non-invasive sensor device may be connected to a step-counter to assess a user's physical activity. It is well-known that rising intracardiac pressures may coincide with heart failure symptoms related to physical exertion including but not limited to shortness of breath, fatigue and/or general physical exhaustion. Said heart failure symptoms may correlate with the daily activity of a patient and may be approximated from a patient's number of steps taken throughout a day. A step-counter may comprise a handheld electronic device, wearable, electronic device with equipped with an inertial measurement unit and/or a manual step-counter configuration.

In some embodiments, physical activity may further be approximated from patterns related to heart rate, heart rate variability and/or vertical distance moved (e.g., the number of stairs/floors that have been travelled throughout a given time-period.)

Said physical activity assessment may be used to estimate the user's cardiac health, including but not limited to intracardiac pressure and/or risk of hospitalization.

In some embodiments, the stored neural network model is transferred to the non-invasive sensor device.

An aspect of the present disclosure relates to a method for training a non-invasive sensor device based on intracardiac pressure data. The method includes a step of obtaining, by a first computing device connected to a measurement device, intracardiac pressure data of a plurality of users. The method includes a step of receiving, by a second computing device, the intracardiac pressure data, and non-invasive cardiac health data. The second computing device includes a memory to store a plurality of instructions and a processor to execute the plurality of instructions. The processor is configured to match intracardiac pressure data with non-invasive cardiac health data; generate features from at least one or more portions of the non-invasive cardiac health data that fall within each of the one or more temporal windows; train a classification model and a regression model based on the generated features by using the intracardiac pressure data as a gold standard; and store the classification model and the regression model.

An aspect of the present disclosure relates to a method for training a non-invasive sensor device based on intracardiac pressure data. The method includes a step of obtaining, by a first computing device connected to a measurement device, intracardiac pressure data of a plurality of users. The method includes a step of receiving, by a second computing device, the intracardiac pressure data, myocardial ischemia gold standard diagnostic data, heart arrhythmia gold standard diagnostic data, and non-invasive cardiac health data. The second computing device includes a memory to store a plurality of instructions and a processor to execute the plurality of instructions. The processor is configured to separately match intracardiac pressure data, myocardial ischemia gold standard diagnostic data, and the heart arrhythmia gold standard diagnostic data with the non-invasive cardiac health data. The processor generates features from at least one or more portions of the non-invasive cardiac health data that fall within each of the one or more temporal windows for each gold standard data. The processor trains a classification model and a regression model based on the generated features by using the intracardiac pressure data as a gold standard for each gold standard data. The processor stores the classification model and the regression model for each gold standard data.

An aspect of the present disclosure relates to a method for training a non-invasive sensor device based on intracardiac pressure data. The method includes a step of obtaining, by a first computing device connected to a measurement device, intracardiac pressure data of a plurality of users. The method includes a step of receiving, by a second computing device, the intracardiac pressure data, and non-invasive cardiac health data. The second computing device includes a memory to store a plurality of instructions and a processor to execute the plurality of instructions. The processor is configured to match intracardiac pressure data with non-invasive cardiac health data; train a neural network model by using the intracardiac pressure data as a gold standard; and store the neural network model.

Systems and methods for capturing cardiovascular health data for managing heart failure are provided, as shown in and/or described in connection with at least one Figure.

One aspect of the present disclosure relates to a system for capturing cardiovascular health data for managing heart failure. The system includes a wearable device, a non-invasive sensor device, a communication application, and a computing device. The wearable device is communicatively coupled with a handheld electronic device (HED) over a network. The wearable device includes a Photoplethysmography (PPG) sensor. The PPG sensor measures volumetric variations of blood circulation and/or heart arrhythmias. The non-invasive sensor device has a shape adapted to secure a plurality of components within the non-invasive sensor device. The components include a soundwave transducer, an Inertial Measurement Unit (IMU) sensor, and a microcontroller. The soundwave transducer captures auscultation signals indicative of the cardiac health of the user. The IMU sensor captures seismic auscultation signals indicative of the cardiac health of the user. The microcontroller processes data received from the PPG sensor, the soundwave transducer, and the IMU sensor to obtain non-invasive sensor data. The communication application is executed by the handheld electronic device (HED) The communication application is configured to register the user over the communication application by receiving at least one credential from the user for providing access to the communication application; receive demographic data pertaining to the user; receive cardiac health questionnaire data from the user; and transmit a final dataset by compiling the demographic data, and the cardiac health questionnaire data of the user. The computing device receives the non-invasive sensor data and the final dataset from the communication application. The computing device includes a memory and a processor. The memory stores a plurality of instructions pertaining to the management of heart failure, classification models, and regression models to estimate cardiac health. The processor is coupled with the memory to execute the instructions. The processor is configured to receive, in one or more temporal windows, a representation of data from one or more of: the PPG sensor, the soundwave transducer, and the IMU sensor; detect features from at least one or more portions of the received representations of data that fall within each of the one or more temporal windows; apply a classification model and a regression model to the detected features. The trained classification model and the regression model are configured to estimate intracardiac pressure of the user; estimate coronary artery disease risk of the user; estimate arrhythmia risk of the user; and adjust one or more medications of the patient based on the estimations of the intracardiac pressure, coronary artery disease risk, and heart arrhythmia risk of the user.

In some embodiments, the HED includes a soundwave transducer to broadcast a plurality of audio instructions to place the handheld electronic device (HED) on the user's body to capture intracardiac pressure data.

In some embodiments, the computing device facilitates the user to respond to a questionnaire about the user's cardiac health.

In some embodiments, the communication application alerts the user to perform an exercise, and to reduce one or more heart failure risk factors.

In some embodiments, the communication application facilitates the user to initiate a telehealth session with a heart failure management professional.

In some embodiments, the classification model and the regression model are trained to recommend the medications for the patient by using a generative adversarial network.

In some embodiments, the wearable device includes electrodes enabling electrocardiography.

In some embodiments, the classification model is trained to detect hypertension.

In some embodiments, the regression model is trained to estimate blood pressure.

In some embodiments, the classification model and the regression model are trained to detect non-adherence to medication.

In some embodiments, the non-invasive sensor device includes a soundwave transceiver and/or a PPG sensor.

An aspect of the present disclosure relates to a method for capturing cardiovascular health data for managing heart failure. The method includes a step of measuring, by a Photoplethysmography (PPG) sensor, volumetric variations of blood circulation and heart arrhythmias. The method includes a step of securing a plurality of components within a non-invasive sensor device. The method includes a step of capturing, by a soundwave transducer, auscultation signals indicative of the cardiac health of the user. The method includes a step of capturing, by an Inertial Measurement Unit (IMU) sensor, seismic auscultation signals indicative of the cardiac health of the user. The method includes a step of processing, by a microcontroller, data received from the PPG sensor, the soundwave transducer, and the IMU sensor to obtain non-invasive sensor data. The method includes a step of executing a communication application executed by the handheld electronic device (HED) The method includes a step of registering the user over the communication application by receiving at least one credential from the user for providing access to the communication application. The method includes a step of receiving demographic data pertaining to the user. The method includes a step of receiving cardiac health questionnaire data from the user. The method includes a step of transmitting a final dataset by compiling the demographic data and the cardiac health questionnaire data of the user. The method includes a step of receiving the non-invasive sensor data and the final dataset from the communication application. The method includes a step of storing a plurality of instructions pertaining to the management of heart failure, classification models, and regression models to estimate cardiac health in a memory. The method includes a step of executing the instructions by a processor coupled with the memory. The method includes a step of receiving, in one or more temporal windows, a representation of data from one or more of: the PPG sensor, the soundwave transducer, and the IMU sensor. The method includes a step of detecting features from at least one or more portions of the received representations of data that fall within each of the one or more temporal windows. The method includes a step of applying a classification model and a regression model to the detected features. The trained classification model and the regression model are configured for: estimating intracardiac pressure of the user; estimating coronary artery disease risk of the user; estimating arrhythmia risk of the user; and adjusting one or more medications of the patient based on the estimations of the intracardiac pressure, coronary artery disease risk, and heart arrhythmia risk of the user.

In some embodiments, the HED includes a soundwave transducer to broadcast a plurality of audio instructions to place the handheld electronic device (HED) on the user's body to capture intracardiac pressure data.

In some embodiments, the computing device facilitates the user to respond to a questionnaire about the user's cardiac health.

In some embodiments, the communication application alerts the user to perform an exercise, and to reduce one or more heart failure risk factors.

In some embodiments, the communication application facilitates the user to initiate a telehealth session with a heart failure management professional.

In some embodiments, the classification model and the regression model are trained to recommend the medications for the patient by using a generative adversarial network.

In some embodiments, the wearable device includes electrodes that enable electrocardiography.

In some embodiments, the classification model is trained to detect hypertension.

In some embodiments, the regression model is trained to estimate blood pressure.

In some embodiments, the classification model and the regression model are trained to detect non-adherence to medication.

Other embodiments and advantages will become readily apparent to those skilled in the art upon viewing the drawings and reading the detailed description hereafter, all without departing from the spirit and the scope of the disclosure. The drawings and detailed descriptions presented are to be regarded as illustrative in nature and not in any way as restrictive.

Other features of the example embodiments will be apparent from the drawings and from the detailed description that follows.

BRIEF DESCRIPTION OF THE DRAWINGS

In the Figures, similar components and/or features may have the same reference label and are optionally relabelled in similar Figures. Further, various components of the same type may be distinguished by following the reference label with a second label that distinguishes among the similar components. If only the first reference label is used in the specification, the description applies to any of the similar components having the same first reference label despite the second reference label's presence or absence in the description.

FIG. 4 illustrates a system-level view of an example machine learning model and classification model.

FIG. 5B depicts an example process of invasive data recorded as a dependent (y) variable (gold standard) and generated features of non-invasive sensor data recorded as an independent (x) variable to be used in training a machine learning model. FIG. 5C depicts the y-variable data of FIG. 5B altered based on an example rule classifying over and under an select amount of blood pressure for a classification model.

FIG. 10 illustrates a flowchart of another example embodiment of a cardiac health assessment method for use with a handheld electronic device.

FIG. 12B is a flowchart of an example method of performing a reiterative process by the machine learning model.

FIG. 13 illustrates a flowchart of an example method for assessing the cardiac health of a user.

FIG. 17 illustrates a flowchart of the method for cardiac health assessment, in accordance with embodiments of the claimed subject matter.

DETAILED DESCRIPTION

Figure 1A:
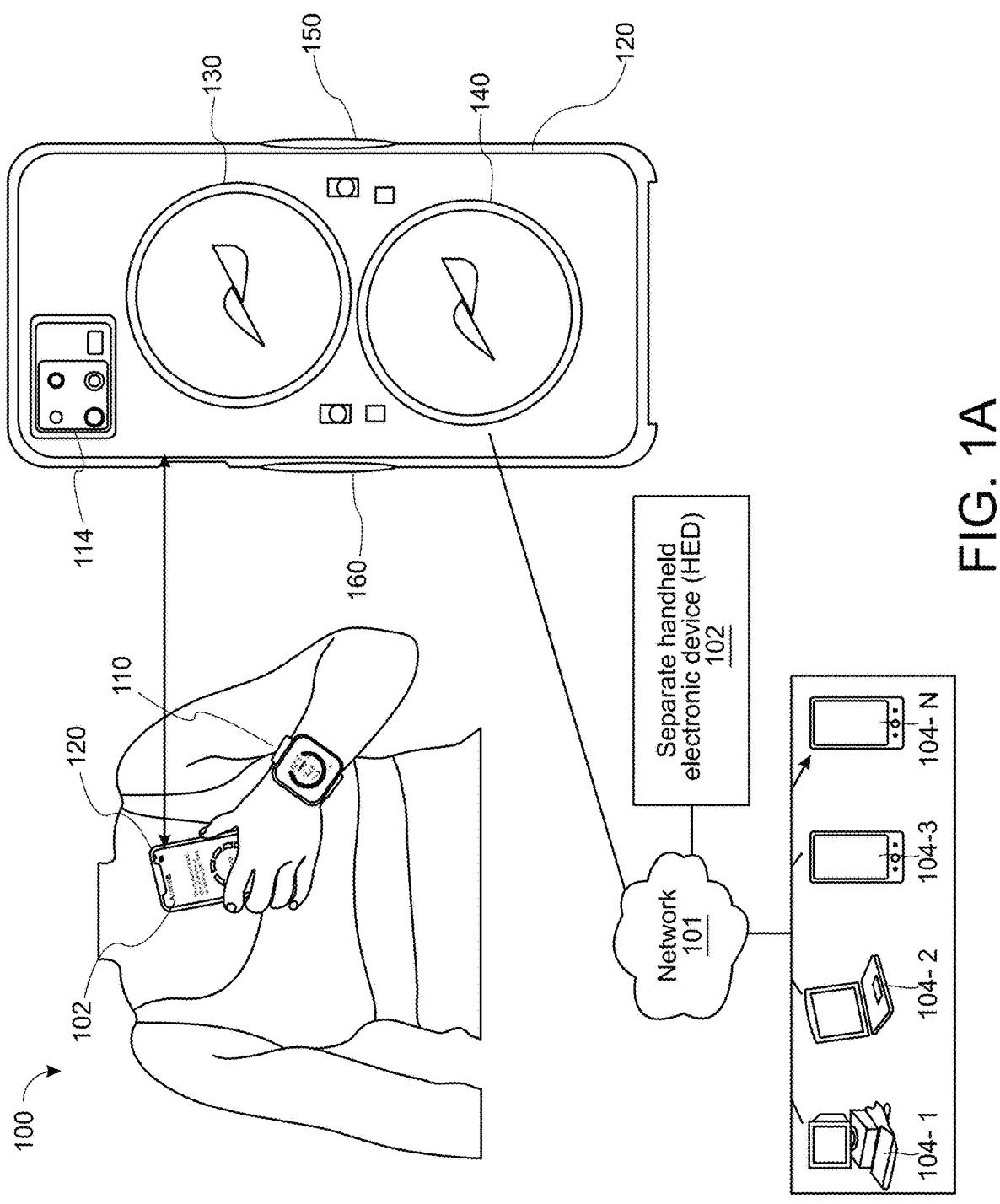
FIG. 1A illustrates a perspective view of an example system including a non-invasive sensor device, a handheld electronic device and a wearable device used by a patient.

The present description is best understood with reference to the detailed Figures and description set forth herein. Various embodiments of the present system and method have been discussed with reference to the Figures. Those skilled in the art will readily appreciate that the detailed description provided herein with respect to the Figures is merely for explanatory purposes, as the present systems and methods may extend beyond the described embodiments. For instance, the teachings presented, and the needs of a particular application, may yield multiple alternative and suitable approaches to implement the functionality of any detail of the present systems and methods described herein. Any approach to implement the present system and method may extend beyond certain implementation choices in the embodiments herein.

A benefit of the systems and methods herein is that, with only smart phone or other handheld device near a patient, the patient or his or her medical providers can access and/or apply the models. Through cloud computing or local/networked storage, one or more processors can implement the model using the newest data from the patient. In some cases, the models can be used on the same patients on which the model was trained and the newest sensed non-invasive data. In other cases, the models can be applied to never tested patients.

The example systems and methods herein benefit patients in that they can be non-invasive and affordable. In addition, features of some embodiments enable ease to use such as not requiring an extra battery in the non-invasive sensor device to charge, the non-invasive sensor device connecting easily to a smartphone, and an intuitive user interface through smartphone app.

Enabling remote care has the benefit of reducing the need for patients to visit hospital. This reduces the need for valuable hospital resources to be allocated towards these patients and reduces the exposure of these at-risk patients to hospital-acquired diseases and/or infections.

The systems and methods herein benefit doctors and other healthcare providers by providing increased information about patient's health so that they are better able to manage the patient, software updates to new disease areas and monitoring capabilities possible through smartphone/app.

The example systems and methods herein benefit insurers by reducing heart failure re-hospitalizations and mortality rates.

The example systems and methods herein benefit pharmaceutical companies in that affordable and non-invasive intracardiac pressure monitoring can enable precision-based medical research and clinical trials to be carried out for heart failure medicine and pulmonary hypertension.

The example systems and methods herein benefit hospitals by minimizing strain on hospital systems through preventing or reducing heart attacks and other heart conditions.

Another advantage of the example systems and methods is that they utilize artificial intelligence and machine learning based algorithms to capture cardiovascular health data for managing heart failure.

Another advantage of the example systems and methods is that they can provide or utilize a wearable device that detects heart failure at early stage in real-time.

Another advantage of the example systems and methods is that they provide a computer-implemented method and system that can continuously track the heart's health of the patient.

Another advantage of the example systems and methods is that they can utilize a data-driven approach to provide robustness across patient cohorts in terms of objectivity and interpretability and may furthermore not be prone to environmental circumstances of clinical settings which may interfere with the communicative process between a clinician and a patient.

Before discussing the methods, some example systems and their hardware configurations and usage will be discussed. (Method steps can be inferred from the discussion.) FIG. 1A illustrates a perspective view of the various components of an example cardiac health assessment system for use with a patient 100 including a computing device (in the form of handheld electronic device 102), a non-invasive sensor device 120 (in the form of an electronic device case in this example), and wearable device 110 (in the form of a smartwatch in this example). The example systems, methods, and apparatuses described herein can use one or more devices with a combination of non-invasive sensors amongst the devices. Not shown here but shown in later Figures are an optional second computing device and invasive measuring device.

The handheld electronic device 102, which will be discussed in greater detail below, has a display 109 that can display a user interface of a software application 185. The display is optionally a touch screen. The handheld computing device 102 is something that could be patient-facing or used by a medical care provider such as a smartphone, mobile, tablet, iPad, laptop, etc. In some embodiments, this device can operate with typical hardware components of user devices including (not shown) a camera 107, display 109, processor 106, battery 105, and microphone 103. The handheld electronic device 102 presents intracardiac pressure data, the name of the user, demographic data of the user, and periodical intracardiac pressure data of the user through a mobile application 185. In some embodiments, the mobile application 185 is executable on the patient-facing computing device 102 and implemented on one or more operating systems such as Android®, iOS®, Windows®, etc. The system 100 requires a user to register on the mobile application 185 by feeding the personal credentials of the user. Examples of the personal credentials including but not limited to a username, password, age, gender, phone number, email address, location, etc. Further, the user is prompted to enter his/her data such as gender, ethnicity, weight, height, and previous medical history. While a handheld device is consistent with the convenience benefit of the system and methods herein including a device being commonly owned and found on patients, equivalent computing devices might have the same function while taking on a different non-handheld form such as a patient bed-side device.

The non-invasive sensor device 120 a plurality of electrodes 140, 150, and 160, and a circuit board 210 (shown in FIG. 2) inside a sensor compartment covered by material 130. The non-invasive sensor device 120 in this example embodiment, has a shape of a phone case adapted to secure the handheld electronic device 102, a smart phone, to the non-invasive sensor device 120 while also fitting the plurality of sensors. The shape of the non-invasive sensor device 120 can easily be adapted for other shapes and devices. In various embodiments, the non-invasive sensor device 120 can be integral with or coupled through mechanical or other attachment with the handheld electronic computing device 102 such as a smartphone, mobile, tablet, iPad, laptop, etc. Found on the non-invasive sensor devices in this embodiment are electrodes including a first ECG electrode 140, a second ECG electrode 150, and a third electrode 160. The first ECG electrode 140 is placed on an outer surface of the non-invasive sensor device 120. The second ECG electrode 150 and the third electrode 160 are placed respectively on each side of the non-invasive sensor device 120 to facilitate a thumb and fingers of a user to be placed on the handheld electronic device 102. The electrodes 140, 150, and 160 are configured to capture data indicative of the cardiac health of the user.

Figure 1B:
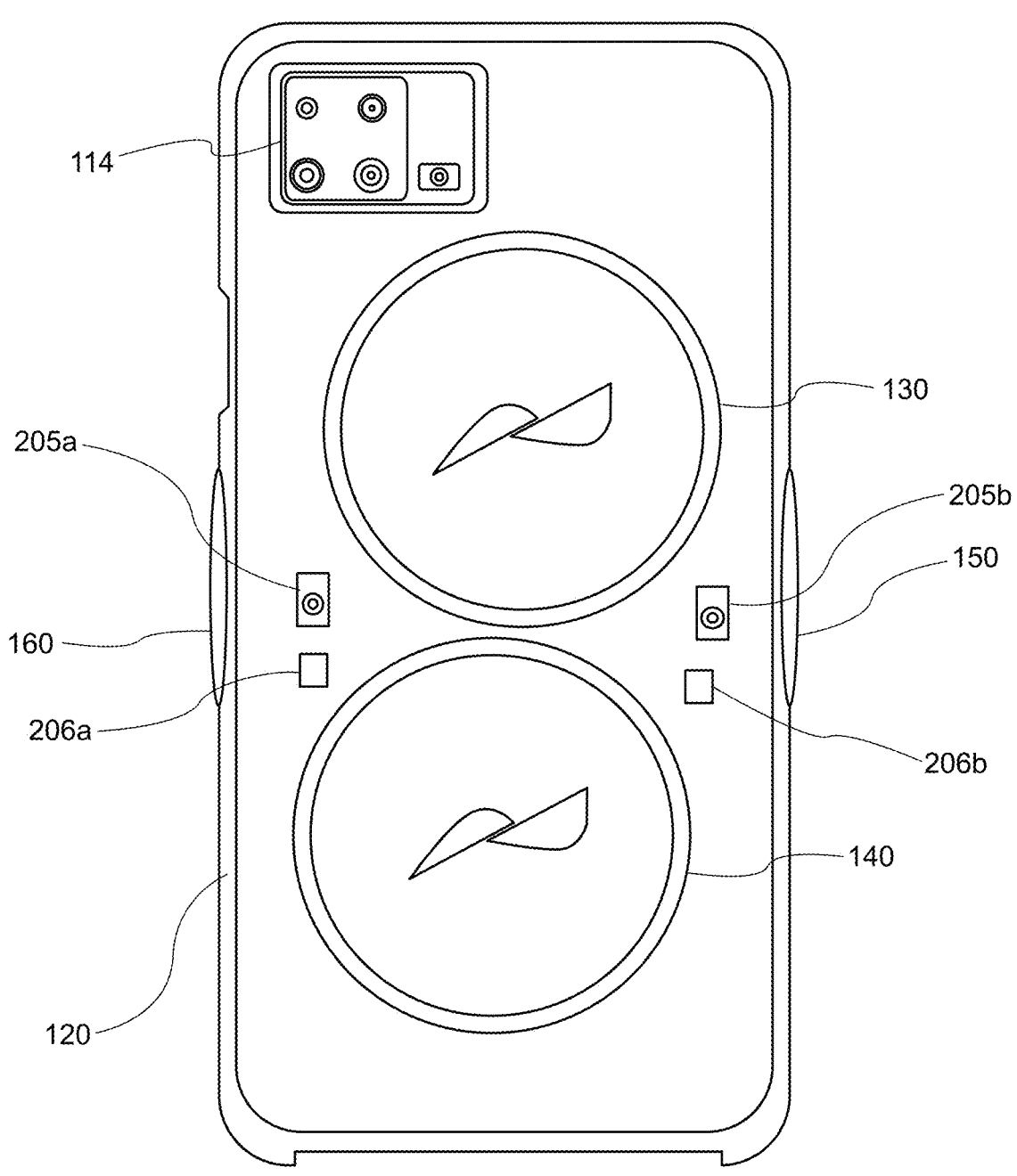
FIG. 1B depicts an example non-invasive sensor device in the form of a smartphone case.
Figure 1C:
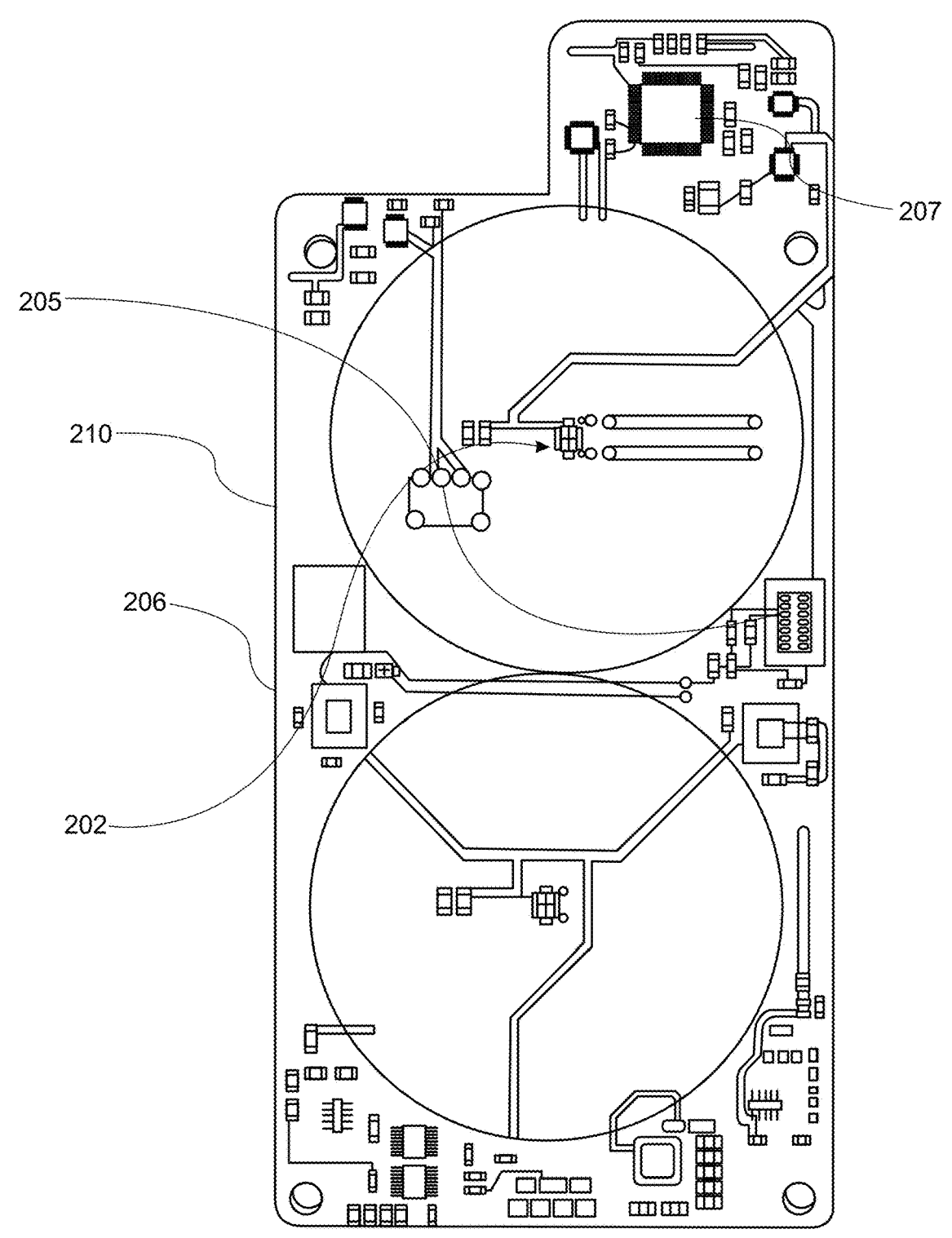
FIG. 1C depicts an example computing device in the form of a handheld electronic device running a software application with a user interface useful for the patient or a health care provider.
Figure 1D:
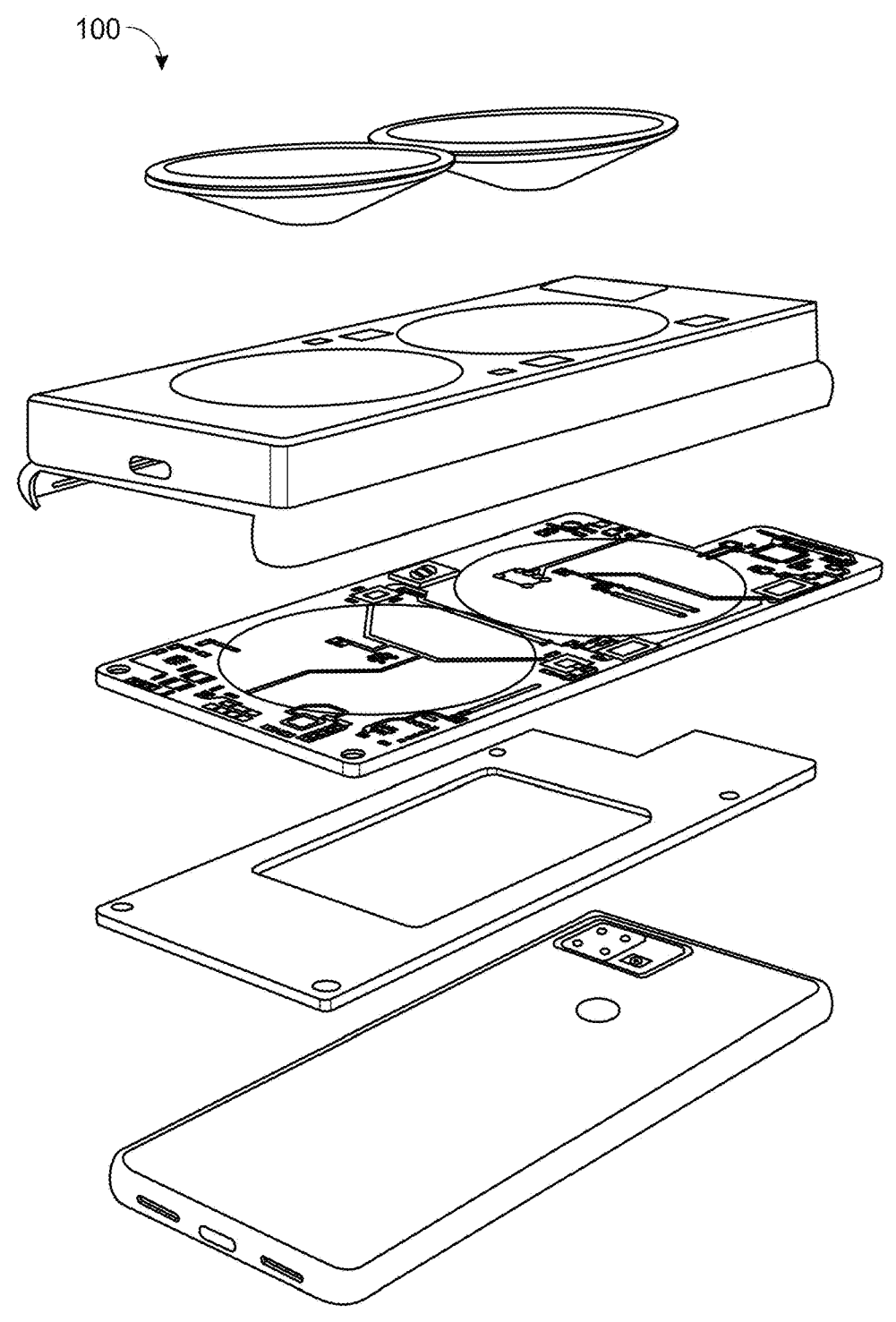
FIG. 1D illustrates an exploded perspective view of the example non-invasive sensor device.
Figure 1E:
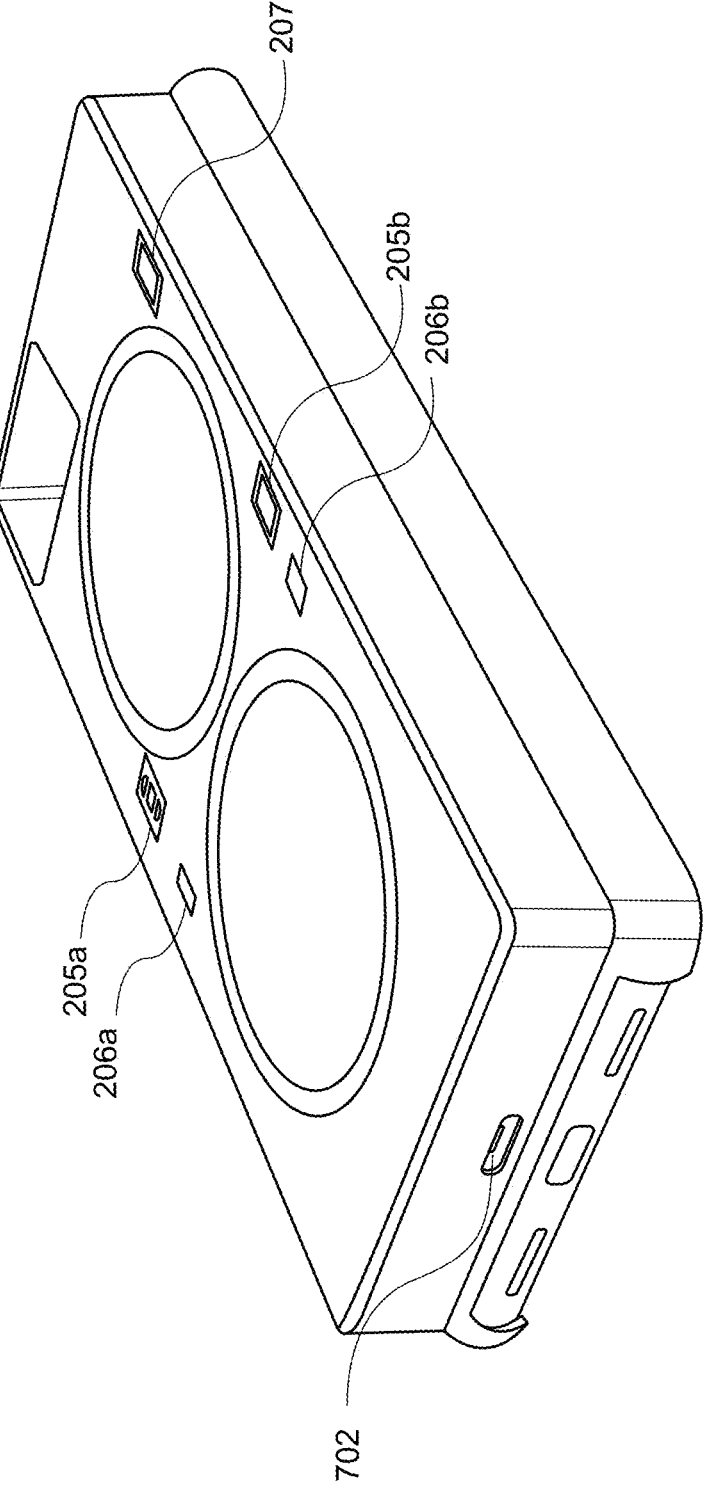
FIG. 1E depicts a perspective view of the example non-invasive sensor device.
Figure 2:
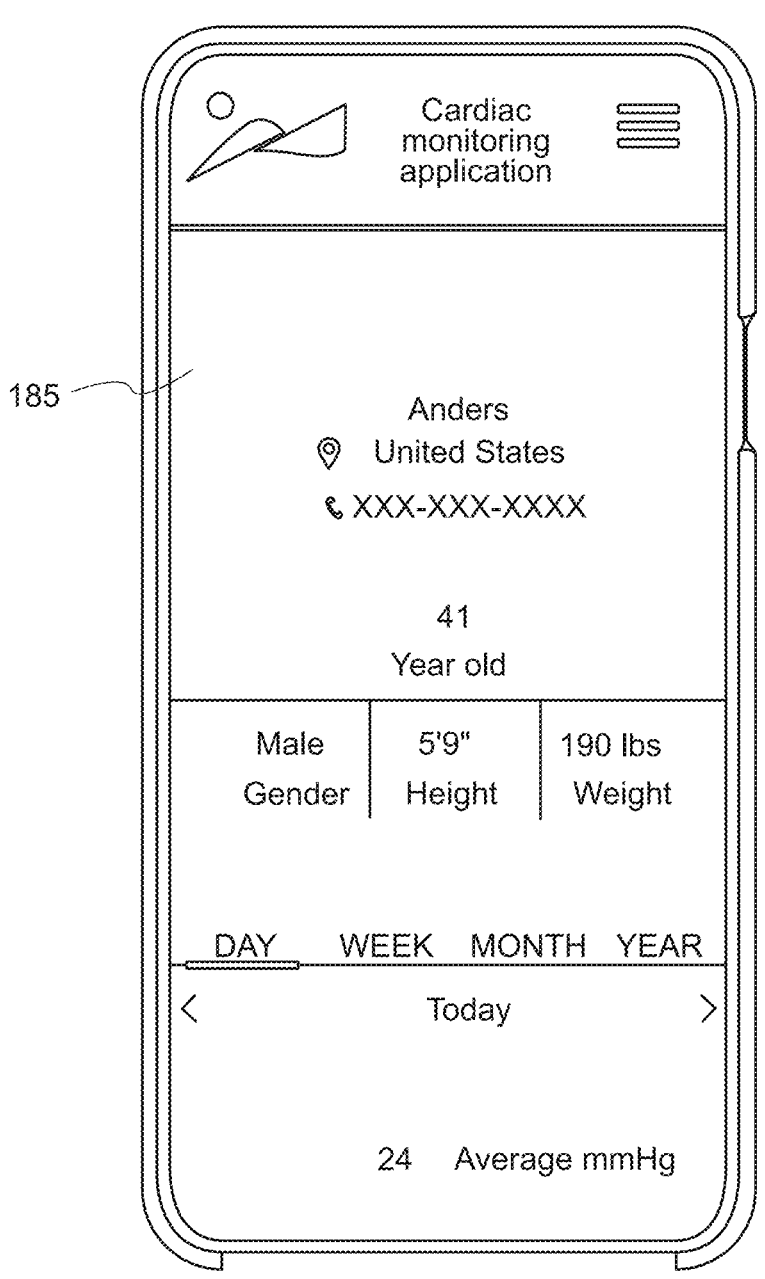
FIG. 2 illustrates an example user interface of the handheld electronic device of FIG. 1A.

FIG. 2 is explained in conjunction with FIG. 1 to provide more detail about the non-invasive sensor device 120 of FIG. 1. FIG. 2 illustrates an exploded view of the various components of the example non-invasive sensor device 120. The circuit board 210 is disposed within the non-invasive sensor device 120 and electrically connected with the plurality of electrodes 140, 150 and 160. The circuit board 210 includes a soundwave transducer 202, an Inertial Measurement Unit (IMU) sensor 206, and a microcontroller. In one embodiment, the non-invasive sensor device 120 is equipped with an ultrasound sensor. In one embodiment, the non-invasive sensor device 120 is equipped with an Photoplethysmography (PPG) sensor 205. In another embodiment, the non-invasive sensor device 120 includes a heat-sensing camera and/or temperature sensor 207 to detect variations in chest skin surface temperature resulting from a plurality of cardiac changes including but not limited to variations in cardiac volume and/or variations in body fluid levels. The microcontroller transmits cardiac health data received from the plurality of electrodes 140, 150, and 160 and the various sensors to at least one of the handheld electronic device 102 or another computing device 302 such as a server, cloud device, workstation, etc. In an example embodiment, the non-invasive sensor device 120 includes a battery (not shown) configured to supply electrical power to the circuit board 210, wherein the battery may receive power supply from an external source. The non-invasive sensor device 120 may connect through its optional power module 112 to a power source 105 of the handheld electronic device 102 through a power cable (not shown) so as to not require the space for a battery and enable a smaller form factor for the phone case form. Additionally, or alternatively, it can have a connection to a wall outlet.

The plurality of sensors on the non-invasive sensor device 120 have a variety of functions used to assess the health of the patient. The soundwave transducer 202 captures cardiac audio signals indicative of the cardiac health of the user. The signal-enhancing material 130 enhances the cardiac audio signals captured by the soundwave transducer 202. In some embodiments, the electrode 140 may further include a signal-enhancing material 130 and a soundwave transducer 202. In some embodiments, signal-enhancing material 130 includes an enhancer unit such as a bell-like object to amplify low-frequency auscultation signals pertaining to the cardiac audio signals. In some embodiments, the signal-enhancing material 130 may be configured as a tube structure to enhance low-frequency sounds. The tube structure may look like the bell used in a regular stethoscope (instead of a diaphragm). The Inertial Measurement Unit (IMU) sensors 206a, and 206b capture seismic and auscultation signals indicative of the cardiac health of the user. The microcontroller 208 is connected to the circuit board 210 to transmit cardiac health data received from the plurality of sensors to one or more computing devices 104-1, 104-2, 104-3, and 104-N over a network 106. Examples of computing devices including but are not limited to a smartphone, mobile, tablet, iPad, laptop, a server, cloud device, a workstation, etc. The computing devices 104 include a processor 113 to: receive, in one or more temporal windows, a representation of one or more of the IMU sensors 206a, and 206b, the PPG sensors 205a, and 205b, and soundwave transducer 202 signal recorded by the non-invasive sensor device 120; detect features of the IMU sensors 206a, and 206b, the PPG sensors 205a, and 205b, and the soundwave transducer 202 from at least one or more portions of the received representations falling within each of the one or more temporal windows; identify patterns of the features of respective sensors from within the one or more portions based on at least a classification model or a regression model; and estimate, based on the regression model, intracardiac pressure and/or left ventricular ejection fraction. The non-invasive sensor device includes sensor signal-enhancing material 130 to amplify seismic and acoustic auscultation signals. Examples of the sensor signal-enhancing material 130 may include but is not limited to sound absorbers made from porous materials, micro-perforated plates, micro-perforated panel absorbers backed with mechanical impedance plates where the backed cavity is limited, and/or piezoelectric material. In some embodiments, the soundwave transducer 202 may be integral with a piezoelectric structure as part of a piezoelectric based electronic stethoscope.

In some embodiments, the non-invasive sensor device 120 includes a lens 114 configured to envelop the built-in camera 107 of the handheld electronic device 102. In one embodiment, the lens is configured to block external light when the HED shines a light onto the skin of the user that is used to record one or more images thereof, wherein the one or more images are analysed based on machine learning for providing insights into the cardiac health of the user. This allows external light to be blocked out while the handheld electronic device 102 shines a light into the skin of the patient and simultaneously records video and/or obtains images thereof. Based on differences in tissue colour resulting from this procedure and applying image recognition machine learning models to such pictures may provide insights into cardiac conditions. Increased left atrial pressure is for example known to be correlated with left atrial volume. Excess blood pressure present in various parts of the cardiac system, may cause detectable differences in tissue colour. Such videos and/or images may furthermore uncover micro perturbations in the flow of blood that may be indicative of certain cardiac conditions such as elevated cardiac pressure. This data correlates to PPG sensor data and may be integrated and analysed with the non-invasive sensor dataset. In some embodiments, the cardiac health assessment may include a flash for illuminating skin tissue during image acquisition by the camera. The camera sensor may include one or more lights that can emit one or more flashes of light that can be directed to the patient's skin. The colour of the flash may be adjusted according to the patient's tissue colour to optimize light penetration and to illuminate certain physiological properties. For example, in some embodiments, certain skin colours may require different light wavelengths to enable visualization and certain physiological properties. In some embodiments, visualizing veins may require a particular light of flash to optimize illumination.

The soundwave transducer captures auscultation signals indicative of the cardiac health of the patient 100. The IMU sensor captures seismic auscultation signals indicative of the cardiac health of the patient 100. The microcontroller processes data received from the PPG sensor, the soundwave transducer, and the IMU sensor to obtain non-invasive sensor data. The communication application is executed by the handheld electronic device (HED).

Wearable device 110 can complement the functionality of non-invasive sensor device 120. Examples of the wearable device 110 include but are not limited to a smartwatch, smart jewellery, wristbands, watches, body-mounted sensors that monitor and transmit biological data for healthcare purposes, fitness trackers, wristbands that monitor physical activity and vital signs. The example wearable device 110 includes a Photoplethysmography (PPG) sensor 124 (different from the PPG sensor of non-invasive sensor device 120). The PPG sensor 124 measures volumetric variations of blood circulation and can be used to detect heart arrhythmias by detecting abnormalities in these volumetric variation measurements. In some embodiments, intracardiac pressure or coronary artery disease, or heart arrhythmia are estimated by the system by collecting data about the patient's health and data from the patient using the components of the non-invasive sensor device 120 and/or wearable device 110, as further discussed below in the context of FIG. 9. Heart arrhythmias are easily detectable by PPG and correlate positively with heart failure, congestion and intracardiac pressures. Integrating a heart arrhythmia estimation in a dataset with non-invasive sensor data collected by the non-invasive sensor device 120 allows for better segmentation of different patient groups. The simultaneous collection of PPG data from the arm (via the wearable device) and PPG data from the chest (via the non-invasive sensor device) of a user can further allow for a comparison between physiological cardiac artefacts of different regions of the body. Differences between these artefacts may point to cardiac irregularities, such as high intracardiac pressures. Using more than one PPG sensor further allows to identify common data noise which may improve the ability of data analysis methods to remove such data noise from the dataset that is used to train the machine learning models.

Figure 3:
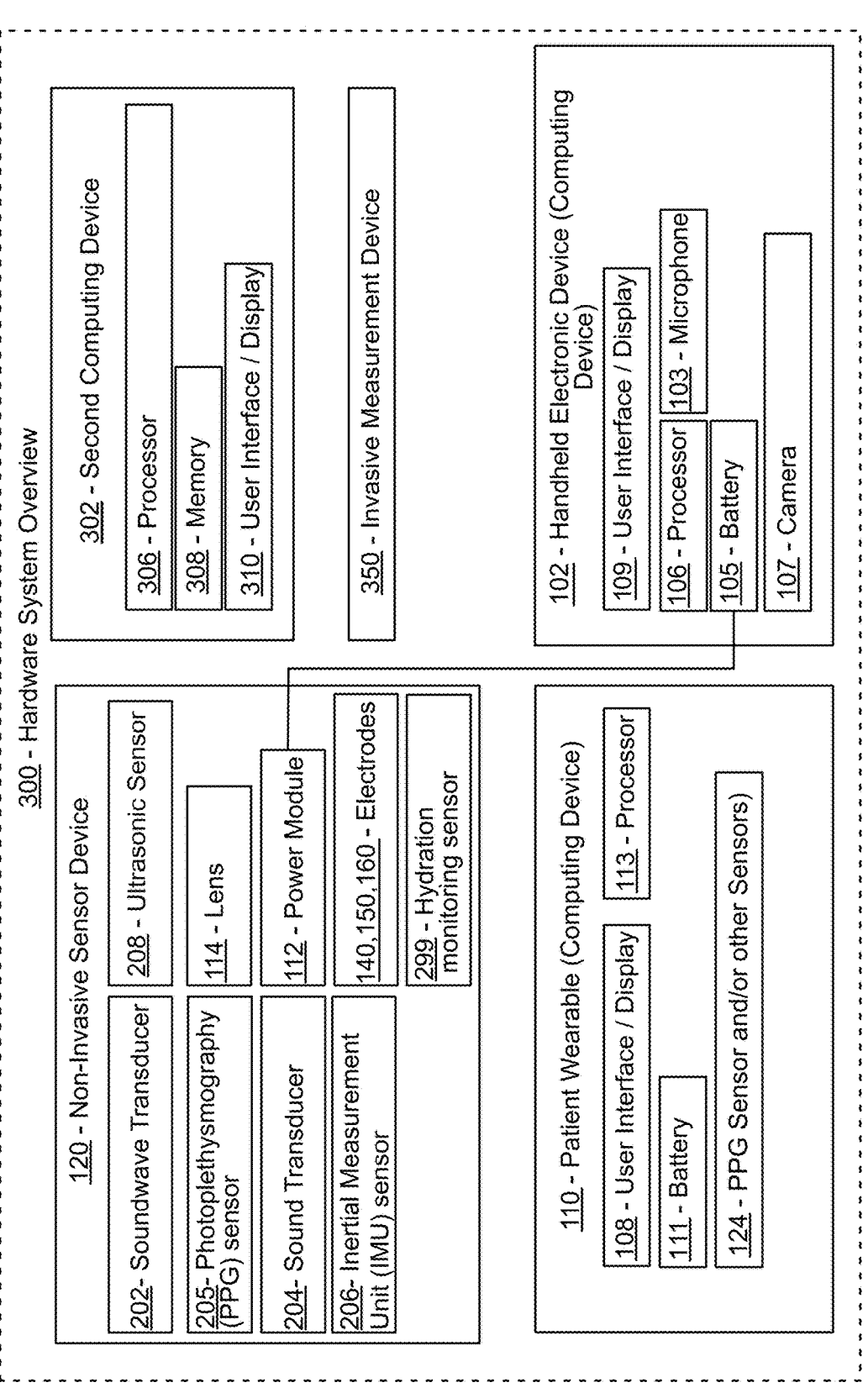
FIG. 3 illustrates a system-level view of an example hardware configuration of a cardiac health assessment system.

FIG. 3 illustrates a system level view of an example hardware configuration for the system. A person of skill in the art will realize that other configurations are possible to achieve goals similar to the example system. Here, non-invasive sensor device 120 includes a soundwave transducer 202, a Photoplethysmography (PPG) sensor 205, an ultrasonic sensor 208, lens 114, and an Inertial Measurement Unit (IMU) sensor 206. Non-invasive sensor device can include its own processor or microcontroller, or it can be entirely controlled by a computing device. Wearable device 110 can have one or more sensors. Here, wearable device 110 is in the form of a smartwatch and has a PPG sensor 124, a display 108, a processor 113, and a battery 111. Gold standard cardiac data is captured by invasive measurement device 350. Handheld electronic device 102 has its own microphone 103, a camera 107, a battery or other power source 105, a processor 106 and a display 108. A second computing device 302 has a processor 306, memory 308 and a display 310. In this example, this device is a remote device that receives the data from the invasive measurement device 350, non-invasive sensor device 120 and wearable device 110 and creates and trains the machine learning and classification models. The other devices are able to access the models, run the models remotely and/or download the models to run them locally. With enough computer power elsewhere in the system (e.g. in the cloud or on a smart phone 102) and adequate networking to enable data capture from the invasive measurement device 350, it is possible that second computing device is unnecessary. Invasive measurement device 302 can also have its own computing features such as a processor, memory and a display (not shown). Not shown is a system bus and/or network that enables communication on device and amongst the various devices of the system.

The patient-facing computing device 102 is directly or indirectly connected to the invasive measurement device 350 to obtain intracardiac pressure data of the users. In some embodiments, the measurement device 302 includes but is not limited to a catheter, an intra-aortic balloon catheter, a ventricular assist device, an implanted pressure sensor, and an implanted micro-computer. A person of skill in the art understands that many of these invasive measurement devices 350 are single use devices or reprocessed devices due to their contamination with bodily fluids or risk of damage in insertion, removal and life sustaining usage and that multiple invasive measurement devices 350 are used to get the intracardiac pressure data of the users. The invasive measurement device 350 may have its own processor, computer systems, memory, display and other electronics as shown in the patient monitor of FIG. 5. In some embodiments the invasive measurement device 350 can record data directly whereas in other embodiments its data is recorded on a computing device (102, 302, 110) or directly on the non-invasive sensor device 120. Invasive measurement device 350 can also be used for other invasive measurements including but not limited to imaging (e.g., x-ray, cat scan), blood pressure monitoring, heart rate variability, coronary angiography, intravascular ultrasound (IVUS), optical-coherence tomography (OCT), and intravascular MIll (IV-MRI) display plaques at a high spatial resolution. Near-infrared spectroscopy (NIRS) allows for the detection of chemical components of atherosclerotic plaques or electrocardiogram).

An example communication application housed on handheld electronic device 102 is configured to register the user over the communication application by receiving at least one credential from the user for providing access to the communication application. Examples of the credentials including but not limited to a username, password, age, gender, phone number, email address, location, etc. The communication application is further configured to receive demographic data pertaining to the user; receive cardiac health questionnaire data from the user; and transmit a final dataset by compiling the demographic data, and the cardiac health questionnaire data of the user. Demographic data may include birthplace, current location, gender, ethnicity, weight, and height. Cardiac health questionnaire may include questions pertaining to angina and may include measures of degree of chest pain or discomfort being characterised by one or more of the following: being limited to the sternum on any level and/or a left arm and/or left anterior chest (including but not limited to the anterior chest wall between the levels of clavicle and lower end of sternum), characterised by being provoked by either hurrying or walking uphill (including but not limited to by walking on the level, for those who never attempt more), characterised by when walking it must make the subject either stop or slacken pace, characterised by disappearing on a majority of occasions in 10 min or less from the time when the subject stands still. Cardiac health questionnaire may further be characterised by one or more attacks of severe pain across the front of the chest lasting for 30 min or longer. A cardiac health questionnaire may further consist of a shortness-of-breath scale, the Minnesota Living with Heart Failure Questionnaire and/or a Chronic Heart Failure Questionnaire. In some embodiments, the cardiac health questionnaire may consists of questions relating to one or more of chest pain, diabetes, hypertension, dyslipidemia, smoking history.

Demographic data and the cardiac health questionnaire data are important for managing the heart failure of the user. In some embodiments, the computing device 304, wearable device 110 or HED 102 present a questionnaire to the user where the user is prompted to answer questions about the user's cardiac health.

A user may include a patient, a patient using the communication application using the handheld electronic device 102 such as those included in this invention, or such a computing device itself. In some embodiments, the communication application 185 is executable on the handheld electronic device 102 of the user and implemented on one or more operating systems such as Android®, iOS®, Windows®, etc. In some embodiments, the communication application 185 is commercialized as a software application, or a mobile application, or a web application for capturing cardiovascular health data for managing heart failure.

The handheld electronic device 102 may further include a display 109 having a User Interface that may be used by the user or an administrator to initiate a request to view the cardiovascular health data and provide various inputs to the present system. In some embodiments, the User Interface (UI or GUI) is a convenient interface for accessing the information related to the cardiovascular health data, including the risk factors, and the cardiac health questionnaire data of the user. Display 109 may further be used to display cardiovascular health data to the users. The functionality of the system 100 may alternatively be configured within each of the plurality of computing devices 102.

The second computing device 302 optionally receives the intracardiac pressure data and non-invasive cardiac health data. The second computing device 302 includes a memory 308 to store a plurality of instructions and a processor 306 to execute the plurality of instructions. Memory 308 may be a non-volatile memory or a volatile memory. Examples of non-volatile memory may include, but are not limited to flash memory, a Read Only Memory (ROM), a Programmable ROM (PROM), Erasable PROM (EPROM), and Electrically EPROM (EEPROM) memory. Examples of volatile memory may include but are not limited to Dynamic Random-Access Memory (DRAM), and Static Random-Access memory (SRAM). The processor 306 may include at least one data processor for executing program components for executing user- or system-generated requests. Processor 306 may include specialized processing units such as integrated system (bus) controllers, memory management control units, floating point units, graphics processing units, digital signal processing units, etc. Non-limiting examples of processor 306 include a microprocessor, such as AMD® ATHLON® microprocessor, DURON® microprocessor OR OPTERON® microprocessor, ARM's application, embedded or secure processors, IBM® POWERPC®, INTEL'S CORE® processor, ITANIUM® processor, XEON® processor, CELERON® processor or other line of processors, etc. Processor 306 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

Processor 306 may be disposed of in communication with one or more input/output (I/O) devices via an I/O interface (not shown). I/O interface may employ communication protocols/methods such as, without limitation, audio, analog, digital, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

The processing and memory used in recording the data received from the non-invasive sensor devices 120, the invasive measurement devices 350, or training the machine learning and classification models can occur on processors in these devices individually (that is, they can be integral with the computing device that does the processing), if present, or distributed in processor cycles across these devices, distributed across processors that are remote in cloud-based servers, on-premise in medical centre servers, or elsewhere, or some combination of the above. Sometimes additional computing devices can be utilized for heavy computational needs, database and model repositories, as there can be a trade-off between portability and performance specifications in a handheld device. A person skilled in the art would appreciate that among the different possible configurations of processing and memory within the claimed inventions.

After discussing the hardware, it is time to discuss some of the machine learning model formation, training and application embodiments. FIG. 4 illustrates an example model and feature level view of some of the systems and methods herein. Non-invasive feature dataset 401 is combined with gold standard training data 450 to create machine learning program training 455. In some embodiments, the gold standard data may be dichotomized (e.g. into a 1 or 0 binarization based on category belonging) or further divided to give gold standard training data two or more classifications. The non-invasive feature dataset 401 are combined with this classified gold standard training data to create machine learning program training classification data. Such classifications can be divided into two or more numerical categories based upon, among other things, compliance with clinical standard of care, clinical definitions or clinical norms. At the non-invasive feature dataset level 401, which may include direct readings, generated features, the raw data may include, inter alia, soundwave readings 410, ultrasonic readings 405, PPG readings 415 and IMU readings 420. It may also include inputs from user questionnaires 430, past medical histories, demographic information 440 including but not limited to patient movement data (e.g., such as pedometer readings captured by the wearable device), pharmaceutical/diet adherence information 435 and external datasets 445. External datasets include, among other things, pre-existing information for different age groups that may be relevant to estimating intracardiac pressure. For example, if it were determined that patients within an age group of 55 to 65 may have an average intracardiac pressure of 20 mmHg in the broader population, such data may then be used to extrapolate an expected value of intracardiac pressure.

Machine learning program training 455 receives the non-invasive feature dataset 401, after optional data pre-processing. Data pre-processing (e.g., step 814 in FIG. 8) involves at least one of data cleaning, data integration, data reduction, and data transformation steps or other data manipulation techniques known in the art.

Data cleaning includes replacing missing values and removing noisy data (noise here being defined as a random variance in the measured variable). Data cleaning may be performed by removing the training example if the output label is missing, which may be due to an error during data entry such as a data transmission error, filling in missing value manually, using a standard value to replace the missing value, using central tendency (mean, median, mode) to replace the missing value, using central tendency (mean, median, mode) for attributes belonging to same class to replace the missing value, using the most probable value to fill in the missing value and/or using algorithms like regression and decision trees to impute the missing values.

A step of data reduction may be performed where a condensed representation of the dataset is sought, which is smaller in volume, while maintaining the integrity of original data. The purpose is to yield similar results more efficiently. Methods to reduce the volume of data that may be employed include limiting the data to certain ratios and/or filters. E.g. missing values ratios whereby attributes that have more missing values than a threshold are removed and/or low variance filters whereby normalized attributes with variance below a certain threshold may be removed. High correlation filters may further be used to reduce data whereby normalized attributes that have correlation coefficient higher than a threshold are removed, since similar trends means that there is limited novel information in subsequent variables. Principal component analysis (a statistical method which reduces the numbers of attributes by lumping highly correlated attributes together) may also be reduced to reduce data.

Data transformation includes transforming dataset into a form appropriate for data modelling including but not limited to smoothing, attribute/feature construction, summary and aggregation operations, normalization (the data in each attribute is scaled between a smaller range e.g. 0 to 1 or −1 to 1), discretization (raw values of the numeric attributes are replaced by discrete or conceptual intervals, which can in return be further organized into higher level intervals). and concept hierarchy generation for nominal data, whereby values for nominal data are generalized to higher order concepts.

The feature-level data is fed into the machine learning program training 455. (An equivalent training of the classification model 465 is not shown but may be present.) As a result, trained machine learning model 460 is able to provide insights into predictions and estimations of the gold standard data 470 and other things like recommendations 475. The model 460 can keep improving overtime with the addition of new data for training as well as ongoing usage of the non-invasive sensor device.

Figure 5A:
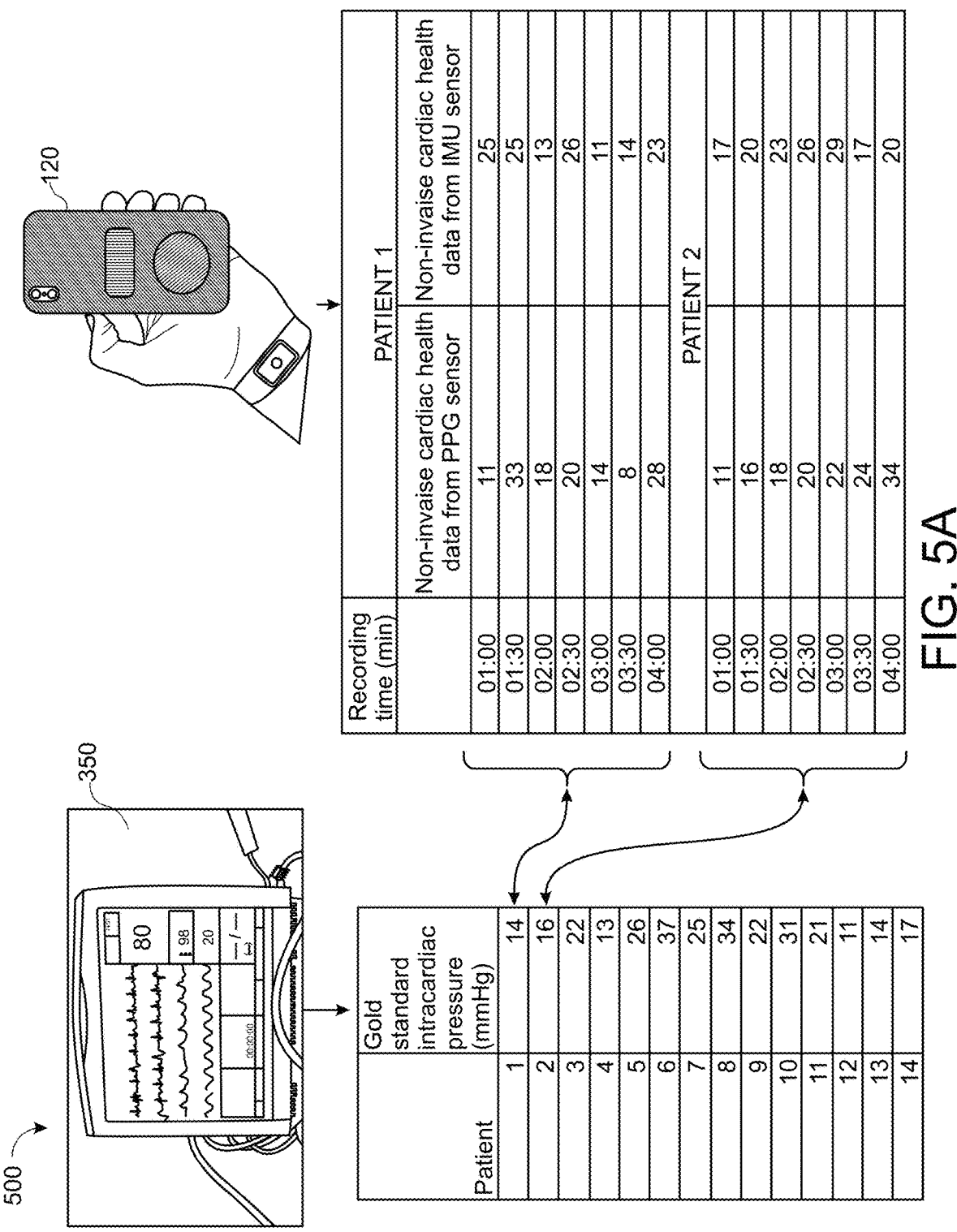
FIG. 5A illustrates an example process of recording raw data from example invasive or non-invasive sensors.

FIG. 5A illustrates an example of recording raw data from example invasive or non-invasive sensors. View 500 depicts a computing device receiving intracardiac pressure data from invasive measurement device 350 (shown as a patient monitor that is connected to one or more invasive sensors) and non-invasive data from the non-invasive sensor device 120 and wearable 110. Intracardiac pressure may comprise left ventricular pressure, left atrial pressure, pulmonary capillary wedge pressure, pulmonary artery pressure, right atrial pressure and/or right ventricular pressure. The data from the charts is for illustration purposes only. The processor of the computing device generates features from at least one or more portions of the non-invasive cardiac health data that fall within each of the one or more temporal windows. In this example, the measured invasive intracardiac pressure data is matched with the collected non-invasive data on a patient-by-patient basis. The matched data of each patient is aggregated into a final dataset for the machine learning analysis.

Temporal windows are used to look at the incoming data and define usable sections of the data for the diagnostics and machine learning and classification models. For the purposes of training, the data is collected from both the non-invasive data and the intracardiac pressure data from temporal windows at the same time. The same time refers to segments within the data that reasonably correspond to each other. While reasonably can mean simultaneously, it can also mean time periods close in time such that the data would still be expected to be accurate for those windows and neighbouring windows. Because of known intraday variations and cycles of the patient's intracardiac pressure, using data from windows too remote may lead to less accurate data. For example, the patients' 5:00 p.m. intracardiac pressure may be different from its 8:00 p.m. intracardiac pressure. However, data samples at 5:00 p.m. and 5:05 p.m. may reasonably correspond. If available, simultaneous or proximate-in-time data sampling will yield the most accurate training. In some embodiments, a temporal analysis of the user's data is performed. It is well-known that intracardiac pressure in a patient may vary within a day and across days. It may therefore be necessary to identify trends in data over several days and/or weeks to uncover meaningful clinical information and patterns. Such a temporal analysis may comprise comparing one or more sets of non-invasive cardiac data with one or more earlier sets of non-invasive data to uncover differences and/or patterns in the one or more sets of data. In such an embodiment, non-invasive data may include previous estimations of intracardiac pressure and/or cardiac health risk assessments.

The processor can determine the fit, e.g., best fit, of the temporal windows on the data to maximize the correlation. Best fit is only one possibility of curve fitting, and those skilled in the art will appreciate that other types of curve fitting can be used. Alternatively, a human can annotate or segment the data at defined points before the data is inputted into the machine learning model. For example, the temporal window might start at the beginning of the patient's PQRST wave or QRS wave and end of the end of these waves or after a certain number of periods of these waves.

Additionally, for each patient of the patient set used to train the models, invasive data and the non-invasive data are taken from the patient at the same time to correlate and calibrate the non-invasive data collected for each patient with the intracardiac pressure data of that patient. The patient holds, e.g., as shown in FIG. 1, the non-invasive sensor device to her body while the invasive measurement device captures invasive data of the patient such as intracardiac pressure data.

The processor is configured to train an example classification model and an example regression model based on, among other things, the processor-generated features by using the intracardiac pressure data as a gold standard. View 540 of FIG. 5B depicts an example of invasive data recorded as a dependent (y) variable (gold standard) and generated features of non-invasive sensor data recorded as an independent (x) variable to be used in training a machine learning regression model. Generated features may in some instances comprise time series data that has been transposed without removal and/or transformation of any raw data. This can lead to unbalanced datasets, where the X-variables outnumber the y-variables to such a degree that machine learning methods are unable to effectively identify patterns. It is therefore illustrative to generate features using a number of methods including but not limited to relating time series data columns to one another (e.g., soundwave transducer data divided by IMU sensor data), using summary statistics of each patient's sensor data (e.g. mean and/or median of soundwave transducer data), relating summary statistics to one another (e.g. mean of soundwave transducer data divided by the median of soundwave transducer data). The processor will continue in an iterative process until all meaningful relationships between the variables have been uncovered from feature generation and/or a certain amount of processing time has been reached.

FIG. 5C depicts the y-variable data of FIG. 5B altered based on an example rule classifying over and under a select amount of blood pressure for a classification model. The classification model shown in view 560 uses a conclusion about the data to classifies input data or output data into at least one class, which are then used to label the data or help the model classify an outcome of the machine learning model. For example, pulmonary hypertension is clinically defined as the mean pulmonary artery pressure of greater than or equal to 25 mmHg. A classification model can use this conclusion of how it is defined to create relationships based on the classification rather than the true value of a datapoint.

In this example, view 560 of the training classification model depicts where the gold standard data is binarized indicating whether over or equal to 25 mmHg). Here, a binary classification is shown to provide an outcome determination for optimization of the model. Even though a binary classification example is used, one of ordinary skill in the art would appreciate that other classification and types are within the scope of this application. As a further example, a presence of pulmonary arterial hypertension can be classified as mean pulmonary artery pressure of more than or equal to 25 mmHg and a pulmonary capillary wedge pressure of less than or equal to 15 mmHg. Pulmonary capillary wedge pressure gold standard data may be collected through a right heart catheterization and/or be approximated from direct left atrial pressure measurements using an invasive sensor. Pulmonary capillary wedge pressure may be measured by entering the catheter connected with a pressure transducer further than the pulmonary artery into the pulmonary capillary wedge to get the pressure in mmHg. The memory is configured to store the classification model and the regression model. In some embodiments, the classification model and the regression model are trained to estimate stroke volume measurements obtained from an echocardiogram gold standard.

Figure 6:
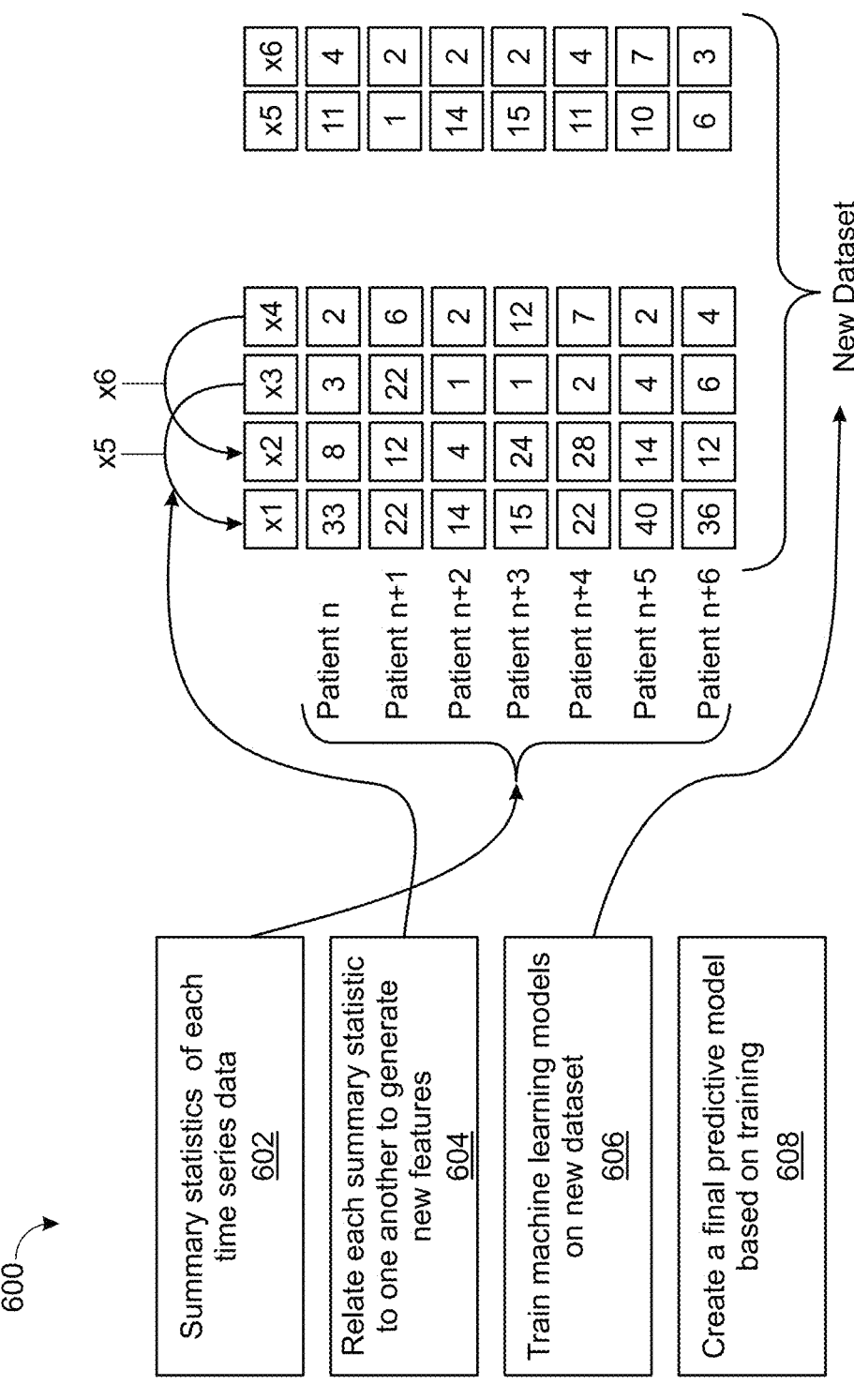
FIG. 6 illustrates a flow diagram of an example feature generation method.

FIG. 6 illustrates a flow diagram 600 of an example feature generation method showing a division of columns by one another. At step 602, the summary statistics of each time series data pertaining to a plurality of the patients are fed into the model. At step 604, the flow diagram relates each summary statistic to one another to generate new features. At step 606, machine learning models are trained on a new dataset. At step 608, a final predictive model is created based on the training of the machine learning models. Data without generated features can be used directly in the model, including both time series and non-time series data. This can be accomplished through applying different neural network models, including but not limited to convolutional neural networks (CNNs), where the data of each patient is individually fed into the machine learning model, without prior transposing to form one training dataset. This can be envisioned as an analysis similar to that of image-based machine learning using CNNs, whereby the patient's matrix of sensor data is analysed similarly to how one would analyse a matrix of pixels from an image. The user and/or physician have no input in the final dataset that is used to train the machine learning models.

For the purpose of this specification, "feature" refers to an input (e.g., x-variable in a regression model) of a model. Generated features as a whole can refer to the curated or manipulated sensor data or other patient data. And "gold standard" refers to using a specified diagnostic and/or measurement as one of the outputs (e.g., y-variable(s) of a regression model) of the model. Features can be automatically generated by a processor, can be inputted by humans, or can be directed using supervised machine learning concepts.

One of ordinary skill in the art would appreciate that other currently known and future machine learning methods can be interchanged with the models used herein including one or more of the following methods: decision tree-based machine learning methods, artificial neural networks, logistic regression, naive Bayes, nearest neighbour, support vector machines, boosted tree learning methods, and deep learning methods.

A neural network is like an artificial brain that can learn, recognize and process information. A neural network works by taking inputs (input units) arranged into a series of layers and translating them into outputs (output units) with hidden units in between. The connections between each unit are called weights. The higher the influence one unit has on another, the higher the weight (positive or negative).

Additionally, one of ordinary skill in the art would appreciate that currently known and future neural networks that can be used interchangeably with the neural networks described herein with minor adaptation include Perceptron Models, Convolutional Neural Networks, Recurrent Neural Networks, Long/Short Term Memory Networks, Gated Recurrent units, Hopfield Network Models, Boltzmann Machines, Deep Belief Networks, Autoencoders, Radial Basis Function Neural Networks, Modular Neural Networks, Sequence-To-Sequence Models and Generative Adversarial Networks. Throughout this specification, the use of the term "model" or "machine learning" or "machine learning model" or "neural network" can be generically applied to all of these models and network types.

The use of machine learning is able to sense, iterate and manipulate the data in a way beyond human capabilities. For example, the machine learning models may be able to detect and implement nonlinear relationships between the raw data collected from the patient's that to the human mind would be difficult to discern. For example, while a PPG sensor times series of a patient divided by a soundwave transducer times series may not imply much to the naked eye, a computer may then be able to discern valuable insights from such data. The example trained machine learning model is independent of the patients. That is, no calibration on an individual level is needed. The example trained model can adjust estimations based on distinct types of patients, etc., so that the model is generalizable.

A single sensor system requires many patients to achieve statistical significance. Using several sensors together in the non-invasive sensor device 120 has the benefit of drastically reduces this minimize size. Due to the presence of several non-invasive sensors, an example embodiment is trainable with a minimum of 715 patients to achieve statistical significance. This has a significant benefit.

In some embodiments, the processor is further configured to train a myocardial ischemia predictive model; a blood pressure estimation model; and a heart arrhythmia predictive model.

In some embodiments, the processor is further configured to train a patient medicine and diet adherence model. Failure to adhere to medicine and/or diet is a common precipitating risk factor of heart failure hospitalizations and is an important variable to track in order to be able to proactively prevent hospitalizations since these may precede rising intracardiac pressure and therefore be an early warning of impending heart failure. Specific physiological properties of a patient that may be detectable through non-invasive sensor data may deviate from expected values. These deviations may be distinct from general deteriorations in cardiac health arising from direct worsening of heart failure, e.g. the heart muscle weakening and/or becoming stiffer. A machine learning model may be trained to detect these deviations using gold standard data comprising the patient's self-reported medicine and/or diet adherence over a certain time-period, the patient's medicine and/or diet adherence as reported by someone else (e.g. a relative, clinician and/or system that can track the patient's medicinal and dietary habits). In some embodiments, medicine adherence may be tracked through one or more ingestible pills with data transmission capabilities. In such an embodiment, the pill would be able to transmit data to the EDC as it travels through the digestive system and thereby indicate that the medicine has been taken by the user. The pill could further send data pertaining to the digestive ability of the user with regard to the particular medicine that the user has taken.

In some embodiments, the EDC is equipped with a magnetometer which can detect abnormal traces of ferromagnetic levels in the blood of the patient/user. Detection of such abnormal traces may aid in determining whether the patient is adhering to their medication if there are ferromagnetic compounds present in the patient's medicine.

In some embodiments, a hospitalization risk machine learning model may be trained using non-invasive cardiac health data and patient outcome-based gold standard data. Said gold standard data may comprise hospitalizations, mortalities, morbidities and/or other health outcomes. Such a machine learning model can enable risk stratification of patients and may allow healthcare systems to focus resources more effectively on the most vulnerable patients. In a further embodiment, a machine learning model may be trained to identify which patients may benefit the most from increased care in order to optimize for a given target such as minimization of hospitalizations, minimization of mortality rates and/or improving self-reported health outcomes, etc.

In some embodiments, the users are segmented based on historical treatment data, wherein the users are a plurality of heart failure patients or heart disease patients. In another embodiment, the handheld electronic device 120 facilitates the users to feed demographic data and health questionnaire data of the users.

In some embodiments, the invasive intracardiac pressure measurement may be carried out manually by a clinician/cardiologist, e.g., through a right heart catheterization or an implanted sensor (e.g., a MEMS sensor in the left atrium or pulmonary arteries). The intracardiac pressure will then be recorded (e.g., by the clinician written down or entered into a database) or automatically transferred from the sensor to a computing device/database. In some embodiments, when a cardiologist measures the intracardiac pressure with a catheter and it will appear on the computing device 304 or cardiologist's screen. Then a nurse/cardiologist will enter the measurements into the database manually. When measurements are taken and entered manually into a computer, the temporal windows of non-invasive data optionally will be matched according to a unique patient identity corresponding to the date and approximate time that the intracardiac pressure and the non-invasive data was collected.

According to an example embodiment herein, the cardiac health assessment system is used for training a system using a non-invasive sensor device with a plurality of sensors to estimate intracardiac pressure data. The system includes a patient-facing computing device, a measurement device, and a second computing device. The patient-facing computing device is connected to the measurement device to obtain intracardiac pressure data of a plurality of users. The second computing device receives the intracardiac pressure data, myocardial ischemia gold standard diagnostic data, heart arrhythmia gold standard diagnostic data, and non-invasive cardiac health data. The second computing device includes a memory to store a plurality of instructions and a processor to execute the plurality of instructions. The processor is configured to separately match intracardiac pressure data, myocardial ischemia gold standard diagnostic data, and the heart arrhythmia gold standard diagnostic data with the non-invasive cardiac health data. The processor generates features from at least one or more portions of the non-invasive cardiac health data that fall within each of the one or more temporal windows for each gold standard data. The processor trains a classification model and a regression model based on the generated features by using the intracardiac pressure data as a gold standard for each gold standard data. The processor stores the classification model and the regression model for each gold standard data.

According to an example embodiment herein, the cardiac health assessment system is applicable for training a system using a non-invasive sensor device based on intracardiac pressure data. The system includes a patient-facing computing device, a measurement device, and a second computing device. The patient-facing computing device is connected to the measurement device to obtain intracardiac pressure data of a plurality of users. The second computing device receives the intracardiac pressure data and non-invasive cardiac health data. The second computing device includes a memory to store a plurality of instructions and a processor to execute the plurality of instructions. The processor is configured to match intracardiac pressure data with non-invasive cardiac health data; train a neural network model by using the intracardiac pressure data as a gold standard; and store the neural network model.

In some embodiments, the non-invasive sensor device includes but is not limited to a soundwave transducer, a Photoplethysmography (PPG) sensor, and an Inertial Measurement Unit (IMU) sensor.

This combination of sensor technologies and hardware architecture does not currently exist in any device other than those by the Applicant.

Furthermore, by leveraging a power source (e.g., a smartphone's battery), processor and operating system/display of another device, more types and more powerful sensors can be built into a device with a minimized size whilst retaining usability for the patient. Non-invasive data from multiple sensors of a similar sensor technology can more effectively cancel out environmental noise. One way this can be accomplished is through enabling data processing that can identify common noise artefacts that can be removed during a data analysis step. Another way noise can be minimized is through removing measurement errors by taking the difference between sensor data points assuming the measurement errors are similar in size. In cases where there are three or more sensors present, data triangulation may further be used identify a position of one or more sensors and normalize the data based on this position data. Another benefit of multiple sensors is that they add robustness across different recording environments and patient populations. Some sensors may work better in different populations. For example, optical sensors may be less accurate as skin tone gets darker. In another example, different sized hearts may reflect more seismic activity vs. acoustic activity.

FIG. 1A depicts an example user or patient 100 wears a wearable device 110 and holds a non-invasive sensor device 120 against her body. The wearable device 110 obtains physiological data of the user and transmits to a handheld electronic device (HED, 102) over a network. In some embodiments, the physiological data is obtained by the wearable device 110 during the collection of intracardiac pressure measurement data is included in the external data. In this example embodiment, non-invasive sensor device 120 is a phone case including sensors 130, 140 that obtain additional physiological data the user. (Additional detail of this case is discussed below in connection with FIG. 2. This non-invasive sensor device 120 can also transmit its data to the handheld electronic device 102 directly or over a network. FIG. 1B illustrates an example non-invasive sensor device 120, which takes the form of an electronic device case (EDC), and more specifically in this example, a smartphone case.

In some embodiments, the electronic device case (EDC) is adaptable to receive a handheld electronic device, wherein the HED 102 includes a display screen to display non-invasive cardiac health data derived from the data processed by the microcontroller.

In some embodiments, the EDC includes a disposable portion that is disposed after use. A disposable portion of the EDC may be desirable to meet hygienic standards, for example to avoid contamination if the same EDC were to be used on different patients. The disposable portion may consist of a simple adhesive sheet and/or a thin plastic film and/or a thin solid material that easily connects and disconnects to the EDC. The disposable portion may consist of a material that is environmentally friendly. In some embodiments, the disposable portion consists of a material that enhances contact with the patient's skin and/or is a see-through material. In some embodiments, the disposable portion may consist of a see-through material configured to enhance light from a photoplethysmography sensor so that skin penetrability is improved. In some embodiments, the disposable portion consists of one or more materials that enhance seismic and/or acoustic energy. In some embodiments, the disposable portion consists of one or more materials to enhance skin conductivity.

In some embodiments, the system includes a separate handheld electronic device (HED), wirelessly connected with the handheld electronic device and comprising a HED wireless transceiver configured to establish a communication with the computing device to transmit cardiac health data there-between. The computing device includes a processor configured to: detect, based on the classification model, an abnormal cardiac activity arising from a plurality of parameters that includes one or more of hypertension, myocardial ischemia, atrial fibrillation, aortic stenosis, aortic regurgitation, mitral stenosis, and/or mitral regurgitation; and estimate, based on the regression model, intracardiac pressure and/or left ventricular ejection fraction. It is well-known that cardiac regurgitation and/or cardiac stenosis can be identified using a number of non-invasive methods, such as ultrasound analysis and or analysis by electronic stethoscopes. Said non-invasive methods may be used as gold standard data when training a machine learning model to detect aortic stenosis and/or regurgitation as well as mitral stenosis and/or regurgitation. It is further well-known that elevated blood pressure (hypertension) can be detected using a number of non-invasive sensors, including but not limited to photoplethysmography (PPG). Left ventricular ejection fraction (LVEF) further positively correlates strongly with intracardiac pressure.

In some embodiments, the system includes a plurality of printed circuit boards (PCBs) to accommodate a plurality of sensors with a plurality of dimensions. A plurality of PCBs may be required in order to facilitate the placement of PCBs on different levels within the EDC. For example, it may be desirable for a PCB consisting of IMU and Photoplethysmography sensors to be placed close to the skin of a user to be closer to the seismic energy that is of interest and to facilitate light penetration respectively. In some embodiments, a PCB may have connectors protruding the backside to enable more robust hardware architecture by spreading hardware components that may cause electrical noise disturbances more evenly across the board. In such cases it may be necessary to facilitate an indentation to any casing that is intended to hold the PCB in place.

In some embodiments, the EDC includes a connector for transmitting data and power from the circuit board to the HED In some embodiments, the connector has the ability to move and adjust vertically and horizontally to enable different sized HEDs to be used with the EDC. In some embodiments, the EDC includes a rear magnetic material surface and/or other adhesive material to secure the handheld electronic device (HED) In other embodiments, the EDC has guide rails or is a close-fitting case that encloses the HED. In other embodiments, the EDC facilitates a strap to be attached to the EDC which can be pulled across and over the HED to help enclose the HED In other embodiments, the EDC includes hooks that are able to tightly grip the HED from the side and/or top of the EDC.

In some embodiments, the EDC may be connected to a computing device configured to control one or more implantable cardiac treatment devices. These implantable devices may include but are not limited to cardiac contractility modulation (CCM) devices, ventricular assist devices (VAD), pacemakers, etc. These implantable devices may be configured to be adaptive in their therapy based on information received from the EDC. For example, a left ventricular assist device may be configured to help the heart pump more when a high intracardiac pressure and/or other indication of a deterioration in the heart's pumping ability has been estimated through the EDC. Similarly, the LVAD may be configured to pump less once an indication of normalized intracardiac pressure has been indicated by the EDC. An adjustment in treatment from non-invasive intracardiac pressure monitoring from the EDC may furthermore lead an adjustable implantable occluder device, such as an atrial flow regulation (AFR) device to adapt. In such an embodiment, the diameter of an occluder device may be tightened to increase intracardiac pressure and loosened to decrease intracardiac pressure. In some embodiments, the EDC may receive data from a plurality of implantable devices.

In some embodiments, the sensors include a hydration monitoring sensor 299 configured to compute a hydration metric of a body tissue of the user. In some embodiments, the hydration monitoring sensor 299 may comprise a bioimpedance measurement sensor, a sensor configured to gather galvanic skin response data through electrodermal activity (EDA), microfluidic sweat sampling sensor configured to identify sweat electrolyte ion concentrations, electrodes made of an elastic polymer composite that includes conductive silver nanowires, one or more soundwave transducers configured to determine an ultrasound velocity in a muscle and/or other sensors able to collect skin conductance data. In some embodiments, the hydration metric is a relative hydration metric based on the user's historic hydration sensor measurements. In such a case the absolute hydration metric number may not be informative in itself but deviations from a baseline may be informative of changes in hydration resulting from a deterioration in cardiac health.

In some embodiments, a soundwave transducer may be configured to determine an ultrasound velocity in a muscle and infer the hydration status of a body. A deviation in ultrasound velocity, e.g. a speed of less than 1540 m/sec, may be indicative of an increased resistance from increased hydration.

In some embodiments, a photoplethysmography (PPG) sensor generates PPG waveforms, wherein the processor is configured to determine changes in tissue volume and changes in vascular volume in the user based on the PPG waveforms generated by the PPG sensor. A level of PPG light penetration lower than what can be expected from normal human tissue may indicate an elevated hydration level. In some embodiments, the EDC is configured to facilitate long-term wear on the patient by connecting to a wearable structure. The wearable structures may include but is not limited to a vest, a garment, a strap and/or a necklace. Further, the wearable structures are adjustable in size to fit any size of electronic devices. For example, a small pocket and/or gap in a vest may be adjustable in terms of dimensions to fit any smartphone.

In some embodiments, the wearable structures may comprise a battery to enable long-term monitoring. In some embodiments, the EDC is configured to be used as a Holter monitor by analysing the presence of heart arrhythmias over an extended period of time. In some embodiments, the non-invasive sensor device may be connected to a step-counter to assess a user's physical activity. The physical activity assessment may be used to estimate the user's cardiac health, including but not limited to intracardiac pressure and/or risk of hospitalization. In some embodiments, the step-counter includes a handheld electronic device, wearable, electronic device with equipped with an inertial measurement unit and/or a manual step-counter configuration.

In some embodiments, a temporal analysis of the user's data is performed. Such a temporal analysis may comprise comparing one or more sets of non-invasive cardiac data with one or more earlier sets of non-invasive data to uncover differences and/or patterns in the one or more sets of data. In such an embodiment, an earlier non-invasive set of data may include intracardiac pressure estimations stored in a memory of a computing device, an electronic device case and/or on a server to facilitate easy access.

In some embodiments, a hospitalization risk machine learning model may be trained using non-invasive cardiac health data and patient outcome-based gold standard data. Said gold standard data may comprise hospitalizations, mortalities and/or other health outcomes. Such a model can enable risk stratification of patients and allow healthcare systems to focus resources on the most vulnerable patients. In an embodiment, the cardiac health assessment system includes a patient risk stratification model to estimate future adverse patient health event risks. Such a model may include the patient's data collected through the EDC and may be trained on ex-post patient outcomes. Such outcomes may include but are not limited to hospitalizations, mortality rates, morbidity rates and/or general patient health assessments. In a further embodiment, a machine learning model may be trained to identify which patients may benefit the most from increased care in order to optimize a given target such as hospitalizations, mortality rates and/or self-reported health outcomes, etc. In some embodiments, a patient's medicine dosage may be delivered through an automated dispensing device which automatically adjusts the required dosage.

FIG. 2 illustrates a perspective view of an embodiment which includes various components of the non-invasive sensor device 120 in the form of electronic device casing for use with a handheld electronic device (HED) 102, in accordance with at least one embodiment. The non-invasive sensor device 120 having a shape adapted to secure a plurality of components within the non-invasive sensor device 120. In some embodiments, the HED includes a soundwave transmitter to broadcast a plurality of audio instructions to place the handheld electronic device (HED) on the user's body to capture intracardiac pressure data. Examples of the HED include but are not limited to a smartphone, a mobile, or a tablet. The components include a soundwave transducer 202, an Inertial Measurement Unit (IMU) sensor 206, and a microcontroller (not shown). The IMU sensor 206 captures seismic and auscultation signals indicative of the venous thromboembolism (VTE) risk of the user. The non-invasive sensor device 120 comprises sensor signal-enhancing material 130 to amplify seismic and acoustic auscultation signals. Examples of the sensor signal-enhancing material may include but is not limited to sound absorbers made from porous materials, micro-perforated plates, micro-perforated panel absorbers backed with mechanical impedance plates where the backed cavity is limited, and/or piezoelectric material The soundwave transducer 202 captures auscultation signals indicative of the cardiac health of the user. The IMU sensor 206 captures seismic auscultation signals indicative of the cardiac health of the user. The microcontroller processes data received from the PPG sensor, the soundwave transducer, and the IMU sensor to obtain non-invasive sensor data. The communication application is executed by the handheld electronic device (HED) In some embodiments, the non-invasive sensor device 120 includes a soundwave transceiver, a PPG sensor 205, and a soundwave transmitter. The PPG sensor 205 measures blood volume changes in a skin area in response to venous hemodynamic changes. In some embodiments, the PPG sensor 205 generates infrared (IR) light to measure the blood volume. In some embodiments, the PPG sensor 205 is a non-invasive, inexpensive, and convenient diagnostic tool to measure oxygen saturation, blood pressure, and cardiac output. In some embodiments, the PPG sensor 205 is placed at the top right of the non-invasive sensor device 120 and may be connected to a second microcontroller. In some embodiments, the wearable device 118 and non-invasive sensor device 120 include electrodes 140, 150, and 160 for performing electrocardiography.

In another example embodiment, the stored classification model and the regression model are transferred to the non-invasive sensor device 120, wearable device 110, or a patient-facing handheld electronic computing device 102. The handheld electronic device 102, the wearable device 110, the second computing device 302, and the invasive measurement device 350 are communicatively coupled over the network. Network may be a wired or a wireless network, and the examples may include but are not limited to the Internet, Wireless Local Area Network (WLAN), Wi-Fi, Long Term Evolution (LTE), Worldwide Interoperability for Microwave Access (WiMAX), and General Packet Radio Service (GPRS).

Figure 8:
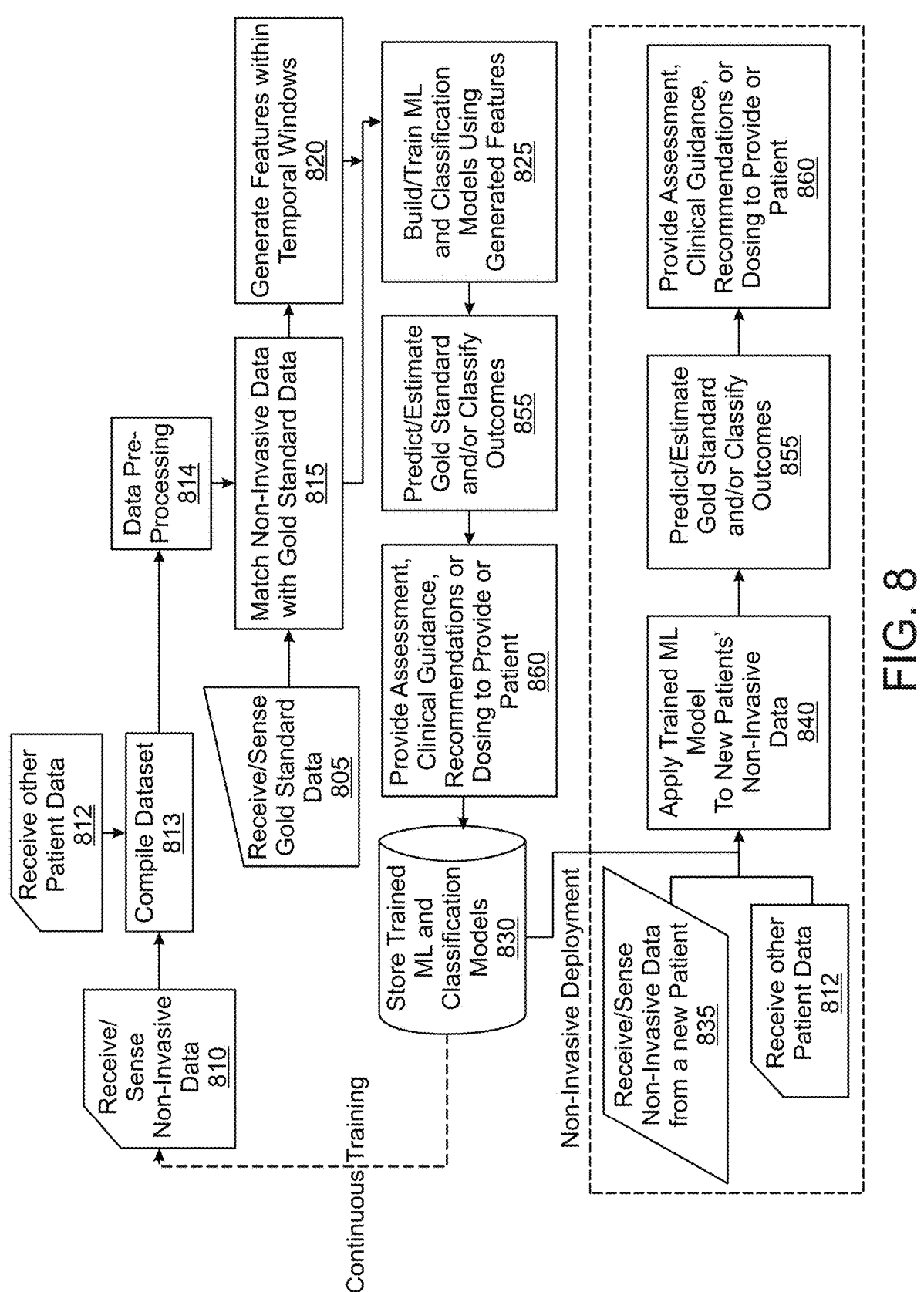
FIG. 8 is a flowchart of an example method of training and applying a machine learning model and a classification model.

FIG. 8 illustrates an example flow chart of a non-invasive cardiac health assessment method for training and applying a model using a non-invasive sensor device to estimate intracardiac pressure data of a user. The following steps are performed by one or more processors. In step 805, gold standard data from an invasive measurement device is received or captured for each of a plurality of patients. As discussed elsewhere, this could be intracardiac pressure data sensed from an example balloon catheter. In step 810, non-invasive cardiac health data is received or captured using non-invasive sensor device for each patient. Optionally, in step 812, other patient data may be received such as user questionnaires, user demographic data, and other data mentioned in this specification. This information can be fed in through any of the computing devices with a user interface. In step 815, the non-invasive data and the gold standard data is matched through a unique patient ID. In step 820, the processor generates features from at least one or more portions of the non-invasive cardiac health data that fall within each of one or more temporal windows. Feature generation may be done as described in FIG. 5B and FIG. 6. In step 825, the generated features are inputted into machine learning and classification models to build and train these models. In step 830, these trained models are stored. The storage can be in a number of places so that the models can be accessed or used from different devices. In step 835, non-invasive readings are received from a new patient. In step 840, these models can be applied to the non-invasive readings from the new patient. In step 845, this new data and related analysis can be used to improve the models. In step 855, these models can predict or estimate the gold standard data or classify outcomes from the non-invasive data. In optional step 860. the models can provide assessment, clinical guidance, recommendations, or dosing to the patient, provider or caregiver. It will be appreciated by those skilled in the art that subprocesses (e.g., training or deploying) of this method can be iterated independently here without processing the entire method and that certain steps may be optional, non-essential or reconfigurable. It will also be appreciated that more than one model, only one model or different models from those shown can be used under this model.

FIG. 10 illustrates a second flow diagram 1000 of a method for training a non-invasive sensor device based on intracardiac pressure data. The method includes step 1002 of obtaining, by a first computing device connected to a measurement device, intracardiac pressure data of a plurality of users. The method includes step 1004 of receiving, by a second computing device, the intracardiac pressure data, myocardial ischemia gold standard diagnostic data, heart arrhythmia gold standard diagnostic data, and non-invasive cardiac health data. The patient-facing computing device includes a memory to store a plurality of instructions and a processor to execute the plurality of instructions. At step 1006, the processor is configured to separately match intracardiac pressure data, myocardial ischemia gold standard diagnostic data, and the heart arrhythmia gold standard diagnostic data with the non-invasive cardiac health data. At step 1008, the processor is configured to generate features from at least one or more portions of the non-invasive cardiac health data that fall within each of the one or more temporal windows for each gold standard data. At step 1010, the processor is configured to train a classification model and a regression model based on the generated features by using the intracardiac pressure data as a gold standard for each gold standard data. At step 1012, the processor is configured to store the classification model and the regression model for each gold standard data.

Using the Models

Once the models are trained, they are usable to estimate invasive measurements, suggest health conditions, or suggest treatments without the need of the invasive measurements themselves. In some embodiments of this application, the models are used to estimate intracardiac pressure. The use of the non-invasive data of a new patient with a machine learning model which has been trained to estimate intracardiac pressure and a plurality of cardiac health conditions will reveal better information about the patient's health condition than only non-invasive data itself can reveal.

Capturing Cardiovascular Health Data for Managing Heart Failure Example

Figure 9:
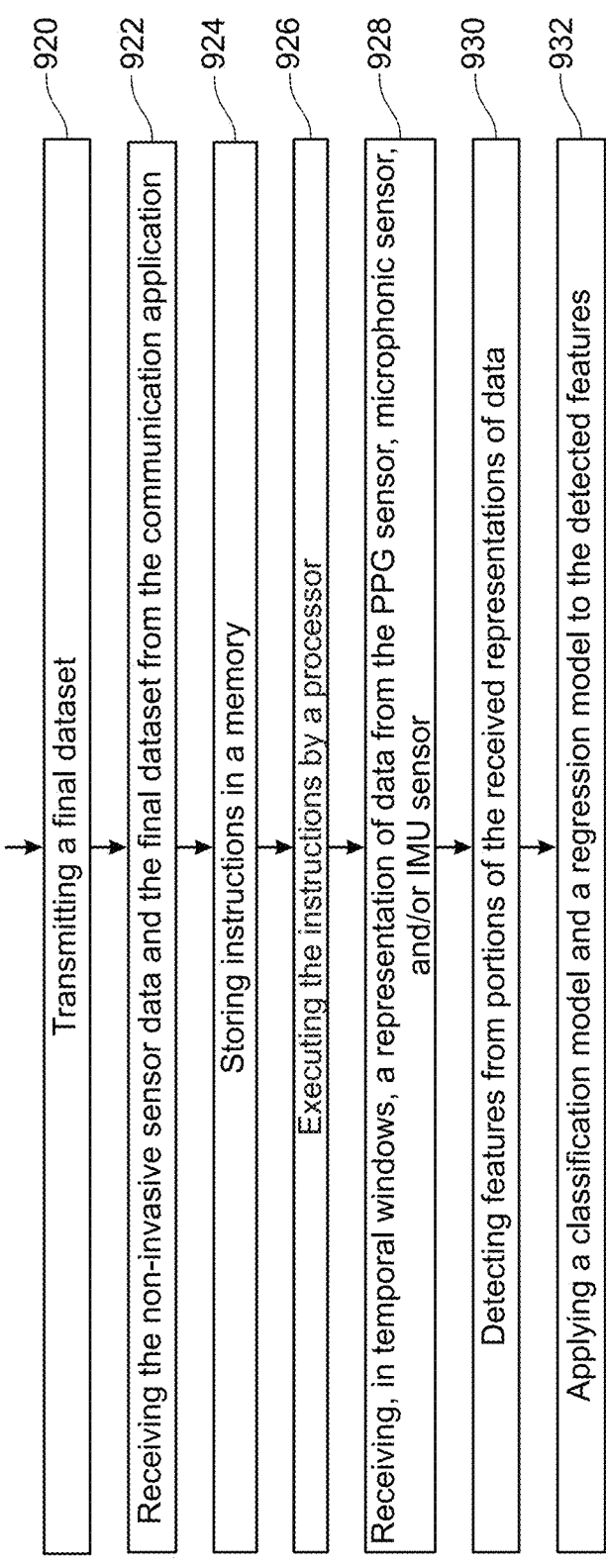
FIG. 9 illustrates a flowchart of an example method for capturing cardiovascular health data for managing heart failure.

FIG. 9 illustrates a flowchart 900 of a method for capturing cardiovascular health data for managing heart failure, in accordance with an alternative embodiment of the present invention. The method includes a step 902 of measuring, by a Photoplethysmography (PPG) sensor, volumetric variations of blood circulation and heart arrhythmias. The method includes a step 904 of securing a plurality of components within a non-invasive sensor device. The method includes a step 906 of capturing, by a soundwave transducer, auscultation signals indicative of the cardiac health of the user. The method includes a step 908 of capturing, by an Inertial Measurement Unit (IMU) sensor, seismic auscultation signals indicative of the cardiac health of the user. The method includes a step 910 of processing, by a microcontroller or processor, data received from the PPG sensor, the soundwave transducer, and the IMU sensor to obtain non-invasive sensor data. The method includes a step 912 of executing a communication application executed by a processing unit of the handheld electronic device (HED) In some embodiments, the HED includes a soundwave transmitter to broadcast a plurality of audio instructions to place the handheld electronic device (HED) on the user's body to capture intracardiac pressure data. The method includes a step 914 of registering the user over the communication application by receiving at least one credential from the user for providing access to the communication application. In some embodiments, the communication application alerts the user to perform an exercise, and to reduce one or more heart failure risk factors. The method includes a step 916 of receiving demographic data pertaining to the user. The method includes a step 918 of receiving cardiac health questionnaire data from the user. The method includes a step 920 of transmitting a final dataset by compiling the demographic data and the cardiac health questionnaire data of the user. In some embodiments, the computing device facilitates the user to respond to a questionnaire about the user's cardiac health. In some embodiments, the communication application facilitates the user to initiate a telehealth session with a heart failure management professional through the user's handheld electronic device 102 or wearable device 110. The professional can get live readings from the user's non-invasive sensor device 120 or wearable device 110, as well as diagnostics and recommendations through the machine learning model.

In some embodiments, the wearable device includes electrodes that enable electrocardiography. The method includes a step 922 of receiving the non-invasive sensor data and the final dataset from the communication application. The method includes a step 924 of storing a plurality of instructions pertaining to the management of heart failure, classification models, and regression models to estimate cardiac health in a memory. The method includes a step 926 of executing the instructions by a processor coupled with the memory. The method includes a step 928 of receiving, in one or more temporal windows, a representation of data from one or more of the following: the PPG sensor, the soundwave transducer, and the IMU sensor. The method includes a step 930 of detecting features from at least one or more portions of the received representations of data that fall within each of the one or more temporal windows. The method includes a step 932 of applying a classification model and a regression model to the detected features. The trained classification model and the regression model are configured for: estimating intracardiac pressure of the user; estimating coronary artery disease risk of the user; estimating arrhythmia risk of the user; and adjusting one or more medications of the patient based on the estimations of the intracardiac pressure, coronary artery disease risk, and heart arrhythmia risk of the user.

Figure 12A:
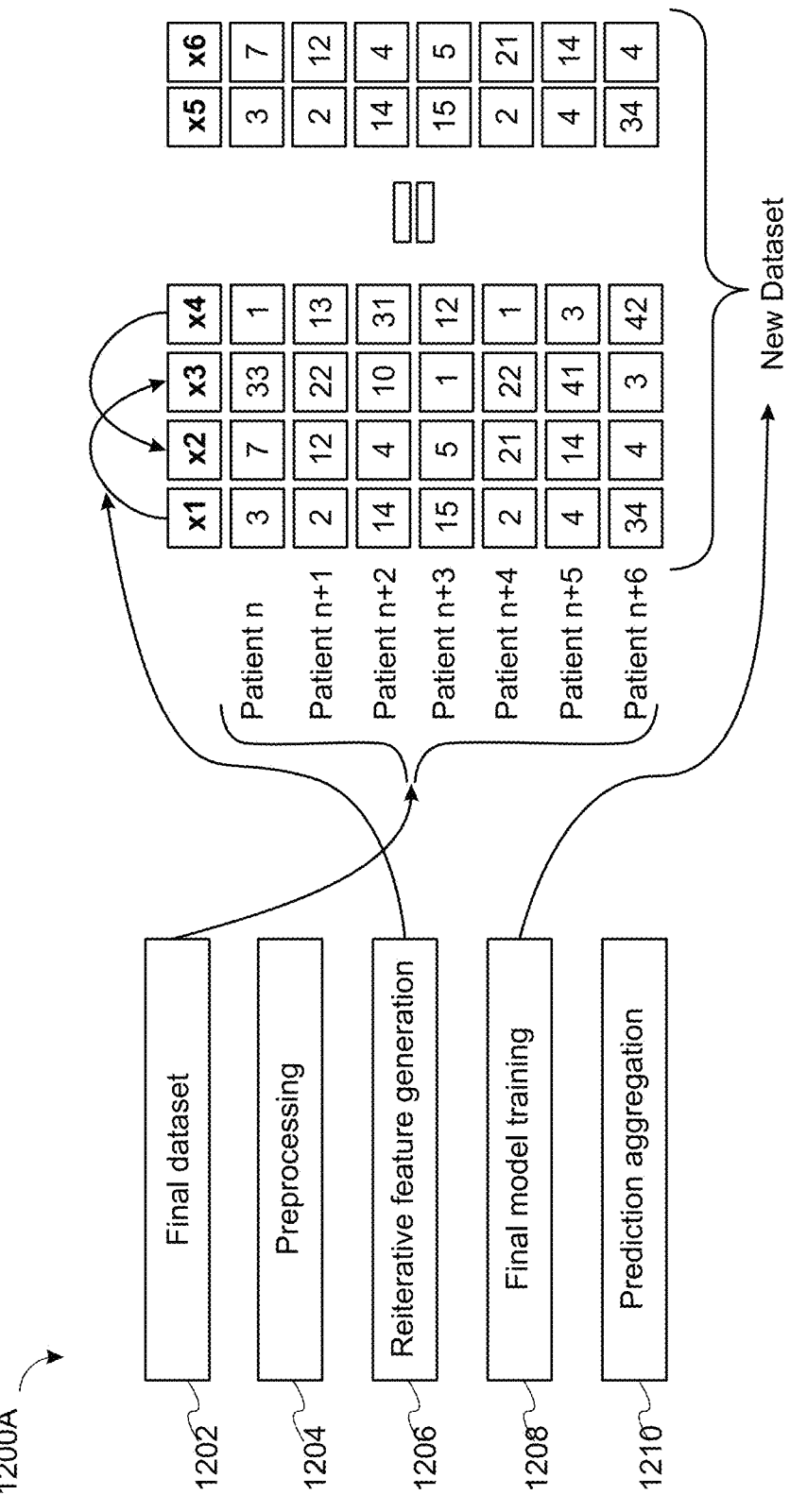
FIG. 12A is a flowchart of an example method of training and applying a machine learning model to the cardiac health assessment system.

FIG. 12A is a flowchart 1200A of an example method of training and applying a machine learning model to the cardiac health assessment system. At step 1202, a final dataset is captured from various sensors. At step 1204, the final dataset is pre-processed by performing data cleaning, data integration, data reduction, and data transformation steps. At step 1206, the pre-processed final dataset undergoes reiterative feature generation. Reiterative feature generation allows for the detection of relationships between variables and can help uncover important patterns. Reiterative feature generation has the benefit of being traceable and interpretable throughout the machine learning process. This means that each interaction and each variable that was related to each other can be tracked and analysed retrospectively. Then at step 1208, a machine learning model is trained based on the features generated at step 1206. A plurality of machine learnings models may be trained at step 1208. The plurality of machine learning models may be combined to create an ensemble of machine learning models and/or be stacked, to generate a machine learning system that is more robust in predicting and/or estimating an outcome. Machine learning models based on different underlying distribution assumptions and/or different machine learning methodologies may be used at this point to ensure robustness across different datasets. E.g., a Random Forest Regressor which is an example of a tree-based machine learning method, may be combined with a logistic regression-based model which is an example of a machine learning method based on a logistic distribution assumption. As a result, at step 1210, the machine learning model is trained can provide insights into predictions and estimations of the cardiac health data.

FIG. 12B is a flowchart 1200B of a method of performing a reiterative process by the machine learning model. At step 1212, the original dataset is received from the sensors and patients. Then at step 1214, the original dataset is used to generate the feature. At step 1216, the variables are selected that explain x % of the results. X may be chosen as a function of availability of computing power where a higher number of x may yield a higher number of generated variables and therefore a higher number of datapoints to be analysed, which will result in a higher computing power needed and/or longer computing times. At step 1218, the method determines whether the accuracy of the cross-validation is improved. If the accuracy of the cross-validation is improved, the process again starts from step 1214. If the cross-validation is not improved it can be concluded that there are no further important relationships and/or patterns to be identified in the dataset and that the machine learning models have been trained to the best of their abilities. In such a case, the process performs step 1220 of selecting variables that explain n % of results. Then at step 1222, the one or more final machine learning model is trained.

FIG. 13 illustrates a flowchart 1300 of a method for assessing the cardiac health of a user. The method includes a step 1302 of securing, by an electronic device case (EDC), a handheld electronic device (HED). The EDC having a shape adapted to secure the HED. The method includes a step 1304 of amplifying, by a sensor signal-enhancing material, seismic and auscultation signals. The method includes a step 1306 of capturing, by a soundwave trans- ducer, cardiac audio signals indicative of the cardiac health of the user. The method includes a step 1208 of capturing, by a photoplethysmography (PPG) sensor, visual data per- taining to tissue colour and/or blood flow. The method includes a step 1310 of capturing, by an Inertial Measure- ment Unit (IMU) sensor, seismic and auscultation signals indicative of the cardiac health of the user. The method includes a step 1312 of transmitting, by a microcontroller and/or a micro controlling unit and/or a microprocessor unit connected to a circuit board, cardiac health data received from a plurality of sensors to a computing device over a network. The circuit board may be optimized and manufac- tured in accordance with standards that enables it to be fit for specific medical applications, including but not limited to be more robust to electrical signal noise, reducing impact of electrical magnetic interference, improving physical sturdi- ness and/or ensuring heightened defensibility in terms of cybersecurity. The circuit board (PCB) may be fabricated with material fr4 or equivalent, in accordance with ipc-6012, class 2; ipc-6011, with a board warp or twist level limit of 1% 5. 1.0 oz. The computing device includes a processor configured to receive, in one or more temporal windows, a representation of one or more of the IMU sensor, the PPG sensor, and the soundwave transducer signal recorded by the EDC. The processor is configured to detect features of the IMU sensor, the PPG sensor, and the soundwave transducer from at least one or more portions of the received represen- tations falling within each of the one or more temporal windows. The processor is configured to identify patterns of the features of respective sensors from within the one or more portions based on at least a classification model or a regression model. The processor is configured to estimate, based on the regression model, intracardiac pressure and/or left ventricular ejection fraction.

In some embodiments, the handheld electronic device is secured within the EDC includes a display screen to display cardiac information derived from the cardiac health data received from the microcontroller. In some embodiments, the EDC is configured to capture cardiac health data of the user when positioned against the chest of the user.

In some embodiments, the circuit board includes a pro- cessing unit to execute the instructions pertaining to a cardiac monitoring application. In some embodiments, the cardiac monitoring application is based on one or more operating systems comprising one or more of the following: Amazon Fire®, One UI®, Librem®, EMUI®, Android®, and iOS®. The processing unit is configured to display one or more commands to position the EDC against the chest of the user. In some embodiments, the EDC includes a dispos- able portion that is disposed after use.

Figure 14:
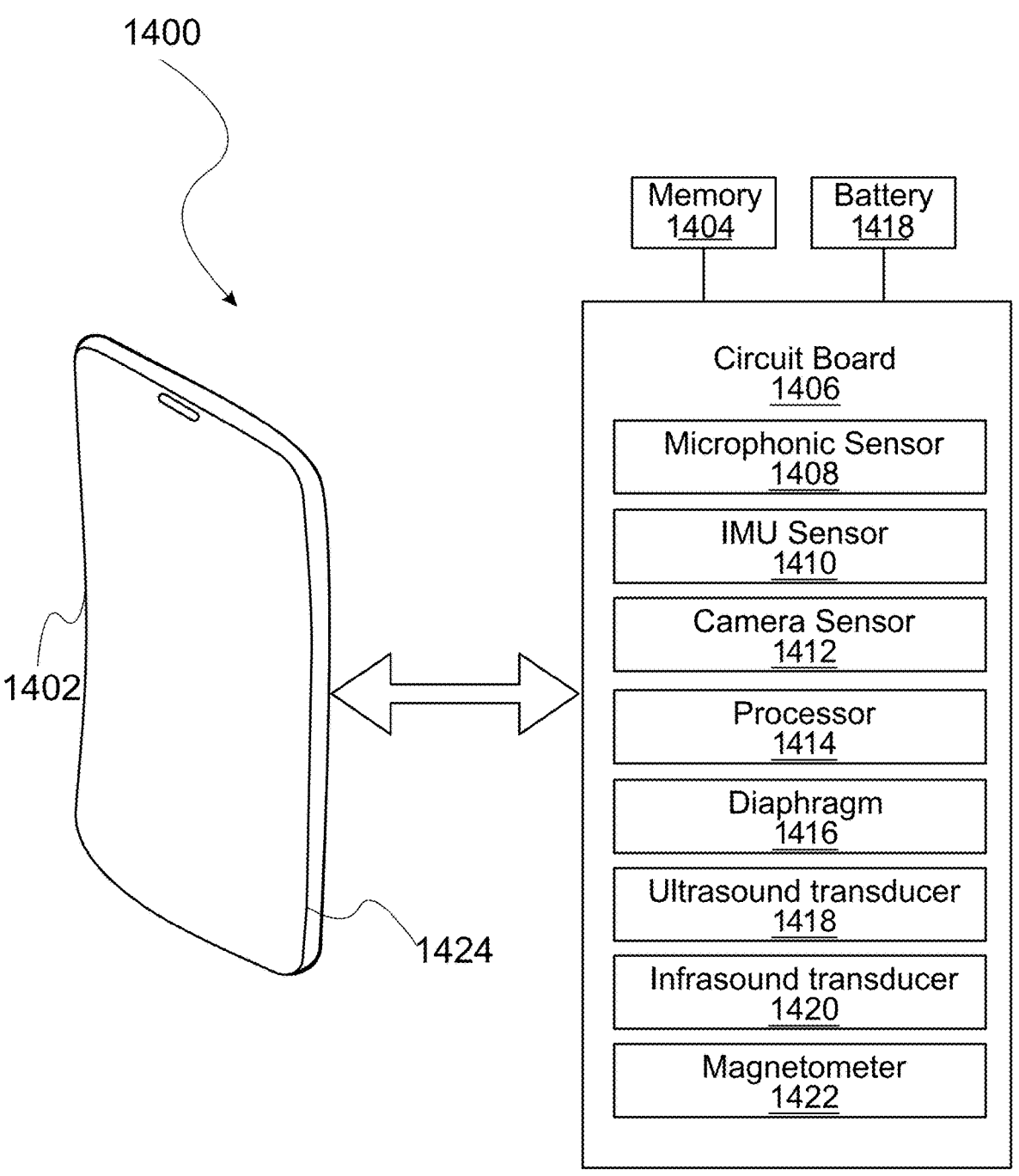
FIG. 14 illustrates a block diagram of the cardiac health assessment system, in accordance with embodiments of the claimed subject matter.

FIG. 14 illustrates a block diagram of the cardiac health assessment system 1400, in accordance with at least one embodiment. The cardiac health assessment system 1400 includes a memory 1404, a circuit board 1406, and a touchscreen controller 1424 that are integrated into a HED 1402. In an embodiment, the HED 1402 has a shape adapted to fit firmly on the user's chest. The shape of the HED 1402 may also be any suitable shape or it may be constructed so that the shape can be adjustable including being adjusted by the user to a user's shape. In some embodiments, the shape of the HED 1402 is bent or curved so that it can fit optimally on the patient's chest. The HED 1402 may be similar in shape and function to a smartphone, a mobile device, a phablet, a tablet, and the like. The memory 1404 stores a classification model, a regression model, and a plurality of instructions pertaining to a cardiac monitoring application.

In an embodiment, the plurality of instructions pertaining to a cardiac monitoring application may comprise but are not limited to information regarding how and when to execute the classification and regression models, what questions and how the user should be prompted with these questions, information regarding the detection of whether or not the HED has been correctly placed by the user, the prompts given to the user so that the user can log in with their credentials, information regarding ensuring that there are no cyber security risks present, and information regarding enabling data transmission and enabling connectivity with the wearable device coupled to the system. These instruc- tions may take several forms, they may be simple decision rules and/or they may be adaptive to the use patterns of the user to ensure robustness across different users with different interpretations of the information that may be presented in the cardiac monitoring application.

In an embodiment, the cardiac monitoring application is based on one or more operating systems, for example operating systems such as Amazon Fire®, One UI®, Librem®, EMUI®, Android®, and iOS®. The cardiac health assessment system 1400 allows the user to register with the cardiac monitoring application configured to oper- ate within the HED 1402. In an embodiment, the user may be required to answer a short questionnaire about their health. In some embodiments requested, information may be requested but not required from the user. A user may include a patient, a patient using the cardiac monitoring application using the HED 1402 with their own body, and/or any other person such as a healthcare professional using the HED, for example using the HED to execute the functions of the embodiments with a patient.

The memory 1404 may be a non-volatile memory or a volatile memory or any combination of these types of memory. Examples of non-volatile memory may include, but are not limited to flash memory, a Read Only Memory (ROM), a Programmable ROM (PROM), Erasable PROM (EPROM), and Electrically EPROM (EEPROM) memory. Examples of volatile memory may include but are not limited to Dynamic Random-Access Memory (DRAM), and Static Random-Access memory (SRAM).

The circuit board 1406 includes a microphonic sensor 1408, an Inertial Measurement Unit (IMU) sensor 1410, a camera sensor 1412, and a processor 1414. In an embodi- ment, the circuit board 1406 is referred to as a printed wiring board, printed wiring card, or a printed circuit board (PCB) that mechanically supports and electrically connects electri- cal or electronic components of the embodiments using conductive tracks, pads, and other features etched from one or more sheet layers of copper laminated onto and/or between sheet layers of a non-conductive substrate. The microphonic sensor 1408 captures cardiac sound wave sig- nals indicative of the cardiac health of a user and/or a patient. The IMU sensor 1410 captures seismic signals indicative of the cardiac health of the user. The camera sensor 1412 enables visual data collection of tissue and photoplethysmography. In an embodiment, the camera sensor 1412 is a phone camera image sensor such as a CMOS image sensor.

The processor 1414 is configured to: execute the plurality of instructions about the cardiac monitoring application; display one or more commands so that the HED 1402 can be positioned against the chest of the user; detect an abnormal cardiac activity arising from a plurality of parameters by deploying the classification model; and estimate intracardiac pressure by deploying the regression model. In an embodiment, ejection fraction, cardiac output and blood pressure may be estimated by deploying the regression model. In an embodiment, the classification model, and the regression model are trained by using intracardiac pressure data measured from a catheter and/or an invasive pressure sensor which are considered the gold standard in the industry for measuring such types of data. According to several embodiments, gold standard ejection fraction data may comprise data obtained from an ultrasound analysis and/or cardiovascular magnetic resonance (CMR) that is used to train the classification model and regression model. According to many embodiments, gold standard cardiac output data may comprise data obtained from a Pulmonary Artery catheter-based thermodilution. According to many embodiments, gold standard blood pressure data may comprise data obtained from a sphygmomanometer and/or an arterial line.

Memory 1404 is configured to register the user over the cardiac monitoring application by receiving one or more credentials from the user for providing access to the cardiac monitoring application. Examples of the credentials include but are not limited to, a username, password, age, gender, phone number, email address, location, as well as any other suitable information. In several embodiments, the cardiac monitoring application is commercialized as a software application or a mobile application, a web application for cardiac health assessment or any combination of these.

The processor 1414 may include at least one data processor for executing program components for executing user- or system-generated requests. Processor 1414 may include specialized processing units such as integrated system (bus) controllers, memory management control units, floating point units, graphics processing units, digital signal processing units, etc. Processor 1414 may include a microprocessor, such as AMD® ATHLON® microprocessor, DURON® microprocessor OR OPTERON® microprocessor, ARM's application, embedded or secure processors, IBM® POWERPC®, INTEL'S CORE® processor, ITANIUM® processor, XEON® processor, CELERON® processor or other line of processors, etc. Processor 1414 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), and the like.

Processor 1414 may be disposed of in communication with one or more input/output (I/O) devices via an I/O interface. I/O interface may employ communication protocols/methods such as, without limitation, audio, analog, digital, RCA, stereo, IEEE1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), and the like.

In an embodiment, the processor 1414 triggers a message transmission to a computing device, for instance a computing device used by a healthcare professional, upon detection of high severity of heart disease based on the cardiac signals captured by the HED Examples of computing device include but are not limited to a laptop, a desktop, smartphone, a server, and any combination of these.

In several embodiments, the processor 1414 identifies a plurality of unique physiological markers of the user based on historical cardiac signals captured by the HED 1402. In an embodiment, processor 1414 is configured to present a plurality of instructions regarding the management of the user's disease. The touchscreen controller 1424 displays cardiac information received from the HED 1402 that is derived from the cardiac sensor signal data.

In an embodiment, the touchscreen controller 1424 is a capacitive touch screen that uses the conductive touch of a human finger or a specialized input device. The touchscreen controller 1424 provides a User Interface (UI) used by the user or an administrator to initiate a request to view the data assessed by the cardiac health assessment system and provide various inputs to the cardiac health assessment system 1400. In many of the embodiments, the UI also known as a Graphic User Interface (GUI) is a convenient interface for accessing the information related to the status of the user's cardiac health. The touchscreen controller 1424 may be operated by a display driver such as an LCD driver or a LED driver. In many embodiments, the touchscreen controller 1424 includes an ASIC (application-specific integrated circuit,) a digital signal processor (DSP) and/or any other suitable technology known to those skilled in the art.

In many embodiments, the plurality of parameters that may be sensed and/or monitored includes hypertension, atrial fibrillation, ischemic cardiomyopathy, aortic stenosis, aortic regurgitation, mitral stenosis, and/or mitral regurgitation. It is well-known that hypertension and atrial fibrillation can be detected using visual based analysis including but not limited to photoplethysmography and/or analysing acoustic patterns related to irregular heartbeats and/or velocity of blood-flow and/or patterns related to pulse transmit time. It is further well known that ischemic cardiomyopathy, aortic stenosis, aortic regurgitation, mitral stenosis, regurgitation can result in abnormal seismic and/or acoustic activity that can be detected using inertial measurement units, microphonic sensors and/or other soundwave-based technologies such as ultrasound transceivers. These abnormal seismic and/or acoustic activities may results from arterial blockages and/or abnormal sounds relating to excess blood-flow from cardiac leakages between chambers in the heart. In some embodiments, the cardiac health assessment system 1400 includes a battery 1418 configured to supply electrical power to the circuit board 1406. According to some embodiments, battery 1418 is based on Lithium Polymer (Li-Poly) and Lithium-Ion (Li-Ion). In some embodiments, the battery 1418 is operated by a power management integrated circuit such as power MOSFETs.

Figure 16:
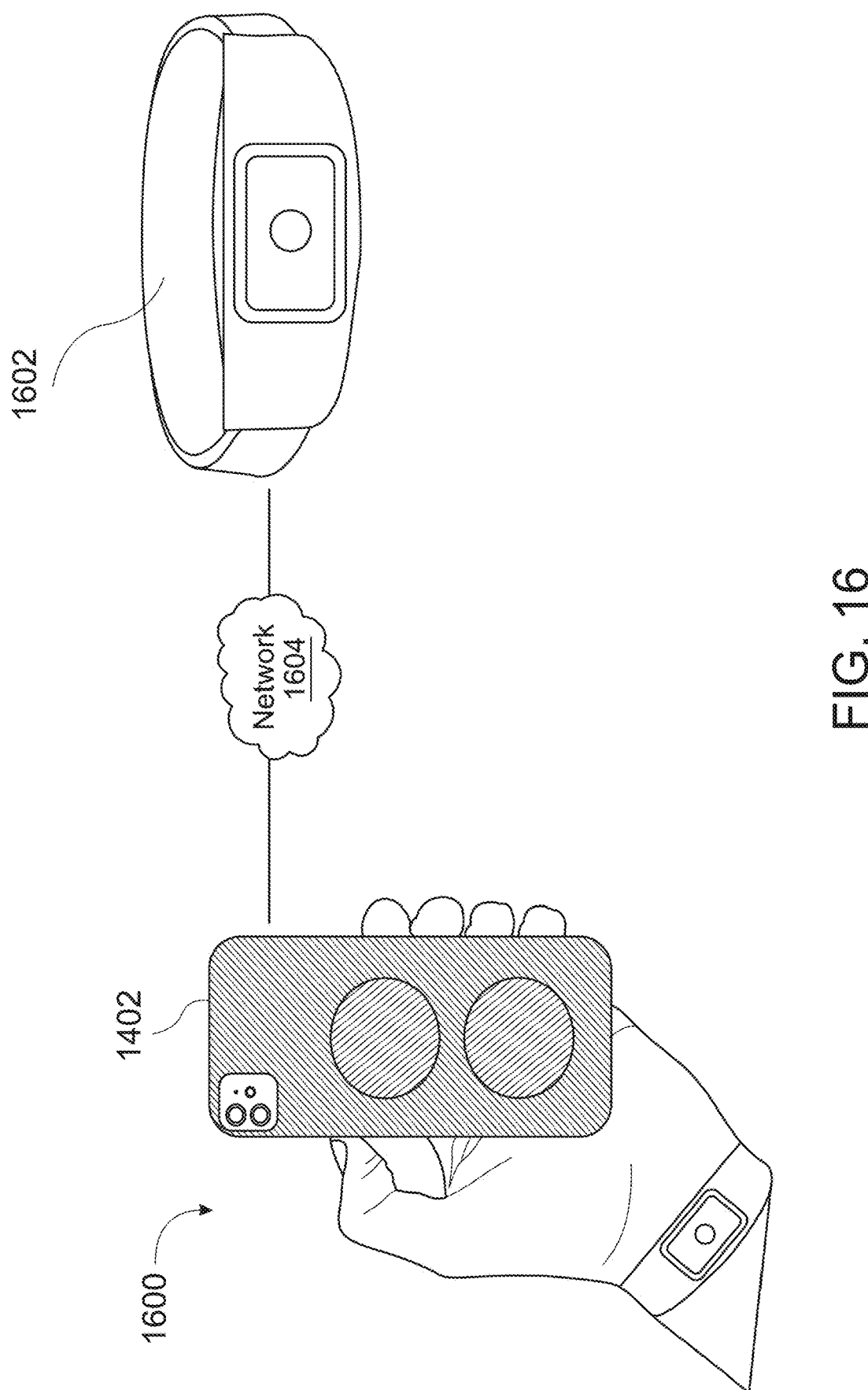
FIG. 16 illustrates a perspective view of a wearable device worn by the user to obtain physiological data of the user and transmit it to the HED over a network, in accordance with embodiments of the claimed subject matter.

FIG. 16 illustrates a system 1600 including a wearable device 1602 worn by the user to obtain physiological data of the user so that the physiological data can be transmitted to the HED 1402 over a network in accordance with several embodiments. Examples of a wearable device 1602 include but are not limited to a watch, a strap, a smartwatch, one or more pieces of smart jewellery such as rings, a wristband, a torso strap, or any other suitable device that can be worn or attached to a user and which can be used to sense data that can be transmitted to the HED 1402. In some embodiments, the wearable device 1602 includes one or more body-mounted sensors that monitor and transmit biological data for healthcare or other monitoring purposes. In many embodiments, the wearable device 1602 can act as a fitness tracker that monitors the physical activity and vital signs of the users. According to one embodiment, circuit board 1406 includes a transceiver to establish a communication with the network 1604. Network 1604 may be one or more wired or wireless networks, or any combination of wired and wireless networks, and the examples may include but are not limited to the internet, a Wireless Local Area Network (WLAN), a Wi-Fi network, a Long Term Evolution (LTE) network, a Worldwide Interoperability for Microwave Access (WiMAX) network, and a General Packet Radio Service (GPRS) network.

Figure 15:
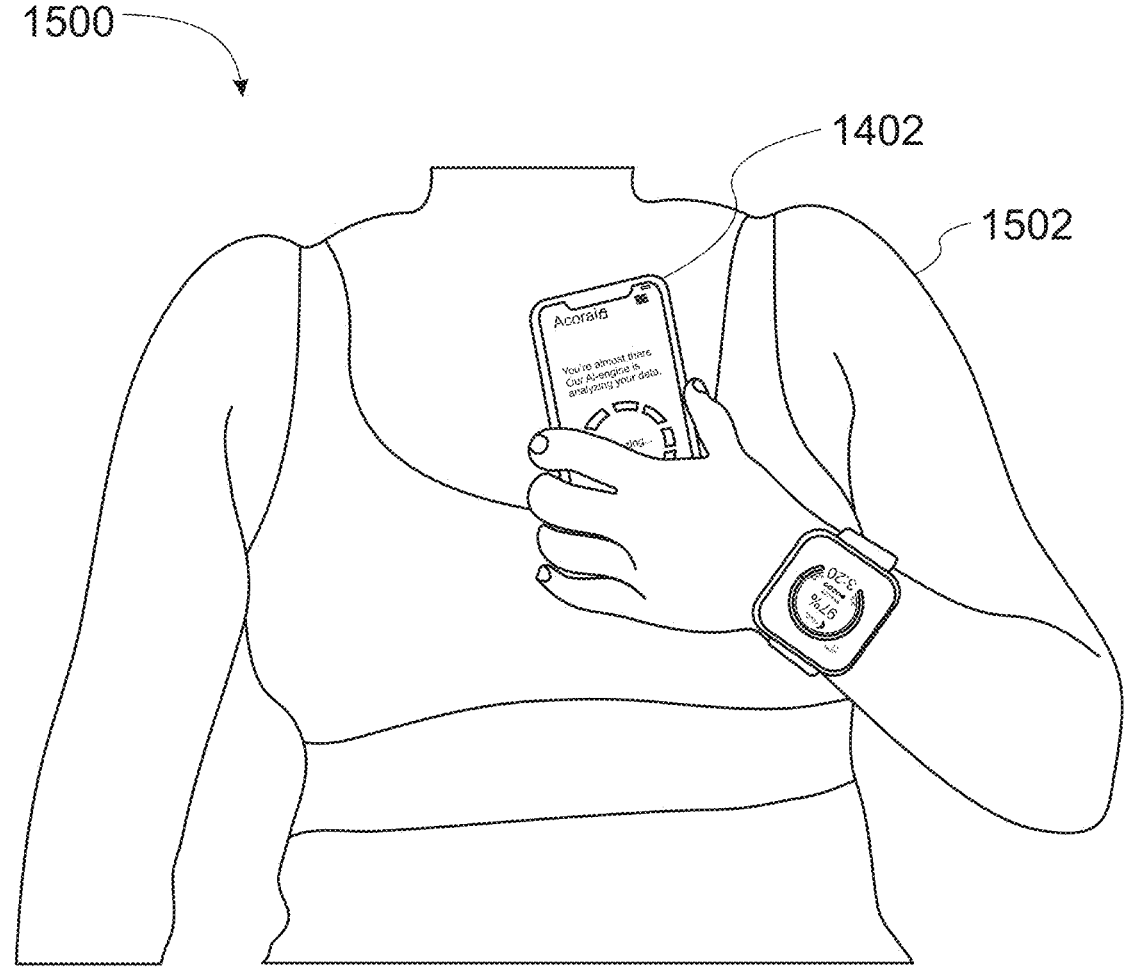
FIG. 15 illustrates a perspective view of the HED placed against the body or chest of a user, in accordance with embodiments of the claimed subject matter.

In an embodiment, the circuit board 1406 includes a diaphragm 1416 to enhance the cardiac audio signals captured by the microphonic sensor. FIG. 15 illustrates a perspective view 1500 of the HED 1402 placed against the body or chest of a user 1502 in accordance with several embodiments. In many embodiments, the circuit board 1406 includes an ultrasound transducer 1418 for transmitting high-frequency waves into the body of the user to detect data relating to many physiological processes including, but not limited to, intracardiac blood pressure and blood flow and return sound wave data. This data can then be analysed with the classification model and the regression model simultaneously with the detection, at a later time, or both simultaneously and a later time. In some embodiments, the circuit board 1406 includes an infrasound transducer 1420 for transmitting low-frequency waves into the body of the user to detect data relating to physiological processes and return wave data which can be analysed with the classification model and the regression model simultaneously with the detection, at a later time, or both simultaneously and a later time. In many embodiments, the circuit board 1406 includes a magnetometer 1422 for detecting abnormal or normal traces of ferromagnetic levels in the blood of the user. In many of the embodiments, the classification model and the regression model utilize machine learning (ML) to analyse the cardiac health of the user. Other models may also be used with or without ML and other data may be used in combination with the derived data.

FIG. 17 illustrates a flowchart 1700 of the method for cardiac health assessment, in accordance with embodiments of the claimed subject matter. The method includes step 1702 of integrating a memory, a circuit board, and a touchscreen controller in a HED In these embodiments, the touchscreen may comprise resistive and capacitive characteristics and may use indium tin oxide (ITO) sensors. Also in these embodiments, the HED has a shape adapted to fit firmly on the user's chest. The method includes step 1702 of storing, in a memory, a classification model, a regression model, and a plurality of instructions about a cardiac monitoring application. The circuit board includes a microphonic sensor, an IMU sensor, a camera sensor, a processor, a diaphragm, an ultrasound transducer, an infrasound transducer, and a magnetometer. The method includes step 1706 of capturing by the microphonic sensor cardiac sound wave signals indicative of the cardiac health of a user. The method includes step 1708 of using the IMU sensor to capture seismic signals indicative of the cardiac health of the user. The method includes step 1710 of using the camera sensor to perform visual data collection and/or photoplethysmography. The method includes step 1712 of using the processor to execute the cardiac monitoring application instructions. In many embodiments, the cardiac monitoring application may be based on one or more of the following operating systems:

Amazon Fire®, One UI®, Librem®, EMUI®, Android®, and iOS®. The method includes step 1714 of using the processor to display to the user one or more commands to position the HED against the chest of the user. The method includes step 1716 of detecting, by the processor, an abnormal cardiac activity arising from a plurality of parameters by deploying the classification model. In many embodiments, the plurality of parameters may include indications of hypertension, ischemic cardiomyopathy, atrial fibrillation, aortic stenosis, aortic regurgitation, mitral stenosis, and/or mitral regurgitation. The method includes step 1718 of estimating, by the processor, intracardiac pressure and/or ejection fraction by deploying the regression model. In some embodiments, the classification model and/or the regression model are trained by using intracardiac pressure data measured from a catheter and/or an invasive sensor (sensors that are recognized as providing gold standard data.) The method includes step 1720 of displaying, by the touchscreen controller, cardiac information derived from the cardiac sound wave signals received from the microphonic sensor. The method further comprises step 1722 of supplying, by a battery, electrical power to the circuit board. In some embodiments, the processor triggers a message transmission to a computing device of a healthcare professional (or any other device capable of receiving messages) upon a detection of high severity of heart disease based on the cardiac sound wave signals captured by the microphonic sensor. In many embodiments, the processor identifies a plurality of unique physiological markers of the user based on historical cardiac sound wave signals captured by the microphonic sensor. The historical cardiac sound wave signals may have been previously captured by the microphonic sensor or the historical cardiac sound wave signals may have been captured by another microphonic sensor, another sensor or they may be derived from stored data contained in one or more databases. The stored data may be data that was manually entered or it may be data automatically captured by one or more other manual or automatic methods, for instance manually entering historical data by a health professional or using data captured over a range of patients and/or users at one time or over a period of time. In many embodiments, the processor is configured to present a plurality of instructions regarding the management of the user's disease.

The method further comprises step 1724 of obtaining, by a wearable device worn by the user, physiological data of the user and transmit it to the HED over a network. In many embodiments, the diaphragm enhances the cardiac audio signals captured by the microphonic sensor. Any other suitable signal enhancer known to those skilled in the art may be used to enhance the one or more signals in the embodiments. In many embodiments, the ultrasound transducer transmits high-frequency waves into the body of the user to deflect a plurality of physiological processes comprising intracardiac blood pressure and blood flow and return sound wave data to be analysed with the classification model and the regression model. In some embodiments, the infrasound transducer transmits low frequency waves into the body of the user to deflect the physiological processes and return wave data to be analysed with the classification model and the regression model. In an embodiment, the magnetometer detects abnormal traces of ferromagnetic levels in the blood of the user.

Medication Non-Adherence Example

Figure 11:
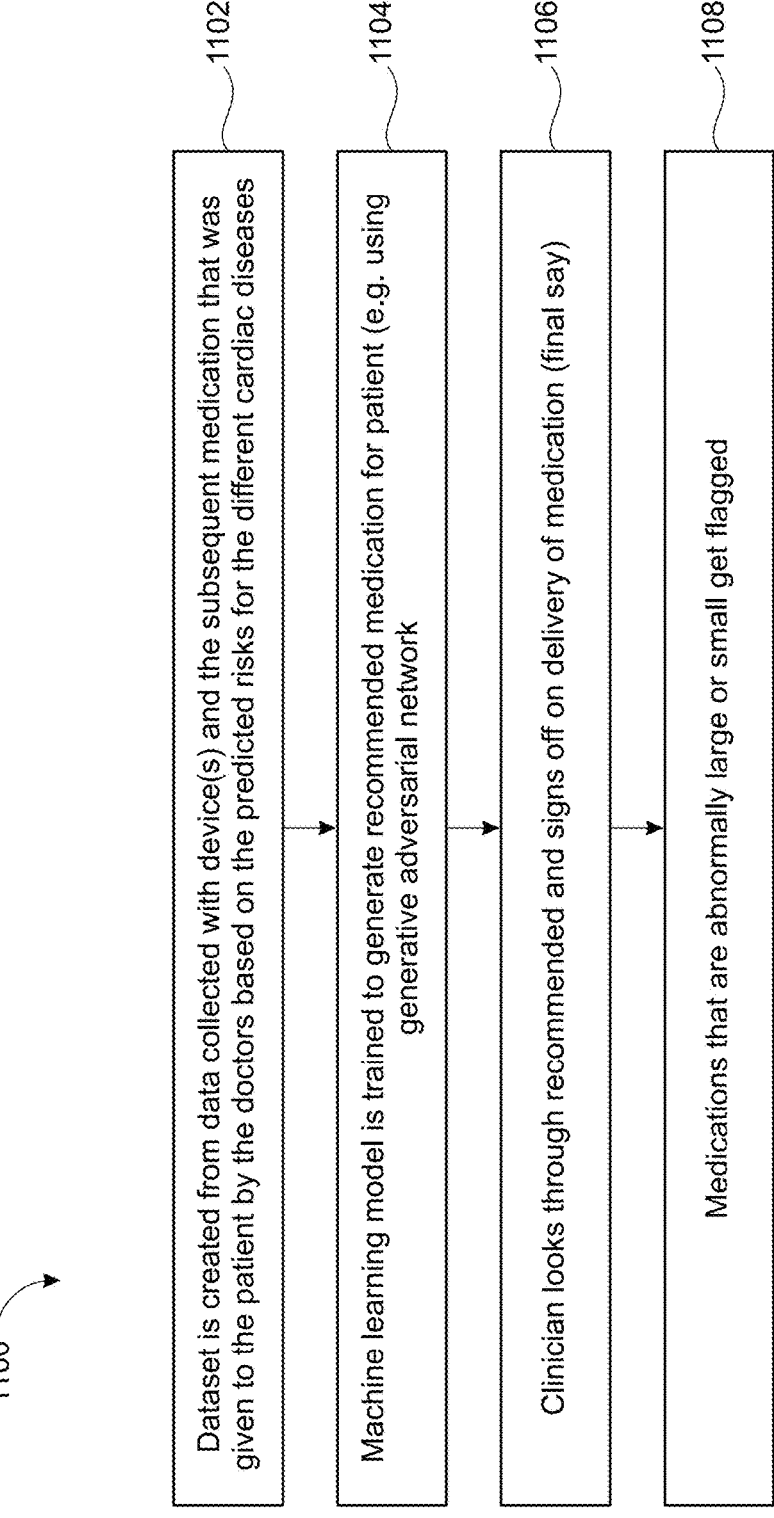
FIG. 11 illustrates a flowchart of an example machine learning model trained to adjust medicines.

In another example embodiment, the classification model and the regression model are trained to detect non-adherence to medication. FIG. 11 illustrates an example flowchart of a machine learning model trained to learn to adjust medicines, in accordance with an alternative embodiment of the present invention. At step 1102, a dataset is created from the data collected from the data collected from the wearable device(s) and the subsequent medication that was given to the patient by the doctors based on the predicted risks for the different cardiac diseases. At step 1104, the machine learning model is trained to generate recommended medication for the patient (e.g., using a generative adversarial network). Such a system may be a simple rules-based system, whereby a deterioration in heart failure identified in the non-invasive sensor data triggers a one standard deviation increase in the dosage of the patient's diuretic medicine until unsafe dosages are reached and/or the cardiac health of the patient begins to improve. Similarly, an improvement in cardiac health may trigger a one standard deviation reduction in the patient's dosage until a guideline directed medical therapy baseline for the patient's medicine is reached. Previous studies have shown that diuretic (e.g. Loop and/or Thiazide) is the most commonly adjusted heart failure medicine when using intracardiac pressure to guide therapy. Other common heart failure medicines that may be adjusted include Vasodilators (e.g. Nitrate and Hydralazine), ACEI/ARB, Beta Blockers and/or Aldosterone Antagonists. These dosage changes may be communicated to the patient through their clinician, and/or remotely through a communication application. In an embodiment the patient would be responsible of dosing their medicine based on the guidelines that they receive and/or new medicine based on new dosages could be sent to the patient's home. At step 1106, the clinician looks through recommended and signs off on the delivery of medication. At step 1108, the system flags medications that are abnormally large or small. In some embodiments, the classification model and the regression model are sub-module of the machine learning models which are trained on a coronary artery disease gold standard, i.e., a diagnosis based on CT-scan and/or coronary angiography. In some embodiments, the present system performs arrhythmia analysis is performed by machine learning models which are trained on a diagnosis based on ECG reading.

In some embodiments, the medicines are adjusted based on general parameters such as if the risk of arrhythmias has gone up, the user would be given a higher dose of medicines to prevent a heart stroke (people with atrial fibrillation are more at risk of having a stroke). Further, if coronary artery disease risk has gone up then Cholesterol-modifying medications, Aspirin, Beta-blockers, Calcium channel blockers, Ranolazine, Nitroglycerin and/or Angiotensin-converting enzyme (ACE) inhibitors, and angiotensin II receptor blockers (ARBs) may be increased. The present system can also follow Guideline-directed medical therapy (GDMT) to adjust the medicines.

In some embodiments, the adjusted medications may be delivered through an automated medicine dispensing device. Such an automated medicine dispensing device (AMDD) may take the form of a pill dispenser which is communicatively connected to a network through a processor and which receives information through the network of how much medicine shall be dispensed to the user each day and which type of medicine should be dispensed to the user each day. For example, upon detection of higher intracardiac pressure of the user, the amount of diuretic medicine dispensed to the user may increase until the intracardiac pressure is stabilized. The AMDD may contain one or more dispensing containers and one or more storage containers. The dispensing container may receive the medicine (e.g. in the form of one or more pills) from the storage container. One or more doors may exist between the dispensing container and the one or more storage containers. A channel may exist from the one or more storage containers to transport the medicine to the one or more dispensing containers. In some embodiments, one storage container may contain diuretic medicine and another storage container may contain beta-blocker medicine and another storage container may contain ACE-inhibitor medicine. The processor within the AMDD may receive information about dosage from a computing device and/or server which may trigger one or more doors from the one or more storage containers to open and dispense an amount of medicine corresponding to the dosage information received through the network. The AMDD may contain a weight sensor (e.g. to ensure accurate dosage of medicine) and/or a counting mechanism (e.g. to ensure that the right number of pills are dispensed to the user). A pill dispensing device may further be controlled manually, where dosage levels can be pre-set by the user based on direct or indirect information received from one or more healthcare professionals. In such an embodiment, the user may receive information of how many pills and/or how much medicine to take from each container to optimise.

Vein Thromboembolism (VTE) Diagnostic and Treatment Example

Figure 7A:
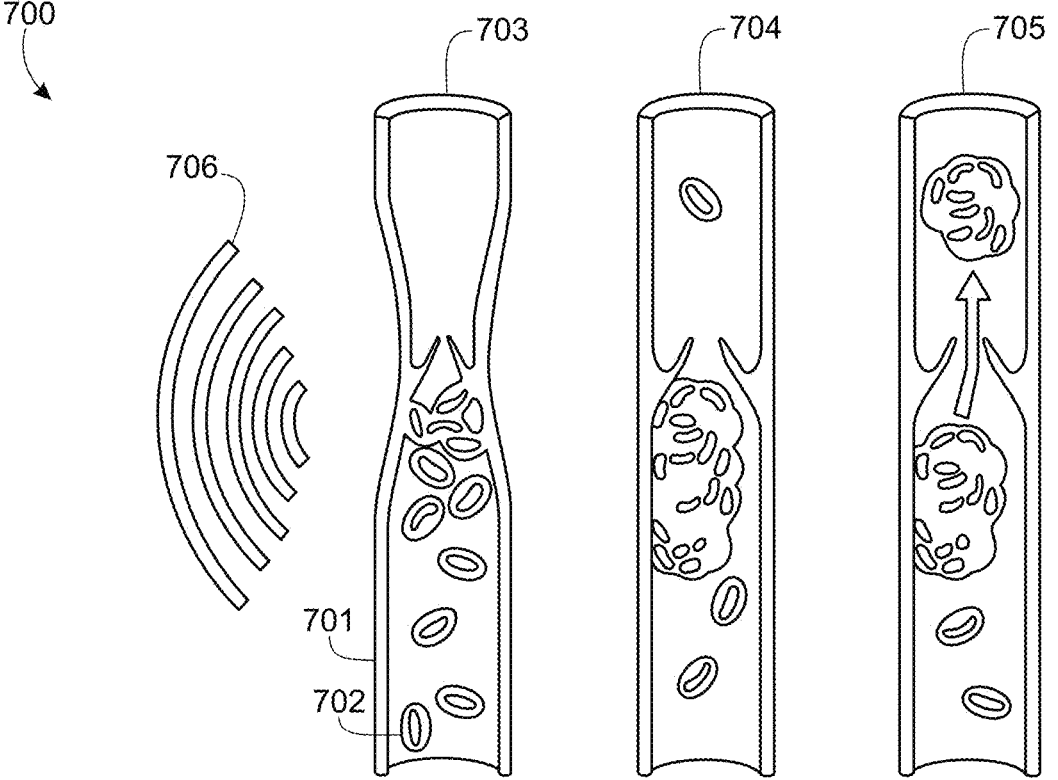
FIG. 7A illustrates a perspective view of the generation of a signalling from a deep vein thrombosis that can be used by an example embodiment of the cardiac health assessment system and method for detecting changes in a coronary artery due to blockages.

FIG. 7A illustrates a perspective view 700 of signal detection for detecting changes in veins due to blockages. As blood flow 702 within a vein 701 becomes clotted, thrombus starts building up and the beginning of blockages may be possible to observe 703. This process of blockages continues and occlude blood flow within the vein 704. At some point said blockages may become too big and be released in the rest of the cardiac system, known as an embolus 705. This may result in pulmonary embolism and is potentially fatal. These internal venous dynamics provide signals 706 that can be identified using a number of sensors, including but not limited to IMU sensors, soundwave transducers and ultrasonic sensors.

Figure 7B:
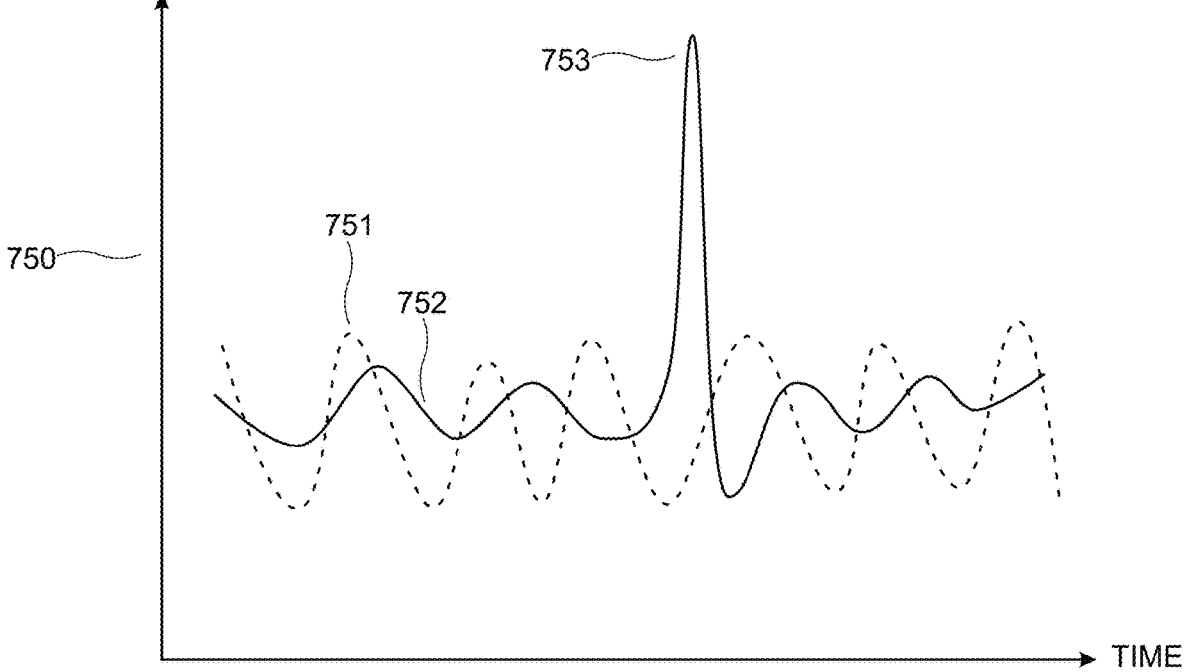
FIG. 7B illustrates an example waveform of the IMU and/or soundwave signal level and a detectable irregularity that can be analysed by some of the example systems and methods herein.

FIG. 7B illustrates a graphical representation 750 of an example IMU and/or microphone signal level, in accordance with at least one embodiment. FIG. 7B depicts a graph of a typical IMU data waveform but with an irregularity indicated. Time is represented on the x-axis through units of tenths of a second. The y-axis is represented by IMU signals which may include but are not limited to units of specific force, angular rate, and orientation. When clots build-up and/or are released 703, 704, 705, as shown in FIG. 7A, the internal dynamics of the vein change and a waveform typically associated with smooth blood flow may temporarily be disrupted with an indicator such as the spike 753. Normal blood flow can be expected to be represented by a more steady and recurring wavelike form 751, 752. Said disruptions may not be easily identifiable and require machine learning methods to detect microscopic perturbations and variance in venous blood flow. Such intervals may reveal underlying hemodynamic problems, thus representing another reason why unique data points relating to IMU and/or other sensor technology through the extended wear IMU and physiological sensor monitor described herein can be important for understanding the general health of a patient. The long-term data acquisition of these IMU data points, obtained through extended wear of the wearable monitor, can give the patient valuable insights into the patient's hemodynamic function and general physical health. The present computer-implemented system and method can be utilized in modern technology to detect heart failure at a very early stage which is not only affordable but also accurate.

The example trained classification model and the regression model are configured to estimate intracardiac pressure of the user; estimate coronary artery disease risk of the user; estimate arrhythmia risk of the user; and adjust one or more medications of the patient based on the estimations of the intracardiac pressure, coronary artery disease risk, and heart arrhythmia risk of the user. FIG. 10 illustrates a flow chart of an example method that performs these functions. These are several independent models that each estimate their own gold standard data. Heart failure hospitalizations are not always preceded by rising intracardiac pressures. Therefore, it is important to look at common precipitating factors of heart failure hospitalizations as well. The precipitating risk factors include but are not limited to deteriorations in pulmonary health (e.g. Chronic obstructive pulmonary disease (COPD) or any type of obstructive lung disease characterized by long-term breathing problems and poor airflow, pulmonary fibrosis, respiratory syndromes, increases in lung fluid levels and/or pulmonary embolism), increases in body fluid index levels, coronary artery disease/myocardial ischemia, heart arrhythmias, uncontrolled hypertension, medicine and diet non-adherence.

Exercise Alert Example

In some embodiments, the communication application alerts the user to perform an exercise like walking, jogging, or cycling. For example, upon non-invasive detection of hypertension or increases in estimations of intracardiac pressure data between night and morning, on the handheld electronic device 102 the user is provided an alarm or notification instructing the user to exercise and/or adhere to their medicine and diet until their intracardiac pressure returns to normal.

In another embodiment, the communication application alerts the user to perform an exercise like walking, jogging, or cycling. Further, the communication application senses rising intracardiac pressure through the non-invasive sensor device and/or the wearable device, predicts the user's cardiac health and notifies the user about how to reduce heart failure by addressing risk factors.

Hypertension Detection Example

In an example embodiment, the classification model is trained to detect hypertension. In some embodiments, the regression model is trained to estimate blood pressure. The classification model threshold for hypertension may be based on the 2020 International Society of Hypertension guidelines definitions of hypertension based on office blood pressure$\geq$140/90 mmHg or home monitoring blood pressure$\geq$135/85 mmHg, or 24-hour ambulatory blood pressure average$\geq$130/80 mmHg (daytime average$\geq$135/85 mmHg or night-time average BP$\geq$120/70 mmHg). The gold standard to train these models may be invasive (e.g. through radial arterial catheter-based pressure monitoring methods) or non-invasive (e.g. cuff-based pressure monitoring devices). It should be understood that the blood pressure models will be trained in a similar manner to those disclosed with regard to training machine learning models on intracardiac pressure data.

Unless otherwise defined, all terms including technical and scientific terms used in this disclosure have the same meaning as commonly understood by one of ordinary skill in the art to which this disclosure belongs. It is to be understood that the phrases or terms herein are for the purpose of description and not of limitation. As will be appreciated by one of skill in the art, the present disclosure may be embodied as a device, system, and method or computer program product. Further, the present invention may take the form of a computer program product on a computer-readable storage medium having computer-usable program code embodied in the medium. The present systems and methods have been described above referring to specific examples. However, other embodiments and examples than the above description are equally possible within the scope of the claims. The scope of the disclosure and its embodiments may be limited only by the corresponding patent claims. Even though modifications and changes may be suggested by the persons skilled in the art, it is the intention of the inventors and applicants to embody within the patent warranted heron all the changes and modifications as reasonably and properly come within the scope of the contribution the inventors and applicants to the art.

Regarding additional interpretation and construction of terms and steps herein, method steps are not in any specified order unless dictated by the context or specific wording. The data capture methods herein may be implemented by performing or completing manually, automatically, and/or a combination of thereof "Manually" refers to the fact that the diagnostic readings can be inputted into a computer after the measurements are taken. The term "method" refers to manners, means, techniques, and procedures for accomplishing any task including, but not limited to, those manners, means, techniques, and procedures either known to the person skilled in the art or readily developed from existing manners, means, techniques and procedures by practitioners of the art to which the present invention belongs. The persons skilled in the art will envision many other possible variations within the scope of the present systems and methods described herein.

In addition, a use of a word in the singular form should be interpreted where the context allows, or does not restrict, so as to enable plurality or an "at least one" construction. The listing or use of computer hardware or software should not limit the variations of embodiments possible from the claimed features that a person of ordinary skill in the art would understand from the specification, Figures, and claims. The term "and/or" in a list means all list items present, some list items present, or one of the list items present, unless such construction is limited by the context. The term "including" (or "includes") means "including, but not limited to" (or "includes but is not limited to"). The phrase "In some embodiments" means in one or more embodiments, and such embodiments may overlap or be completely distinct from other embodiments associated with recitations of the same phrase. Headings are for convenience of the reader only and not to be construed as limiting.

The invention claimed is:

1. A cardiac health assessment system for use with a handheld electronic device (HED) for assessing cardiac health of a user, characterized in the cardiac health assessment system comprising:

an electronic device case (EDC) having a shape adapted to secure the handheld electronic device with the EDC, wherein the EDC comprises a sensor signal-enhancing material to amplify auscultation signals; and a circuit board configured within the EDC and electrically connected with a plurality of sensors, wherein the plurality of sensors comprise:

a plurality of soundwave transducers to capture cardiac audio signals indicative of the cardiac health of the user;

a plurality of photoplethysmography (PPG) sensors to capture visual data pertaining to tissue colour and/or blood flow;

a plurality of Inertial Measurement Unit (IMU) sensors to capture seismic and auscultation signals indicative of the cardiac health of the user; and

a microcontroller connected to the circuit board to transmit cardiac health data received from the plurality of sensors to a computing device over a network, wherein the computing device comprises a processor configured to:

receive, in one or more temporal windows, representations of one or more signals recorded by the EDC, of at least one of the plurality of IMU sensors, the plurality of PPG sensors, and the plurality of soundwave transducers;

detect features of the one or more signals from at least one or more portions of the received representations falling within each of the one or more temporal windows; and identify patterns of the features of respective sensors from within the at least one or more portions based on at least a classification model or a regression model.

2. The cardiac health assessment system according to claim 1, wherein the processor is further configured to estimate, based on the regression model, intracardiac pressure and/or left ventricular ejection fraction.

3. The cardiac health assessment system according to claim 1, wherein the EDC is configured to capture cardiac health data of the user when positioned against the chest of the user.

4. The cardiac health assessment system according to claim 1, wherein the classification model is trained to detect irregularities from one or more of the following health conditions: ischemic cardiomyopathy, aortic stenosis, aortic regurgitation, mitral stenosis, and mitral regurgitation.

5. The cardiac health assessment system according to claim 1, wherein the EDC further comprises a temperature sensor configured to detect variations in chest skin surface temperature.

6. The cardiac health assessment system according to claim 1, wherein one or more soundwave transducers of the plurality of soundwave transducers are configured to transmit soundwaves into the user's body to deflect soundwaves arising from a plurality of physiological processes comprising intracardiac blood pressure and heart movements and return soundwave data to be analyzed with the classification model and the regression model.

7. The cardiac health assessment system according to claim 1, wherein the EDC further comprises a lens configured to envelop a camera of the handheld electronic device (HED), wherein the lens is configured to block external light when the HED shines a light onto skin of the user that is used to record one or more images thereof, wherein the one or more images are analyzed based on machine learning for providing insights into the cardiac health of the user.

8. The cardiac health assessment system according to claim 1, further comprising a separate handheld electronic device (HED), wirelessly connected with the handheld electronic device and comprising a HED wireless transceiver configured to establish a communication with the computing device to transmit cardiac health data therebetween, wherein the processor of the computing device is configured to:

detect, based on the classification model, an abnormal cardiac activity based on a plurality of parameters that includes one or more indications of hypertension, atrial fibrillation, and myocardial ischemia; and estimate, based on the regression model, intracardiac pressure and/or left ventricular ejection fraction.

9. The cardiac health assessment system according to claim 1, further comprising a plurality of electrodes, wherein the plurality of electrodes comprise:

a first ECG electrode placed on an outer surface of the EDC; and a second ECG electrode and a third electrode placed on each side of the EDC to facilitate a thumb and fingers of the user to be placed on the EDC having the shape that is adapted to secure the handheld electronic device, wherein the plurality of electrodes are configured to capture data indicative of the cardiac health of the user, wherein the processor is configured to transmit data indicative of cardiac function from the handheld electronic device to a clinician computing device over the network for remote diagnostic analysis using machine learning.

10. The cardiac health assessment system according to claim 9, further comprising a plurality of printed circuit boards (PCBs) to accommodate a plurality of sensing units with a plurality of dimensions.

11. The cardiac health assessment system according to claim 1, wherein the circuit board comprises a memory to store the classification model, the regression model, and a plurality of instructions pertaining to a cardiac monitoring application.

12. The cardiac health assessment system according to claim 8, wherein the processor is further configured to detect abnormal pulmonary health activity based on the plurality of parameters by deploying a pulmonary disease classification model.

13. The cardiac health assessment system according to claim 1, wherein the plurality of sensors further comprises a hydration monitoring sensor configured to compute a hydration metric of a body tissue of the user.

14. The cardiac health assessment system according to claim 12, wherein the processor is further configured to estimate lung fluid levels based on the plurality of parameters by deploying a lung fluid estimation model when the EDC has collected data from a thoracic region of the user.

15. The cardiac health assessment system according to claim 1, wherein the processor is further configured to compare an estimated intracardiac pressure with one or more earlier estimations of intracardiac pressure of the user.

16. The cardiac health assessment system according to claim 1, wherein the processor is further configured to estimate, based on the classification model, coronary artery disease risk.

* * * * *